(12) United States Patent
Hu

(10) Patent No.: US 10,649,053 B2
(45) Date of Patent: May 12, 2020

(54) CARDIAC LATE GADOLINIUM ENHANCEMENT MRI FOR PATIENTS WITH IMPLANTED CARDIAC DEVICES

(71) Applicant: The Regents of the University of California, Oakland, CA (US)

(72) Inventor: Peng Hu, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 692 days.

(21) Appl. No.: 14/440,346

(22) PCT Filed: Nov. 1, 2013

(86) PCT No.: PCT/US2013/068161
§ 371 (c)(1),
(2) Date: May 1, 2015

(87) PCT Pub. No.: WO2014/071249
PCT Pub. Date: May 8, 2014

(65) Prior Publication Data
US 2015/0346304 A1    Dec. 3, 2015

Related U.S. Application Data

(60) Provisional application No. 61/722,081, filed on Nov. 2, 2012.

(51) Int. Cl.
*G01R 33/56* (2006.01)
*A61B 5/02* (2006.01)
*A61B 5/044* (2006.01)
*A61N 1/05* (2006.01)
*A61K 49/10* (2006.01)
(Continued)

(52) U.S. Cl.
CPC ...... *G01R 33/5602* (2013.01); *A61B 5/02028* (2013.01); *A61B 5/044* (2013.01); *A61B 5/055* (2013.01); *A61K 49/103* (2013.01); *A61K 49/105* (2013.01); *A61N 1/05* (2013.01); *G01R 33/5601* (2013.01); *G01R 33/5635* (2013.01); *G01R 33/56325* (2013.01)

(58) Field of Classification Search
CPC .................................................. G01R 33/5602
See application file for complete search history.

(56) References Cited

U.S. PATENT DOCUMENTS 6,205,349 B1    3/2001  Kim et al.
9,618,590 B2 *  4/2017  Flores .................. G01R 33/287
(Continued)

OTHER PUBLICATIONS

List of MRI compatible and incompatible devices. Retrieved from www.mrisaftey.com on Dec. 14, 2017.*
(Continued)

*Primary Examiner* — Luther Behringer
(74) *Attorney, Agent, or Firm* — Quarles & Brady LLP

(57) ABSTRACT

Disclosed herein are methods and systems for clinical practice of medical imaging on patients with metal-containing devices, such as implanted cardiac devices. In particular, Disclosed herein are methods and systems for improved late gadolinium enhancement (LGE) MRI for assessing myocardial viability for patients with implanted cardiac devices, i.e., cardiac pacemakers and implantable cardiac defibrillators.

18 Claims, 26 Drawing Sheets

(51) Int. Cl.
A61B 5/055 (2006.01)
G01R 33/563 (2006.01)

(56) References Cited

U.S. PATENT DOCUMENTS

| | | | | |
|---|---|---|---|---|
| 2002/0116028 | A1* | 8/2002 | Greatbatch | A61N 1/056 607/9 |
| 2003/0195570 | A1* | 10/2003 | Deal | A61N 1/372 607/9 |
| 2005/0245812 | A1 | 11/2005 | Kim | |
| 2008/0242973 | A1 | 10/2008 | Warmuth | |
| 2008/0265883 | A1 | 10/2008 | Wiggins | |
| 2010/0033179 | A1 | 2/2010 | Hargreaves et al. | |
| 2011/0044524 | A1* | 2/2011 | Wang | G01R 33/54 382/131 |
| 2011/0103670 | A1 | 5/2011 | Koch | |
| 2011/0304331 | A1 | 12/2011 | Takahashi et al. | |
| 2012/0194186 | A1* | 8/2012 | Rehwald | G01R 33/50 324/309 |

OTHER PUBLICATIONS

Akcakaya, et al., Accelerated Noncontrast-Enhanced Pulmonary Vein MRA With Distributed Compressed Sensing, Journal of Magnetic Resonance Imaging, 2011, 33:1248-1255.
Akcakaya, et al., Compressed Sensing with Wavelet Domain Dependencies for Coronary MRI: A Retrospective Study, IEEE Trans. Med. Imaging, 2011, 30(5):1090-1099.
Bernstein, et al., Chapter 6.2 Adiabatic Inversion Pulses, Handbook of MRI Pulse Sequences, Elsevier Academic Press, 2004, pp. 189-199.
Biglands, et al., Cardiovascular Magnetic Resonance Physics for Clinicians: Part II, Journal of Cardiovascular Magnetic Resonance, 2012, 14:66, 40 pages.
Dickfeld, et al., MRI-Guided Ventricular Tachycardia Ablation, Integration of Late Gadolinium-Enhanced 3D Scar in Patients With Implantable Cardioverter-Defibrillators, Cir. Arrhythm. Electrophysiol., 2011, 4:172-184.
Foo, et al., Myocardial Viability: Breath-Hold 3D MR Imaging of Delayed Hyperenhancement With Variable Sampling in Time, Radiology, 2004, 230:845-851.
Gao, et al., Compressed Sensing Using Prior Rank, Intensity and Sparsity Model (PRISM): Applications in Cardiac Cine MRI, Proc. Intl. Soc. Mag. Reson. Med., 2012, 20:2242.
Goetti, et al., Acute, Subacute and Chronic Myocardial Infarction: Quantitative Comparison of 2D and 3D Late Gadolinium Enhancement MR Imaging, Radiology, 2011, 259(3):704-711.
Hargreaves, et al., Metal-Induced Artifacts in MRI, AJR, 2011, 197:547-555.
Hu, et al., Contrast-Enhanced Whole-Heart Coronary MRI with Bolus Infusion of Gadobenate Dimeglumine at 1.5 T, Magnetic Resonance in Medicine, 2011, 65:392-398.
Hu, et al., Motion Correction Using Coil Arrays (MOCCA) for Free-Breathing Cardiac Cine MRI, Magnetic Resonance in Medicine, 2011, 66:467-475.
Kim, et al., Relationship of MRI Delayed Contrast Enhancement to Irreversible Injury, Infarct Age, and Contractile Function, Circulation, 1999, 100:1992-2002.
Kim, et al., The Use of Contrast-Enhanced Magnetic Resonance Imaging to Identify Reversible Myocardial Dysfunction, N. Engl. J. Med., 2000, 343:1445-1453.
Koch, et al., A Multispectral Three-Dimensional Acquisition Technique for Imaging Near Metal Implants, Magnetic Resonance in Medicine, 2009, 61:381-390.
Koch, et al., Imaging Near Metal with a MAVRIC-SEMAC Hybrid, Magnetic Resonance in Medicine, 2011, 65:71-82.
Langman, et al., Pacemaker Lead Tip Heating in Abandoned and Pacemaker-Attached Leads at 1.5 Tesla MRI, Journal of Magnetic Resonance Imaging, 2011, 33:426-431.
Langman, et al., Abandoned Pacemaker Leads are a Potential Risk for Patients Undergoing MRI, Pacing and Clinical Electrophysiology, 2011, 34(9):1051-1053.
Langman, et al., The Dependence of Radiofrequency Induced Pacemaker Lead Tip Heating on the Electrical Conductivity of the Medium at the Lead Tip, Magnetic Resonance in Medicine, 2012, 68(2):606-613.
Lu, et al. SEMAC: Slice Encoding for Metal Artifact Correction in MRI, Magnetic Resonance in Medicine, 2009, 62:66-76.
Lustig, et al., Sparse MRI: The Application of Compressed Sensing for Rapid MR Imaging, Magnetic Resonance in Medicine, 2007, 58:1182-1195.
Naehle, et al., Safety, Feasibility, and Diagnostic Value of Cardiac Magnetic Resonance Imaging in Patients with Cardiac Pacemakers and Implantable Cardioverters/Defibrillators at 1.5 T, American Heart Journal, 2011, 161(6):1096-1105.
Nazarian, et al., Clinical Utility and Safety of a Protocol for Noncardiac and Cardiac Magnetic Resonance Imaging of Patients With Permanent Pacemakers and Implantable-Cardioverter Defibrillators at 1.5 Tesla, Circulation, 2006, 114(12)1277-1284.
Nazarian, et al., How to Perform Magnetic Resonance Imaging on Patients With Implantable Cardiac Arrhythmia Devices, Heart Rhythm, 2009, 6(1):138-143.
Nazarian, et al., A Prospective Evaluation of a Protocol for Magnetic Resonance Imaging of Patients With Implanted Cardiac Devices, Am. Intern. Med., 2011, 155(7):415-424.
Nguyen, et al., A Fast Navigator-Gated 3D Sequence for Delayed Enhancement MRI of the Myocardium: Comparison With Breathhold 2D Imaging, Journal of Magnetic Resonance Imaging, 2008, 27:802-808.
Nguyen, et al., Free-Breathing 3D Steady-State Free Precession Coronary Magnetic Resonance Angiography: Comparison of Four Navigator Gating Techniques, Magn. Reson. Imaging, 2009, 27(6):807-814.
Peters, et al., Left Ventricular Infarct Size, Peri-Infarct Zone, and Papillary Scar Measurements: A Comparison of High-Resolution 3D and Conventional 2D Late Gadolinium Enhancement Cardiac MR, Journal of Magnetic Resonance Imaging, 2009, 30:794-800.
Rashid, et al., Improved Late Gadolinium Enhancement Cardiac MRI for Patients With Implanted Cardiac Devices, Proc. Intl. Soc. Mag. Reson. Med., 2013, 21:4560.
Roger, et al., Heart Disease and Stroke Statistics—2012 Update, a Report from the American Heart Association, Circulation, 2012, 125:e2-e220.
Roguin, et al., Modern Pacemaker and Implantable Cardioverter/Defibrillator Systems Can Be Magnetic Resonance Imaging Safe, Circulation, 2004, 110:475-482.
Rosenfeld, et al., A New Adiabatic Inversion Pulse, Magnetic Resonance in Medicine, 1996, 36(1):124-136.
Sasaki, et al., Quantitative Assessment of Artifacts on Cardiac Magnetic Resonance Imaging of Patients With Pacemakers and Implantable Cardioverter-Defibrillators, Cir. Cardiovasc. Imaging, 2011, 4:662-670.
Simonetti, et al., An Improved MR Imaging Technique for the Visualization of Myocardial Infarction, Radiology, 2001, 218:215-223.
Sommer, et al., Strategy for Safe Performance of Extrathoracic Magnetic Resonance Imaging at 1.5 Tesla in the Presence of Cardiac Pacemakers in Non-Pacemaker-Dependent Patients, Circulation, 2006, 114:1285-1292.
Sung, et al., Design and Use of Tailored Hard-Pulse Trains for Uniformed Saturation of Myocardium at 3 Tesla, Magnetic Resonance in Medicine, 2008,60:997-1002.
Tian, et al., Three-Dimensional Delayed-Enhanced Cardiac MRI Reconstructions to Guide Ventricular Tachycardia Ablations and Assess Ablation Lesions, Cir. Arrhythm Electrophysiol., 2012, 5:e31-e35.
Weber, et al., Whole-Heart Steady-State Free Precession Coronary Artery Magnetic Resonance Angiography, Magnetic Resonance in Medicine, 2003, 50:1223-1228.
Worters, et al., Compressed-Sensing Multi-Spectral Imaging of the Post-Operative Spine, J. Magn. Reson. Imaging, 2013, 37(1):243-248.

(56) References Cited

OTHER PUBLICATIONS

Wright, et al., Water Proton T1 Measurements in Brain Tissue at 7, 3, and 1.5 T Using IR-EPI, IR-TSE, and MPRAGE: Results and Optimization, Magn. Reson. Mater. Phy., 2008, 21:121-130.
Zipes, et al., Sudden Cardiac Death, Circulation, 1998, 98:2334-2351.
PCT International Search Report and Written Opinion, PCT/US2013/068161, dated Feb. 17, 2014.
European Patent Office, Extended European Search Report, Application No. 13852228.9, dated Apr. 19, 2017.

* cited by examiner

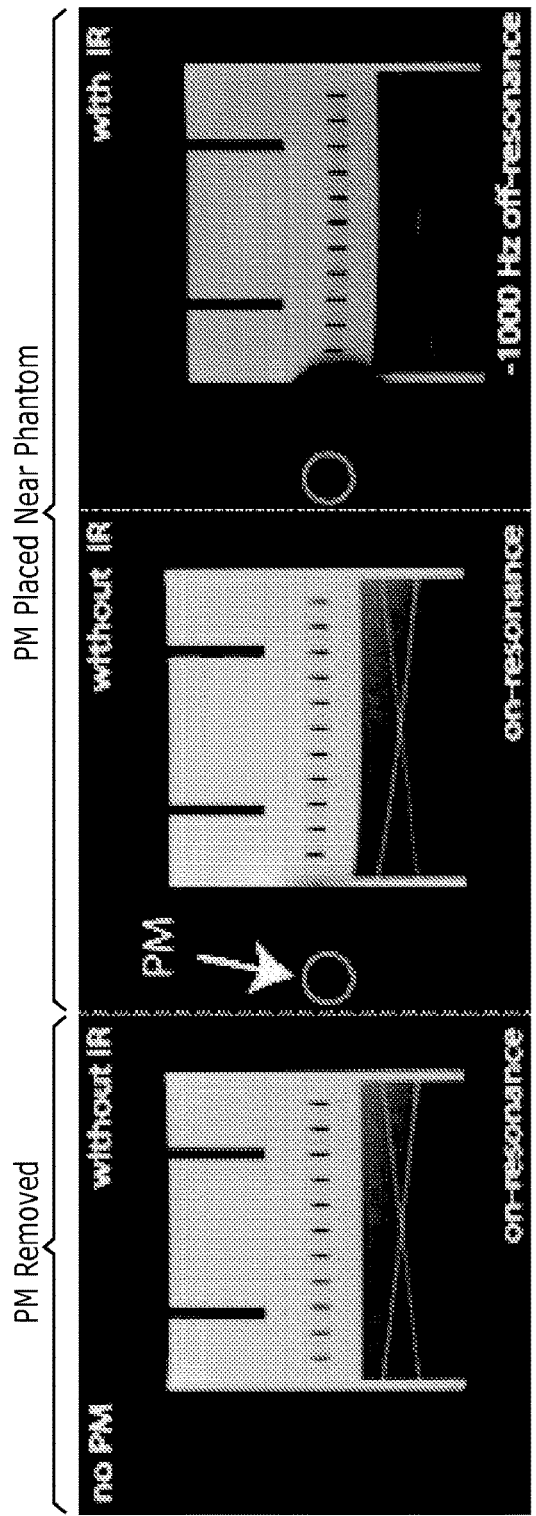
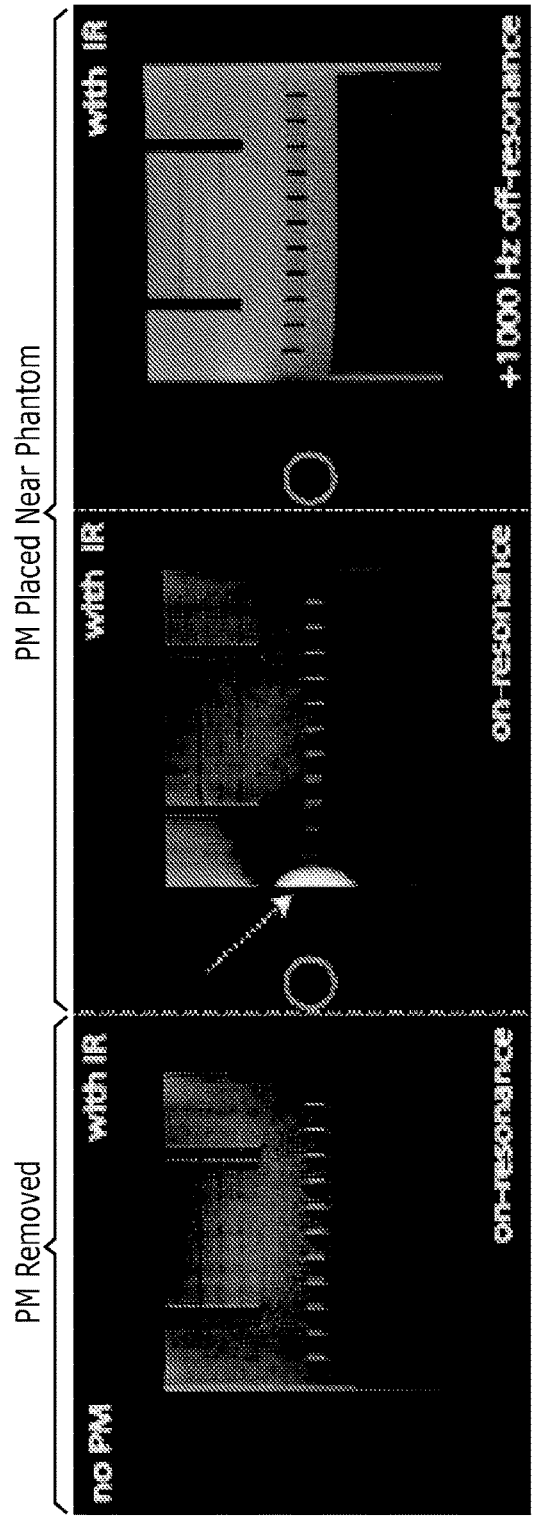
FIG. 2A  FIG. 2B  FIG. 2C
FIG. 2D  FIG. 2E  FIG. 2F

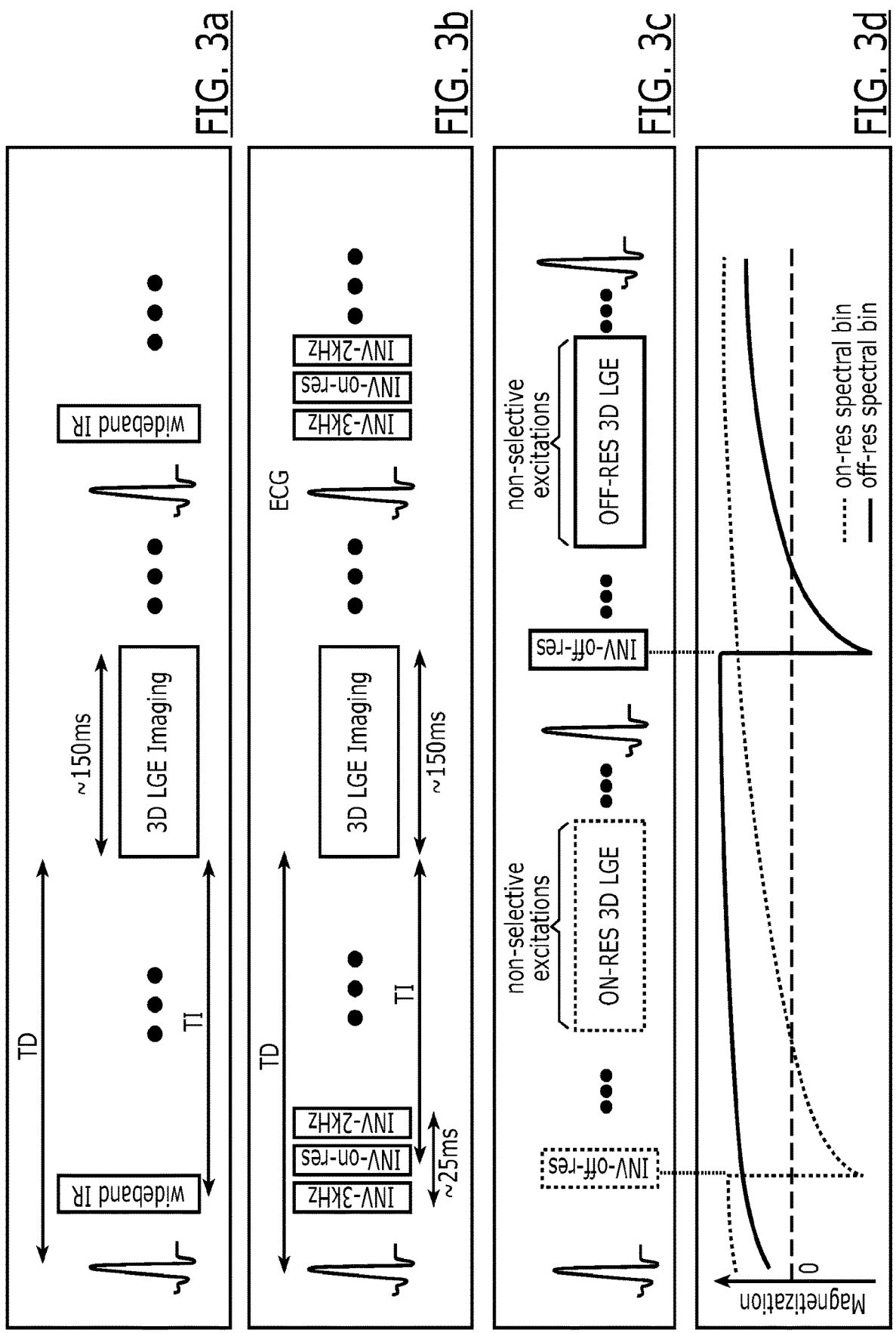

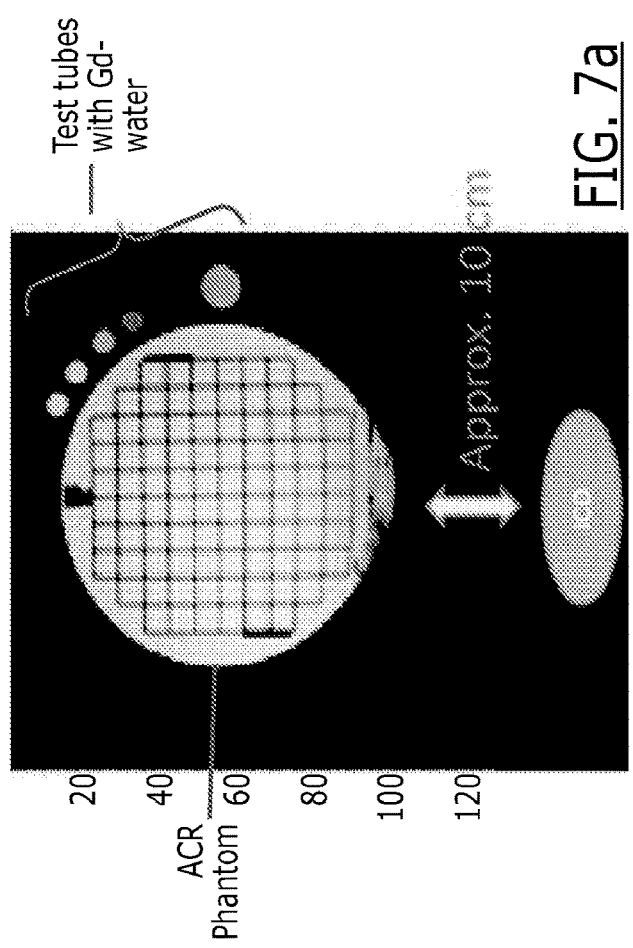
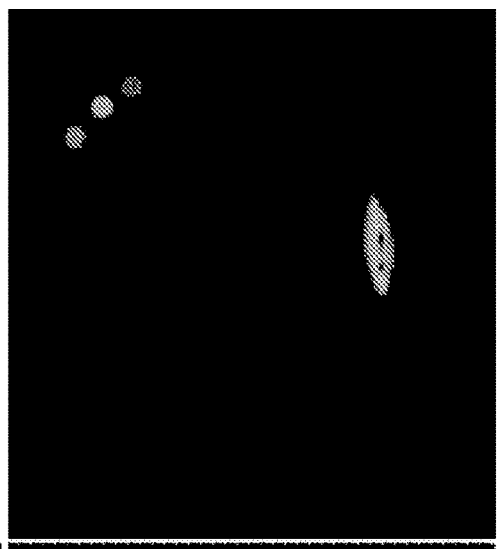
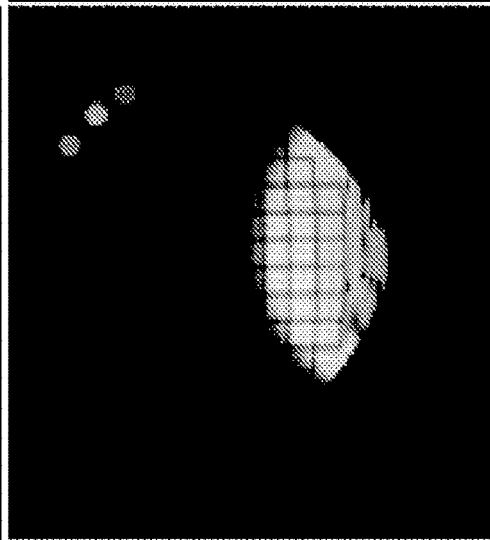
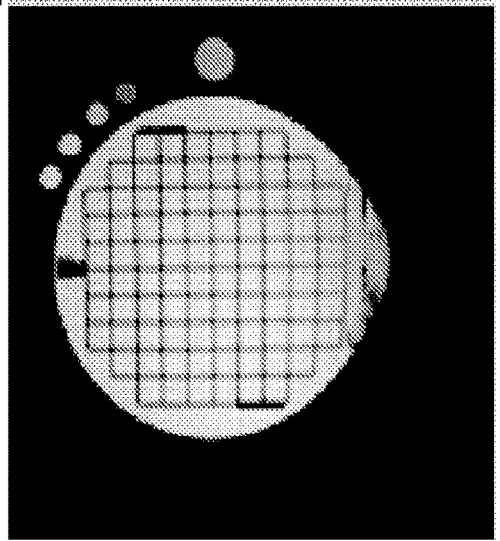
FIG. 7a
FIG. 7b
FIG. 7c
FIG. 7d

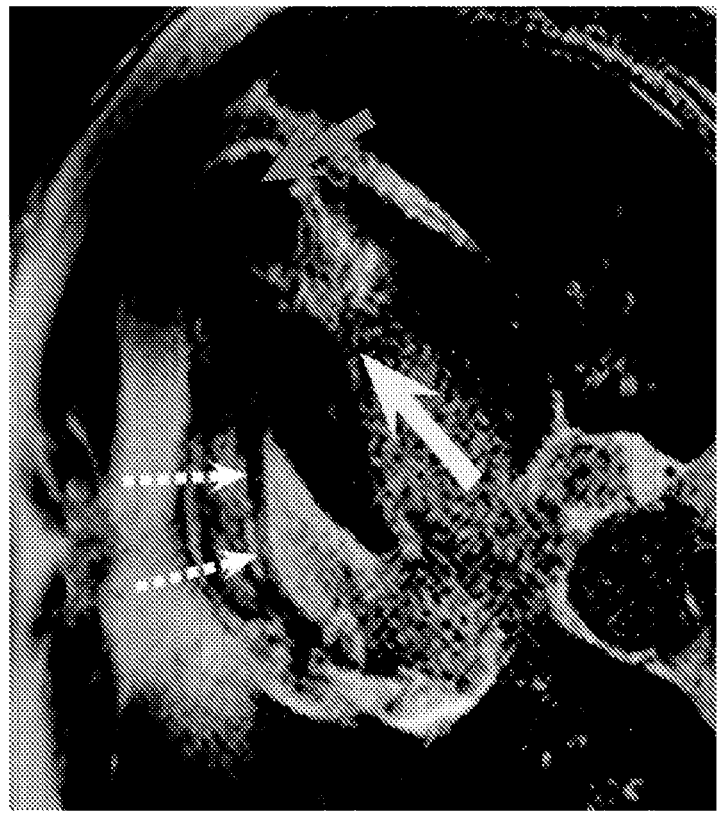
FIG. 13B
FIG. 13A

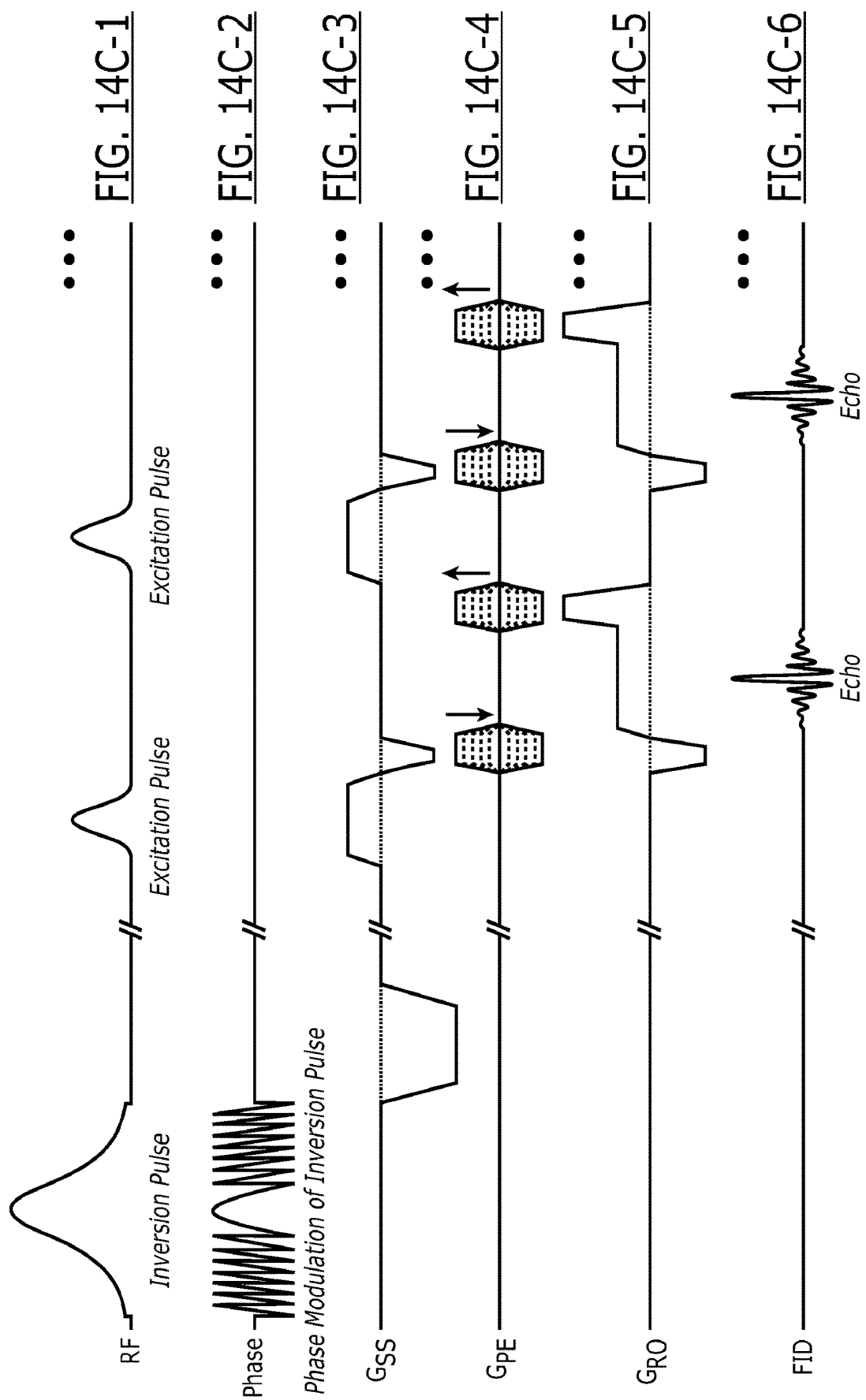

FIG. 15C-1  1.1 kHz Inv. Pulse
FIG. 15C-2  2.4 kHz Inv. Pulse
FIG. 15C-3  3.8 kHz Inv. Pulse No Frequency Offset
FIG. 15C-4  3.8 kHz Inv. Pulse Frequency Offset: 1.5 kHz

CARDIAC LATE GADOLINIUM ENHANCEMENT MRI FOR PATIENTS WITH IMPLANTED CARDIAC DEVICES

CROSS REFERENCE TO RELATED APPLICATION

The application is a US national stage entry of International application No. PCT/US2013/068161 filed on Nov. 1, 2013, which in turn claims priority to U.S. provisional application No. 61/722,081 filed on Nov. 2, 2012, each of which is hereby incorporated by reference herein in its entirety.

GOVERNMENT-SPONSORED RESEARCH AND DEVELOPMENT

This invention was made with Government support under Grant No. R21HL118533 awarded by the National Institutes of Health. The Government has certain rights in this invention

FIELD OF THE INVENTION

This invention relates to methods and systems for clinical practice of medical imaging on patients with metal-containing devices, such as implanted cardiac devices. More specifically, this invention relates to methods and systems for clinical practice of medical imaging on cardiac patients with implanted cardiac devices. Clinical practice includes, for example, device artifact reduction and electroanatomical mapping.

BACKGROUND

Currently, medical imaging techniques as such Magnetic Resonance Imaging (MRI), also known as nuclear magnetic resonance imaging (NMRI) or magnetic resonance tomography (MRT), are not applicable to patients with cardiac implant devices: partly because the myocardial scar (viability) imaging using late gadolinium enhancement MRI, which is a clinical gold standard for myocardial tissue characterization, are often nondiagnostic due to the presence of these devices.

Late gadolinium enhancement (LGE) cardiac MRI plays an important role in diagnosis and treatment of myocardial diseases. It is the clinical "gold standard" for non-invasive myocardial tissue characterization. Assessment of presence/absence, location, size and pattern of myocardial scar using LGE MRI is often the only non-invasive means of accurately diagnosing and differentiating various forms of non-ischemic cardiomyopathy, including myocarditis, arrhythmogenic right ventricular dysplasia, amyloidosis, and sarcoidosis. LGE MRI also plays an increasingly important role in guiding catheter ablations, a widely used treatment procedure for ventricular tachycardia (VT) and recurrent implantable cardioverter-defibrillator (ICD) therapies. For this procedure, the assessment of myocardial scar location, size and transmurality provided by LGE MRI allows more accurate identification of arrhythmogenic substrate and ablation sites, thereby potentially decreasing procedure time and increasing success rate.

Despite the important role of LGE MRI and the large number of patients for whom an LGE cardiac MRI could provide a non-invasive means of establishing diagnosis and guiding treatment, many of the patients do not undergo cardiac MRI due to prior implantation of cardiac devices. It has been estimated that up to 75% of patients who could benefit from LGE MRI are recipients of cardiac devices, such as implantable cardioverter defibrillators (ICD) and cardiac pacemakers (PM). Presence of cardiac devices are traditionally considered a contraindication for cardiac MRI. Potential risks of MRI for patients with ICDs or pacemakers include heating of the tissue adjacent to lead electrodes, mechanical forces and vibration, induction of arrhythmias, and alteration of device function. Numerous recent studies have demonstrated that it is safe to scan patients with cardiac devices who are not device dependent and have no abandoned leads if certain precautions are taken, including pre- and post-MRI interrogation of the device. In the United States, approximately 116,000 ICDs and 397,000 cardiac pacemakers were implanted in 2009. MRI of patients with implanted devices has been reported to be performed safely for most patients whose rhythms are not device dependent.

While these recent advances in MRI safety are encouraging, the diagnostic value of the LGE images for these patients, however, is often severely limited by significant imaging artifacts that arise from the device generator, a metal box that is implanted predominantly on the upper-left side of the patient's chest. The device generator results in multi-kHz off-resonance within myocardial tissue and typically causes hyper-intensity image artifacts in LGE images, which can appear similar to the hyper-enhancement of scar tissue (see, e.g., FIG. 1). A recent study has shown that these artifacts typically occur at regions of the heart that are close to the device generator, such as left ventricular (LV) apex, lateral wall, and outflow track. Artifacts due to the device also appear in cine and perfusion CMR images, but these are not as severe as those in LGE images. Additional MRI signal artifacts due to off-resonance, including image distortions, signal pile-up and signal voids are also a potential concern.

These bright-signal imaging artifacts have been previously reported; however, there has been no study to date that investigated the origin of the artifacts or proposed a solution to address this important issue.

What is needed are systems and methods that can overcome the deficiencies in the art.

SUMMARY OF THE INVENTION

Described herein are mechanisms, technical innovations, and clinical evaluation of a new multi-spectral LGE MRI technique that may be used routinely to significantly reduce LGE imaging artifacts in patients with implanted cardiac devices. Also described herein are clinical deployment of a set of MRI pulse sequences and reconstruction methods for LGE MRI and successful validation in a small cohort of patients with cardiac devices.

Provided herein are methods and systems for high quality late gadolinium enhancement scar imaging even in the presence of implanted cardiac devices. The technologies disclosed can be widely used by all major manufacturers of clinical MRI systems both in the U.S. and worldwide to eliminate any image quality issues associated with these cardiac devices. In some embodiments, a custom made MRI pulse sequence will be needed, which is a piece of software that controls the MRI system and can be easily implemented.

In one aspect, provided herein is an improved late gadolinium enhancement (LGE) magnetic resonance imaging (MRI) sequence, where the LGE-MRI has a center modulation frequency. The improved LGE-MRI sequence comprises shifting the center modulation frequency of the LGE-MRI sequence prior to collecting imaging information of the patient. The shifting of center modulation frequency is achieved by using a wideband adiabatic inversion pulse with a spectral bandwidth of 1 kHz or larger.

In some embodiments, the wideband inversion pulse is a wideband adiabatic inversion pulse. In some embodiments, the wideband inversion pulse is an IR inversion pulse. In some embodiments, the wideband inversion pulse has a spectral bandwidth selected from the group consisting of 1.5 kHz or larger, 2 kHz or larger, 2.5 kHz or larger, 3 kHz or larger, and 3.5 kHz or larger. In some embodiments, the wideband inversion pulse has a spectral bandwidth of 3.8 kHz.

In some embodiments, the wideband inversion pulse has a specific absorption rate (SAR) of 0.07 W/kg or lower.

In some embodiments, the center frequency shift is between the range of zero Hz to 2500 Hz or higher. In some embodiments, the center frequency shift is selected from the group consisting of 50 Hz or higher, 100 Hz or higher, 150 Hz or higher, 200 Hz or higher, 250 Hz or higher, 300 Hz or higher, 350 Hz or higher, 400 Hz or higher, 450 Hz or higher, 500 Hz or higher, 550 Hz or higher, 600 Hz or higher, 650 Hz or higher, 700 Hz or higher, 750 Hz or higher, 800 Hz or higher, 850 Hz or higher, 900 Hz or higher, 950 Hz or higher, 1000 Hz or higher, 1050 Hz or higher, 1100 Hz or higher, 1150 Hz or higher, 1200 Hz or higher, 1250 Hz or higher, 1300 Hz or higher, 1350 Hz or higher, 1400 Hz or higher, 1450 Hz or higher, 1500 Hz or higher, 1550 Hz or higher, 1600 Hz or higher, 1650 Hz or higher, 1700 Hz or higher, 1750 Hz or higher, 1800 Hz or higher, 1850 Hz or higher, 1900 Hz or higher, 1950 Hz or higher, 2000 Hz or higher, 2050 Hz or higher, 2100 Hz or higher, 2150 Hz or higher, 2200 Hz or higher, 2250 Hz or higher, 2300 Hz or higher, 2350 Hz or higher, 2400 Hz or higher, 2450 Hz or higher, and 2500 Hz or higher. In some embodiments, the center frequency shift is 800 Hz or larger or 1000 Hz or larger.

Also provided herein is a method for improved late gadolinium enhancement (LGE) magnetic resonance imaging (MRI) for assessing myocardial viability for a patient with a metal-containing device, comprising: collecting imaging information of the patient using a traditional LGE-MRI sequence; shifting the center modulation frequency of the traditional LGE-MRI sequence; and repeating the collecting step to collect additional imaging information of the patient. In some embodiments, the shifting of center modulation frequency is achieved by using a wideband adiabatic inversion pulse with a spectral bandwidth of 1 kHz or larger.

In some embodiments, the wideband inversion pulse has a spectral bandwidth selected from the group consisting of 1.5 kHz or larger, 2 kHz or larger, 2.5 kHz or larger, 3 kHz or larger, and 3.5 kHz or larger. In some embodiments, the wideband inversion pulse has a spectral bandwidth of 3.8 kHz.

In some embodiments, the metal-containing device includes but is not limited to an implanted cardiac device, a cardiac pacemaker, an implantable cardiac defibrillator (ICD), a catheter, or a balloon.

In some embodiments, the inversion pulse is an IR pulse. In some embodiments, the wideband inversion pulse is a wideband adiabatic inversion pulse.

In some embodiments, the center modulation frequency is shifted by a frequency selected from the group consisting of 750 Hz or higher, 800 Hz or higher, 850 Hz or higher, 900 Hz or higher, 950 Hz or higher, 1000 Hz or higher, 1050 Hz or higher, 1100 Hz or higher, 1150 Hz or higher, 1200 Hz or higher, 1250 Hz or higher, 1300 Hz or higher, 1350 Hz or higher, 1400 Hz or higher, 1450 Hz or higher, and 1500 Hz or higher. In some embodiments, the center modulation frequency shift is 800 Hz or larger. In some embodiments, the center modulation frequency shift is 1000 Hz or larger.

In some embodiments and being consistent with any of the embodiments disclosed herein, the method further comprises a step of determining an LGE MRI image, wherein the LGE MRI image comprises measurements of a scar area within the patient. In some embodiments, the scar area is selected from the group consisting of an endocardial scar area, epicardial scar area, and a transmural scar area.

In some embodiments and being consistent with any of the embodiments disclosed herein, the method further comprises a step of correlating an LGE MRI image with an electroanatomical map of the same patient, wherein the correlation is based on measurements of a scar area. In some embodiments, the scar area is selected from the group consisting of an endocardial scar area, epicardial scar area, and a transmural scar area.

In some embodiments, provided herein is a wideband multi-spectral 3D LGE MRI technique for patients with a metal-containing devices. Examples of the metal-containing device is selected from the group consisting of a pacemaker, an implantable cardiac defibrillator, a catheter, a balloon or etc.

In one aspect, an efficient respiratory motion gating strategy is developed.

In another aspect, the reliability of NAV for LGE-MRI in patients with cardiac devices and the potential artifacts generated by the NAV restoration inversion pulse is determined.

In another aspect, the developed technique in a small cohort of patients with cardiac devices is tested.

BRIEF DESCRIPTION OF THE DRAWINGS

Those of skill in the art will understand that the drawings, described below, are for illustrative purposes only. The drawings are not intended to limit the scope of the present teachings in any way.

FIGS. 2A, 2B, 2C, 2D, 2E, and 2F illustrate exemplary phantom images demonstrating effect of off-resonance on LGE images. Changing the modulation frequency of IR and excitation pulses in 2D LGE imaging from +1000 Hz to −1000 Hz confirms the bright signal artifact in LGE (dashed arrow) is caused by insufficient spectral coverage of the IR pulse. PM: pacemaker; IR: inversion recovery pulse.

FIGS. 3A, 3B, 3C and 3D illustrate exemplary multi-spectral LGE strategies: A) The traditional IR pulse is replaced with a wideband adiabatic IR pulse to ensure proper inversion of off-resonance myocardium. B) Non-selective IR pulses with different RF modulation frequencies are played back-to-back to ensure adequate spectral coverage. C) An alternative strategy where on-resonance (red) and off-resonance (blue) imaging (including inversion and excitation) are interleaved to reduce signal distortion/pile-up artifacts. D) Longitudinal magnetization for on- and off-resonance spectral bins. Each spectral bin is sampled at least every 2 R-R, allowing full recovery and improved myocardium-scar contrast.

FIGS. 7A, 7B, 7C, and 7D illustrate exemplary phantom results showing the developed LGE MRI technique with wideband inversion pulse. In the phantom setup shown in a), the ICD is placed ~10 cm from the ACR phantom. The traditional spoiled gradient echo sequence without any inversion is shown in b). Using traditional LGE MRI sequence shown in c), the regions far away from the ICD is inverted; however, region close to the ICD is not inverted and shows a bright signal because of off-resonance caused by the ICD which falls outside of the spectral bandwidth of the inversion pulse. Using the LGE MRI sequence with a wideband inversion pulse (see FIG. 6) as shown in d) demonstrates uniform inversion and suppression across the phantom. This data supports the hypothesis of this invention that the strong off-resonance caused by ICD prevents proper inversion of affected regions and that is the cause of the current problems with LGE MRI for patients with these cardiac devices.

FIGS. 13A and 13B illustrate an exemplary embodiment, showing LGE images in the 4-chamber HLA plane in Patient 4. A: LGE image using the conventional LGE sequence. Severe hyper-intensity artifact was formed in the ventricular wall around the apex (left arrow). B: LGE image using the wideband LGE sequence. The hyper-intensity artifact was completely eliminated. This patient has an apical aneurysm, which was obscured in the conventional LGE image (A, right arrow), but much clearer in the wideband LGE image (B, right arrow). A device lead was visible in the right ventricle (top dotted arrows), but it did not produce any noticeable artifact in the wideband image.

FIGS. 14A-1, 14A-2, 14A-3, 14B-1, 14B-2, 14B-3, 14C-1, 14C-2, 14C-3, 14C-4, 14C-5, 14C-5, and 14C-6 illustrate an exemplary embodiment, showing: A: RF properties and resultant longitudinal magnetization for the default conventional inversion pulse of BW 1.1 kHz. B: RF properties and resultant longitudinal magnetization for the new inversion pulse of BW 3.8 kHz. This inversion pulse is shown with a 1.5 kHz offset of the center of the modulation frequency. C: Pulse sequence diagram for the new LGE sequence, with the new inversion pulse implemented, showing only two segments.

FIGS. 15A-1, 15A-2, 15B, 15C-1, 15C-2, 15C-3, and 15C-4 illustrate an exemplary embodiment, showing: A: Field map measurements to study the effect of distance on off-resonance induced by an ICD. The image on the left shows how the field map varies in the ACR phantom when an ICD is placed 5 cm from it. The graph on the right shows the field profile along the dotted white line in the field map image. B & C: Progressive reduction of hyper-intensity artifacts using the new wideband inversion pulses in the LGE sequence. B is a gradient recalled echo image (no inversion pulse) showing the phantom setup. C shows LGE images with different inversion pulses: the clinical inversion pulse of BW 1.1 kHz (top left), the new inversion pulses of BW 2.4 kHz (top right) and 3.8 kHz (bottom left). Progressively wider bandwidths decrease the size of the hyper-intensity artifacts in the phantom. In the bottom right image, the 3.8 kHz BW inversion pulse is applied with a frequency shift of 1.5 kHz, which increases the spectral coverage of the pulse to 3.2 kHz. Tubes of Gd-mixed H2O were attached to the ACR phantom, to indicate the location of the phantom boundary. The four tubes doped at different dilution rates of 1:16, 1:32, 1:64 and 1:128, respectively.

DETAILED DESCRIPTION OF THE INVENTION

Unless otherwise noted, terms are to be understood according to conventional usage by those of ordinary skill in the relevant art.

In one aspect, it is hypothesized that the hyper-intensity LGE imaging artifacts are caused by the limited spectral bandwidth of the radiofrequency (RF) inversion pulse that is typically used in LGE MRI. The purpose of the study was to propose and test a modified wideband late gadolinium enhancement (LGE) MRI technique to overcome hyper-intensity image artifacts caused by implanted cardiac devices.

Provided herein are methods and systems for high quality late gadolinium enhancement scar imaging even in the presence of implanted cardiac devices. The technologies disclosed can be widely used by all major manufacturers of clinical MRI systems both in the U.S. and worldwide to eliminate any image quality issues associated with these cardiac devices. In some embodiments, a custom made MRI pulse sequence will be needed, which is a piece of software that controls the MRI system and can be easily implemented.

In one aspect, provided herein is a wideband multi-spectral 3D LGE MRI technique for patients with cardiac devices.

Figures 1, 8A:
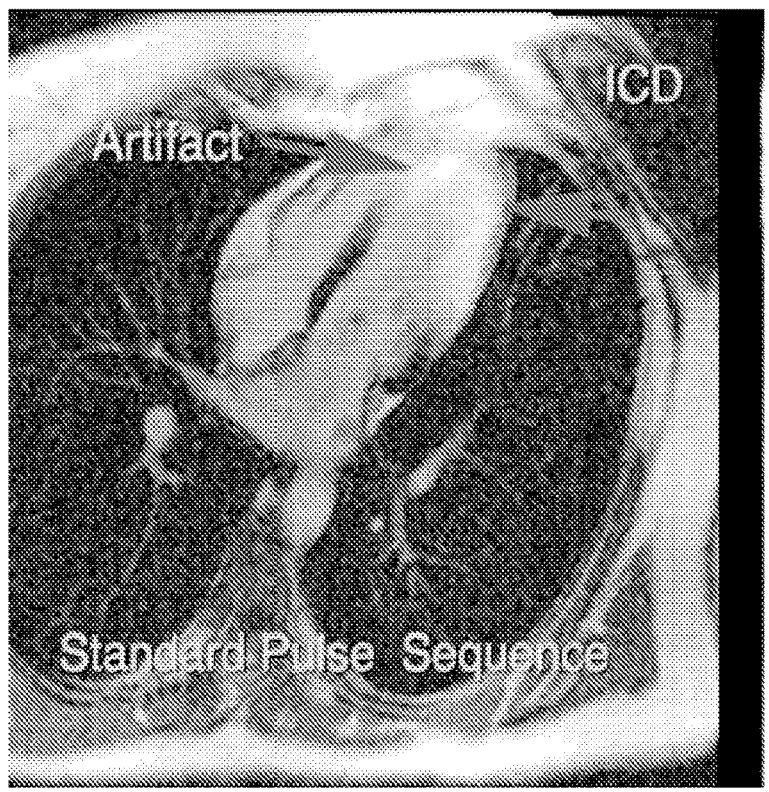
FIGS. 8A-1, 8A-2, 8B-1 and 8B-2 illustrate an exemplary embodiment, showing: 8A-1) a standard LGE MRI pulseuence; and 8A-2) the invented LGE MRI pulse sequence in the presence of an ICD on the chest of the subject. The invented LGE MRI pulse sequence eliminates the signal artifacts (red arrows) that are similar to what are widely reported in the literature on patients with ICDs. Uniform suppression of the myocardium is achieved using the invented pulse sequence. 8B-1) an image collected using a standard pulse sequence from a patient without an ICD; and 8B-2) an image collected using a standard pulse sequence from a patient with an ICD. The comparison illustrates that the presence of the image artifact was associated with the presence of the ICD.
Figures 2, 8A:
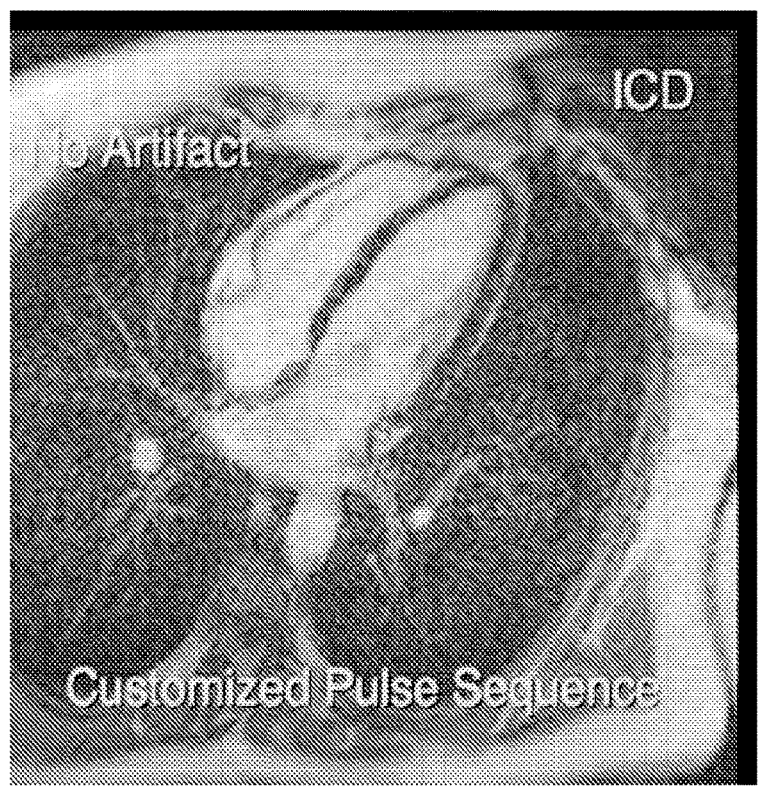

In one aspect, a multi-spectral imaging strategy can be developed. LGE MRI requires the use of a non-selective inversion recovery (IR) pulse to maximize myocardium-scar contrast. In some embodiments, improper inversion of the off-resonance myocardial signal can be due to insufficient spectral bandwidth of the IR pulse is the main reason why LGE MRI fails in the presence of cardiac devices Based on preliminary data (FIGS. 1 & 2). In some embodiments, a comprehensive strategy including novel wideband IR pulse design and/or a multi-spectral imaging strategy can be developed where the LGE IR pulse and potentially the excitation pulse are repeated with different modulation frequencies, thereby providing sufficient spectral coverage to address the off-resonance problem. In some embodiments, aside from spectral coverage problems, other potential issues about signal distortion/pile-up imaging artifacts arising from the cardiac devices can also be addressed using the multi-spectral LGE MRI approach.

In one aspect, an efficient respiratory motion gating strategy can be developed. In some embodiments, the approach is based on a 3D LGE acquisition during free breathing with respiratory motion gating. For LGE MRI, the traditional respiratory navigator (NAV) may fail in presence of cardiac devices because the typical selective NAV-restore IR pulse following the non-selective IR pulse can potentially interfere with the non-selective IR pulse in the LGE sequence due to the presence of strong device-induced off-resonance. The reliability of respiratory navigators in this application is analyzed; and respiratory self-gating as an alternative strategy for reliable respiratory motion gating is investigated.

In another aspect, the developed technique in a small cohort of patients with cardiac devices is tested. In some embodiments, after optimization of the multi-spectral LGE and respiratory motion gating strategies in healthy subjects, patients with ICDs will be tested and the rest will be compared with the conventional LGE MRI sequence in terms of image quality, scar assessment and imaging artifact.

To apply the techniques, one needs to change the spectral coverage of the inversion pulse that is typically used in LGE scans to increase the contrast between scar and normal myocardium. A wider spectral coverage and bandwidth of the inversion pulse will ensure all the myocardium, including the affected off-resonance myocardium, is properly inverted by the inversion pulse. Several possible approaches include: 1) replacing the current inversion pulse with a wideband inversion pulse with a spectral bandwidth wide enough to ensure proper inversion of the affected regions (typically at least 2 kHz or more) and shift the center frequency of the wideband inversion pulse by certain frequency, typically around 500 Hz. The specific frequency shift needed can be adjusted for each patient; 2) replace the current inversion pulse with two or three inversion pulses back to back, each with a different center modulation frequency, as shown in the FIG. 3A; 3) Interleave the on-resonance and off-resonance inversion pulse as shown in the FIG. 3B of the enclosed NIH grant submission. Approaches 2) and 3) above are described in details in the NIH grant. Approach 1) is also proposed in the grant, and the recent preliminary data re-confirms approach 1 to be the likely solution to this problem.

In some embodiments, several modifications will be made based on the current clinical myocardial late gadolinium imaging sequence in order to apply the imaging techniques. For example, the most important modification is to use a wideband inversion pulse to cover the expected the frequency shift causes by the devices. Also, the center frequency of the wideband inversion pulse will need to be shifted 0-1000 Hz depending on the subject to ensure both the on-resonance blood/myocardium and off-resonance myocardium are properly inverted. An alternative approach would be to run 2-3 inversion RF pulses back to back to ensure adequate spectral coverage of the inversion.

Late gadolinium enhancement (LGE) MRI is a powerful tool for myocardial tissue characterization that has been shown to have excellent correlation with histology. It provides excellent contrast between irreversibly injured (scarred) from healthy myocardium by taking advantage of the difference in contrast agent washout kinetics. LGE MRI, along with cardiac cine and myocardial perfusion MRI, plays an important role in diagnosis and treatment of myocardial diseases. Assessment of presence/absence, location, size and pattern of myocardial scar using LGE MRI is not only crucial but also often the only non-invasive means of accurately diagnosing and differentiating various forms non-ischemic cardiomyopathy, including myocarditis, arrhythmogenic right ventricular dysplasia, amyloidosis, and sarcoidosis. LGE MRI also plays an increasing role in guiding treatment of ventricular arrhythmias using catheter ablations, a procedure that is performed on thousands of patients each year in the U.S and worldwide. In the ablation procedure, radiofrequency energy is applied at or around location of myocardial scars and reentrant electric circuits that are responsible for ventricular tachycardia (VT). Therefore, pre-procedural LGE imaging is important for assessing location, size and transmurality of any myocardial scarring and for guiding the ablation procedure.

Cardiac devices, i.e., implantable cardioverter-defibrillators (ICDs) and cardiac pacemakers, are widely used for patients with ventricular arrhythmias. In the current practices, patients with ejection fraction <35% typically receive prophylactic placement of an ICD for primary and secondary prevention of sudden cardiac death, which is the leading cause of mortality in the U.S. accounting for >250,000 deaths per year in the U.S. only. Moreover, approximately 397,000 patients in the U.S. receive a permanent pacemaker each year for various indications. Despite ongoing research efforts on better risk stratification to reduce number of implantations and on improving design of these devices, there will be millions of patients with these devices in the foreseeable future.

LGE MRI is widely accepted as a gold standard for in vivo assessment of myocardial scar. However, its utility in patients with cardiac devices is limited primarily because of safety and imaging artifact issues. ICDs and pacemakers are considered a contraindication to MRI due to the potential heating of the pacing wires caused by the radiofrequency (RF) pulses. In the last decade, the MRI safety aspects have been extensively studied showing that most patients whose rhythms are not device dependent can safely undergo MRI. Despite these positive experiences on the MRI safety aspect, the imaging artifact issue has rarely been addressed, particularly for LGE MRI. The device generator, which is a metal box that is implanted predominantly on the left side of the patient's chest, results in multi-kHz off-resonance on the myocardial tissue and causes significant MR signal artifacts.

These artifacts affect all the sequences in a cardiac MRI exam; and they are especially pronounced in the LGE images and often significantly lower the diagnostic value of the LGE images. MRI of patients with other metallic implants has been investigated and several promising techniques for correcting imaging artifacts have been previously reported. These techniques are developed almost exclusively in the context of imaging patients with orthopedic implants. However, implantable cardiac devices pose unique challenges and issues for LGE MRI compared to orthopedic imaging because: 1) LGE MRI requires contrast manipulation using inversion recovery (IR) pulses; 2) 3D LGE MRI typically requires motion gating and compensation; and 3) In LGE MRI, the range of off-resonance frequencies in the affected myocardium is lower because of a typical 5-7 cm distance from the device generator to the heart.

A metal artifact reduction strategy designed specifically for LGE MRI is highly desirable because many of the cardiomyopathy patients and almost all the VT patients, who have previously implanted devices, will likely benefit from a high-quality LGE scan.

Several new mechanisms and methodologies are provided to address the unique challenges of LGE MRI for patients with previously implanted cardiac devices.

Based on the preliminary results, the improper inversion of the off-resonance myocardial signal due to insufficient spectral coverage of the IR pulse is likely the main reason LGE MRI fails in the presence of cardiac devices. As a result, the affected myocardium, which is most predominantly in regions close to the generator (e.g., anterior and apical left ventricle and out-flow tract) has a much brighter signal than regions that are properly inverted (FIG. 1).

In some embodiments, myocardial scar in these affected regions can be assessed. The presence of this artifact has been previously reported and an urgent need for a metal artifact reduction technique for LGE imaging has been acknowledged; however, there has been no other study that assesses the origin of these commonly seen imaging artifacts or proposes a solution to this problem, despite the potential benefit to a large number of patients. MRI metal artifact reduction is not a new concept in MRI community. Several recent well-designed studies have been reported to significantly reduce a variety of image artifacts, distortion and signal voids caused by metallic implants. Lu et al. proposed the SEMAC technique for multi-slice 2D MRI for patients with metallic implants. Koch et al. developed a multi-spectral 3D imaging method MAVRIC for imaging these patients. More recently, a hybrid MAVRIC-SEMAC method was proposed to combine the strengths of both methods. However, all of these methods are designed for imaging orthopedic implants, but has not been extended and optimized for LGE MRI, which poses unique challenges and issues that requires further investigation. Therefore, the first innovation is the proposed multi-spectral strategy to address this problem. In some embodiments, multiple IR pulses back to back will be used in order to ensure proper inversion of all the spins affected by the device-induced off-resonance. Broadband IR pulses can be developed to achieve wider spectral bandwidth.

In alternative embodiments, interleaving the on-resonance and off-resonance acquisitions between successive heartbeats can be analyzed to provide wider spectral coverage while minimizing any signal distortion and pile-up due to off-resonance.

In current clinical practices, both 2D and 3D LGE MRI sequences are commonly used. Numerous studies have shown the benefits of 3D LGE, which provides higher signal-noise ratio (SNR), higher spatial resolution and shorter overall imaging time. In contrast to 2D LGE, which requires multiple breath-holds for whole heart coverage, 3D LGE typically requires respiratory motion gating to enable scanning during free breathing. Several breath-hold 3D LGE studies have been demonstrated, but at the expense of reduced spatial resolution. Respiratory navigators (NAV) are widely used for respiratory gating, where a 2D pencil beam excitation or a "cross bar" excitation is used to monitor the motion of the diaphragm and to gate the image acquisition. In imaging applications that use a non-selective IR pulse, such as LGE MRI, the NAV volume needs to be "re-inverted" immediately following the non-selective IR pulse to restore the NAV signal. However, in patients with cardiac devices, the NAV is expected to be less reliable because the selective NAV restore pulse may inadvertently excite the spins in the off-resonance myocardium and make it more difficult to reliably calculate the NAV position. More importantly, these regions are likely inverted by the first non-selective IR pulse, but only to be re-inverted back to the positive Z-axis by the immediately following NAV restore pulse. Effectively, the off-resonance myocardium is not inverted, resulting the aforementioned bright-signal artifacts.

Accordingly, in another aspect, the reliability of NAV for LGE MRI in patients with cardiac devices and the potential artifacts generated by the NAV restoration inversion pulse can be studied. In some embodiments, depending on the outcome of the NAV evaluation, respiratory motion self-gating will be analyzed to achieve reliable respiratory motion compensation for the multi-spectral LGE MRI.

Developing Wideband Multi-Spectral Imaging Strategies

In one aspect, a wideband multi-spectral 3D LGE MRI technique for patients with cardiac devices will be developed.

In some embodiments, technical analysis will be performed on phantoms and healthy volunteers to develop and optimize a multi-spectral 3D LGE strategy with reliable respiratory motion gating.

Recent studies suggest that 3D LGE has the potential to increase spatial resolution and shorten the total imaging time while maintaining or improving the image quality compared to 2D LGE. In some embodiments, a multi-spectral LGE sequence will be developed based on a 3D acquisition because it is more compatible with the multi-spectral approach as the phase-encoding gradient in the slice direction will eliminate any signal pile-up problem in the slice direction. In some embodiments, the 3D multi-spectral approach necessitates a free-breathing scan with an effective respiratory motion compensation strategy, which will be discussed more later.

The preliminary results support the hypothesis that the LGE imaging artifacts in patients with cardiac devices is caused by the improperly inverted myocardial signal due to the limited bandwidth of the IR pulse. In some embodiments, 2-3 non-selective IR pulses will be applied instead of a single IR pulse as in the current LGE sequence (e.g., FIG. 3A). The center modulation frequency of the 2-3 IR pulses will be separated by 2-3 kHz, resulting in 2-3 fold increase in the effective bandwidth of the IR pulses. In some embodiments, it is assumed that there is a maximum 2-3 kHz off-resonance in the affected myocardium and thus. In some embodiments, this approach properly invert all the off-resonance myocardial regions.

The IR pulse bandwidth and RF modulation frequency increment will be adjusted depending on the extent of the off-resonance that is typically seen on these patients. In the current standard 2D LGE sequence, a hyperbolic secant pulse of approximately 8-10 ms duration is typically used as the non-selective IR pulse. Therefore, putting 2-3 such IR pulses back-to-back will increase the total duration of the IR pulses to 20-30 ms, which will result in approximately 10 ms longer or shorter TI for different spectral bins. This is not expected to be a significant problem, given the common TI of >200 ms in most LGE scans.

In alternative embodiments, a single wideband IR pulse is designed instead of applying multiple IR pulses to cover the up to 3 kHz off-resonance, where the design can be either adiabatic or non-adiabatic. An adiabatic IR pulse will be designed first by analytically deriving an optimal amplitude/frequency combination based on the given spectral bandwidth (3 kHz). In some embodiments, the adiabatic pulse design will be mainly limited by the B1 amplitude and may slightly increase specific absorption rate (SAR). In some embodiments, a composite broadband IR pulse (non-adiabatic) can also be designed, as successfully demonstrated in the recent saturation pulse design. This may be sensitive to transmit B1 field inhomogeneity but may have decreased SAR. Careful consideration of the transmit B1 field variation may be required for the composite IR pulse. In some embodiments, the wideband inversion pulse has a specific absorption rate (SAR) of 0.2 W/kg or lower, 0.15 W/kg or lower, 0.14 W/kg or lower, 0.13 W/kg or lower, 0.12 W/kg or lower, 0.11 W/kg or lower, 0.10 W/kg or lower, 0.09 W/kg or lower, 0.08 W/kg or lower, 0.07 W/kg or lower, 0.06 W/kg or lower, 0.05 W/kg or lower, 0.04 W/kg or lower, 0.03 W/kg or lower, 0.02 W/kg or lower, or 0.01 W/kg or lower.

A wideband pulse has been successfully designed and implemented into the new LGE MRI sequence to test the hypothesis (e.g., Example 3). In some embodiments, within the sequence, the pulse (e.g., an adiabatic IR) in the standard 2D LGE sequence (~1 kHz bandwidth) is replaced with a wideband pulse (e.g., a wideband adiabatic IR pulse) with 2 kHz bandwidth. In some embodiments, more than one wideband pulses can be used. In some embodiments, more than one wideband adiabatic IR pulses can be used. In some embodiments, the wideband pulse (e.g., an adiabatic IR pulse) has a bandwidth of about 1.2 kHz or higher, 1.5 kHz or higher, 1.8 kHz or higher, 2.0 kHz or higher, 2.2 kHz or higher, 2.4 kHz or higher, 2.6 kHz or higher, 2.8 kHz or higher, 3.0 kHz or higher, 3.5 kHz or higher, 4.0 kHz or higher, 5.0 kHz or higher. In some embodiments, an IR pulse is typically used in LGE as the wideband pulse. In some embodiments, the wideband pulse is a hyperbolic secant inversion pulse. In some embodiments, the wideband pulse is an adiabatic pulse. It be understood that a wideband inversion of any type (adiabatic and non-adiabatic) can be used to correct for the artifacts from the implantable devices. Advantageously, adiabatic pulses have properties that are desirable for LGE MRI.

Further, it will be understood that the concept presented here can be applied to applications other than cardiac MRI in any type of MRI (e.g., for musculoskeletal MRI, or spine MRI) as long as there are inversion pulses used and there is an metal-containing device adjacent to the region of interest. For example, a short tau inversion recover sequence (STIR) is used in musculoskeletal MRI. In some embodiments, the metal-containing device is an implantable device. Examples of metal-containing devices include but are limited to a balloon, a catheter, a pace maker, or an implantable cardio-verter defibrillators.

In some embodiments, the metal-containing device contains one or more metal components.

In some embodiments, an ICD is placed over the chest RF coil of a healthy volunteer to the left side of the heart to mimic the position of the device in a patient. In some embodiments, the standard LGE sequence is performed 15 min after gadolinium contrast injection, followed by the new wideband LGE sequence. In some embodiments, the ICD is subsequently removed and the standard LGE sequence is repeated in the same imaging slice.

Figures 1, 8B:
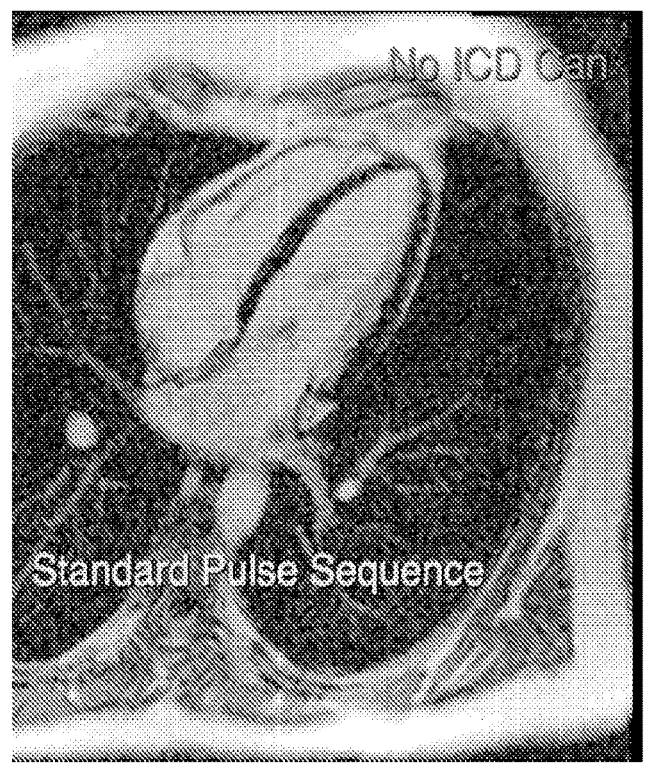
Figures 2, 8B:
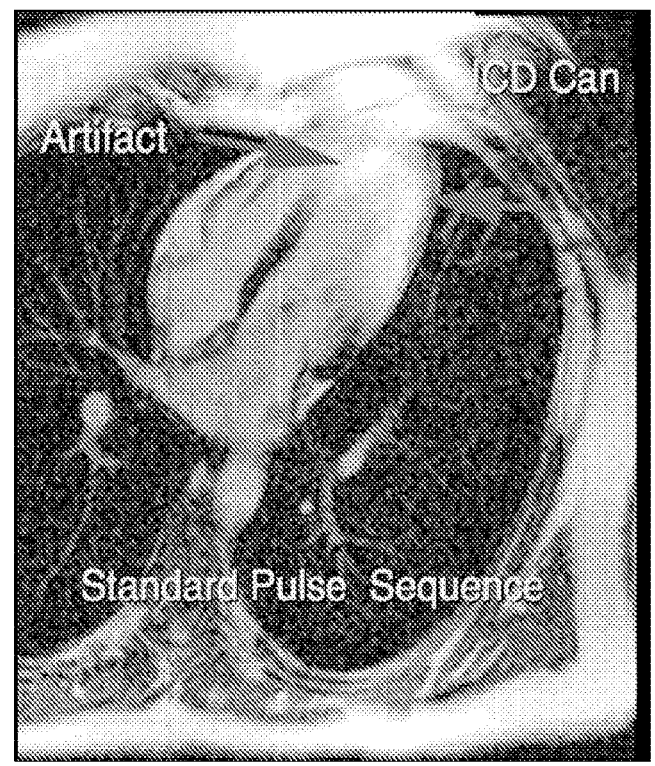

In some embodiments, the wideband LGE sequence can eliminate signal artifacts (e.g., FIG. 1) resulted from conventional sequence analysis, likely due to the wider bandwidth of the pulse (e.g., the IR pulse shown in FIG. 8A). In some embodiments, the wideband LGE sequence can provide uniform myocardium suppression similar to standard LGE in the absence of ICD (e.g., shown in FIG. 8B). In some embodiments, the center frequency of the wideband pulse (e.g., an IR pulse) can be shifted to properly invert both on-resonance and off-resonance myocardium. For example, the center of the wideband pulse (e.g., an IR pulse) can be shifted by 50 Hz or higher, 100 Hz or higher, 150 Hz or higher, 200 Hz or higher, 250 Hz or higher, 300 Hz or higher, 350 Hz or higher, 400 Hz or higher, 450 Hz or higher, 500 Hz or higher, 550 Hz or higher, 600 Hz or higher, 650 Hz or higher, 700 Hz or higher, 750 Hz or higher, 800 Hz or higher, 850 Hz or higher, 900 Hz or higher, 950 Hz or higher, 1000 Hz or higher, 1050 Hz or higher, 1100 Hz or higher, 1150 Hz or higher, 1200 Hz or higher, 1250 Hz or higher, 1300 Hz or higher, 1350 Hz or higher, 1400 Hz or higher, 1450 Hz or higher, and 1500 Hz or higher, 1550 Hz or higher, 1600 Hz or higher, 1650 Hz or higher, 1700 Hz or higher, 1750 Hz or higher, 1800 Hz or higher, 1850 Hz or higher, 1900 Hz or higher, 1950 Hz or higher, 2000 Hz or higher, 2050 Hz or higher, 2100 Hz or higher, 2150 Hz or higher, 2200 Hz or higher, 2250 Hz or higher, 2300 Hz or higher, 2350 Hz or higher, 2400 Hz or higher, 2450 Hz or higher, and 2500 Hz or higher. In some embodiments, the center of the wideband pulse is 800 Hz. In some embodiments, the center of the wideband pulse is 1000 Hz. In some embodiments, the center frequency shift should be adjusted for each individual patient.

Figures 1, 14A:
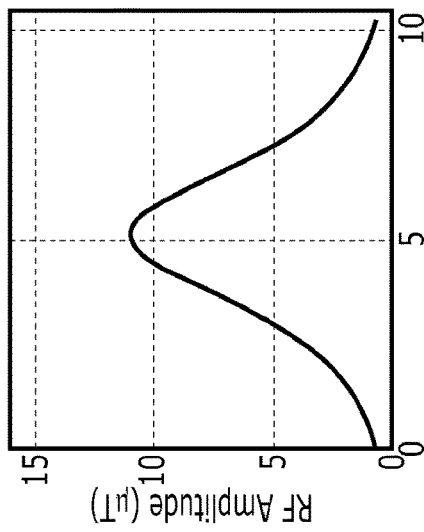
Figures 2, 14A:
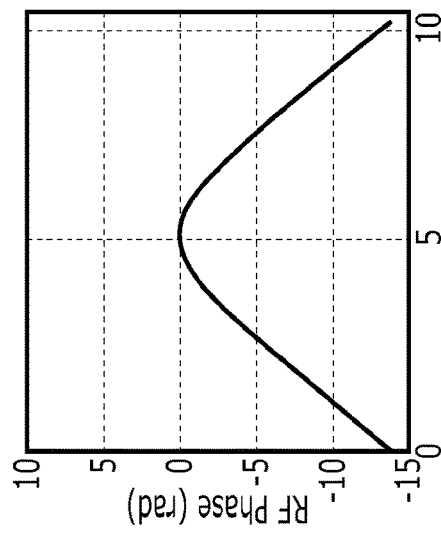
Figures 3, 14A:
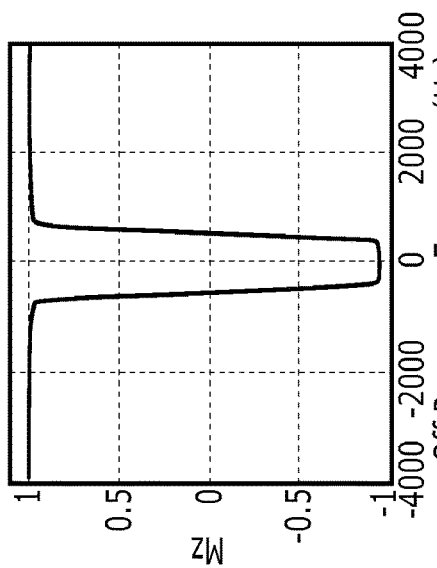
Figures 1, 14B:
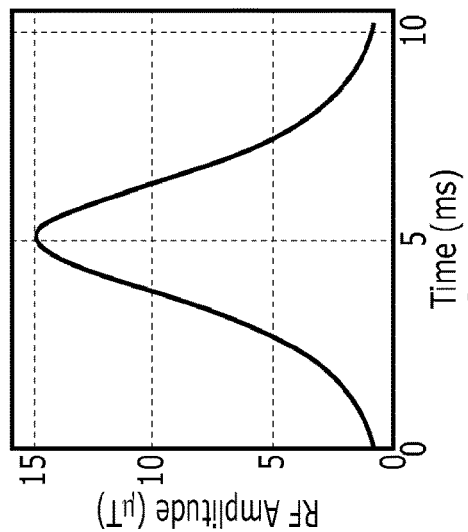
Figures 2, 14B:
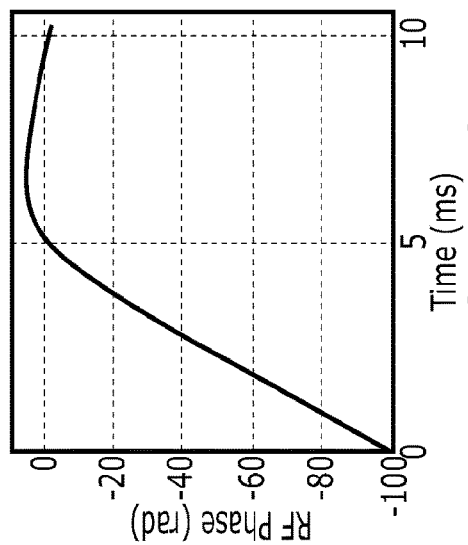
Figures 3, 14B:
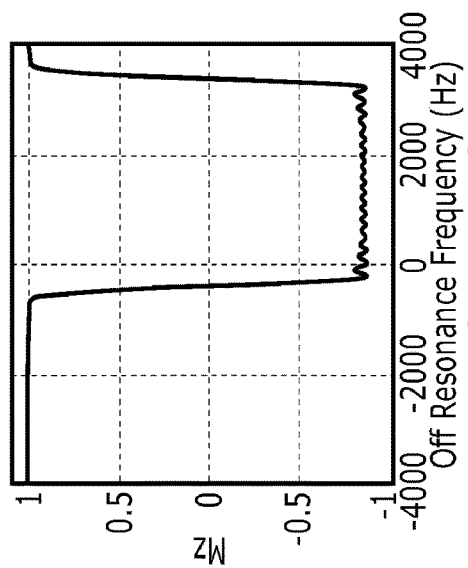

Signal distortion and pile-up in the slice and frequency encoding directions will be minimal given the assumption of less than 3 kHz off-resonance in the affected regions. The preliminary results shown in FIG. 1 support the hypothesis about lack of spectral coverage with the IR pulse, though did not show any evidence of signal distortion/pile-up artifacts. However, in case where significant signal distortion/pile-up will be observed in the multi-spectral approach, an alternative approach will be investigated, as shown in FIG. 3B. There, non-selective excitation and IR pulses will be used to minimize signal distortion/pile-up artifacts and use multi-spectral acquisitions to maintain sufficient spectral coverage. In some embodiments, the on-resonance acquisition will be triggered on every 2 ECG R-R intervals rather than every R-R interval as in most typical 3D LGE scans. In some embodiments, every second R-R interval is used to acquire signal from 2-3 off-resonance spectral bins while the on-resonance spins continue to relax through the second R-R interval.

In the alternative approach, only one single non-selective IR pulse will be used prior to an imaging shot to enable full longitudinal signal relaxation for each spectral bin. For example, it is possible to acquire signals from 2-3 off-resonance spectral bins within the same time as acquisition of one on-resonance spectral bin because the off-resonance acquisitions can be acquired at significantly reduced field of view (FOV) as the affected off-resonance regions is expected to have limited spatial extent. The advantages of this alternative approach include: 1) minimized signal distortion/pile-up due to non-selective excitation; and 2) Each spectral bin will continue to relax through 2 R-R intervals, resulting in better scar-myocardium contrast. The drawback of this alternative approach is that it will prolong the acquisition time and the slab orientation needs to be coronal due to non-selective excitation. In some embodiments, various parallel imaging and/or compressed sensing methods will be used in combination to reduce the imaging time for this alternative strategy.

One important issue of the multi-spectral approach is the spectral overlap between the multi-spectral IR and excitation pulses. In previous multi-spectral imaging studies, the images from multiple spectral bins are combined using square root sum-of-squares. The profile of each individual spectral bin is Gaussian and two adjacent spectral bins have significant overlap in spectral coverage. While this approach might work well for multi-spectral excitation to provide a flat overall spectral response, it might not work well for multi-spectral IR pulses proposed in FIG. 3a, as any spectral overlap will result in spins being inverted by the first IR pulse, but immediately being re-inverted back to +Z axis by the second IR pulse. This will be especially problematic because these spins will show as bright signal because they are effectively not inverted and could be mistaken as myocardial scar enhancement.

This problem can be averted by enlarging the spectral gap between two successive IR pulses and/or by designing IR pulses with more boxcar like spectral profiles. In the alternative embodiment illustrated in FIG. 3b, this issue can be resolved, as the multi-spectral IR pulses are not played successively back-to-back.

Another potential problem is intra-voxel de-phasing. If the off-resonance frequency changes fast enough within a voxel, which has been shown near large metal implants, the signal from the voxel will dephase significantly to a point to cause signal voids. Given the fact that the device generators are typically small and at a distance from the myocardium, this is unlikely going to be a problem. However, an IR turbo spin echo (TSE) sequence will be prepared instead of IR spoiled gradient echo to reduce intra-voxel de-phasing, at an expense of slightly losing scar-myocardium contrast, longer imaging time and an increase in specific absorption rate. All the proposed methodologies in this project will be equally applicable to the TSE sequence.

The proposed multi-spectral 3D LGE sequence will be tested on 15 healthy subjects. The sequence will be performed 10-15 minutes after Gd-DTPA injection. A previously used ICD after generator change will be used. The ICD will be placed on the chest of the healthy subject below the surface coil to produce an off-resonance region in the heart. The ICD and lead will be thermally and electrically isolated from the subject to ensure safety. Although any myocardial scar are not expected in healthy subjects, it is possible to determine whether or not the strategy is working well by confirming presence or absence of the bright signal artifact similar to FIG. 1. In these healthy volunteers, uniform suppression of the myocardial signal indicates successful LGE images. The sequences with several different choices of spectral gap between IR pulses and different spectral profiles of the inversion pulse to best maintain continuous spectral coverage in the IR pulses while minimizing any artifacts caused by spectral overlap will be tested. The respiratory gating strategy will be tested and validated. Further, a strategy to reduce the spatial coverage and/or spatial resolution of the LGE scans in this aim will be used so that the scans can be finished within a single breath-hold.

To assess any signal distortion/pile-up artifacts, a set of non-contrast cardiac cine images will be acquired after removing the cardiac device. The morphology of the LGE images will be compared with the cardiac cine images at the same slice orientation and location to identify any of these kinds of artifacts.

If the resultant sequence has moderate SAR (e.g., >2 W/kg), then consideration will be given to evaluating the potential risk to the patients with implanted ICDs. Related analysis in the evaluation of ICD and pacemaker safety and other related publications will provide guidance during this phase.

Developing a Respiratory Motion Gating Strategy

Figure 1A:
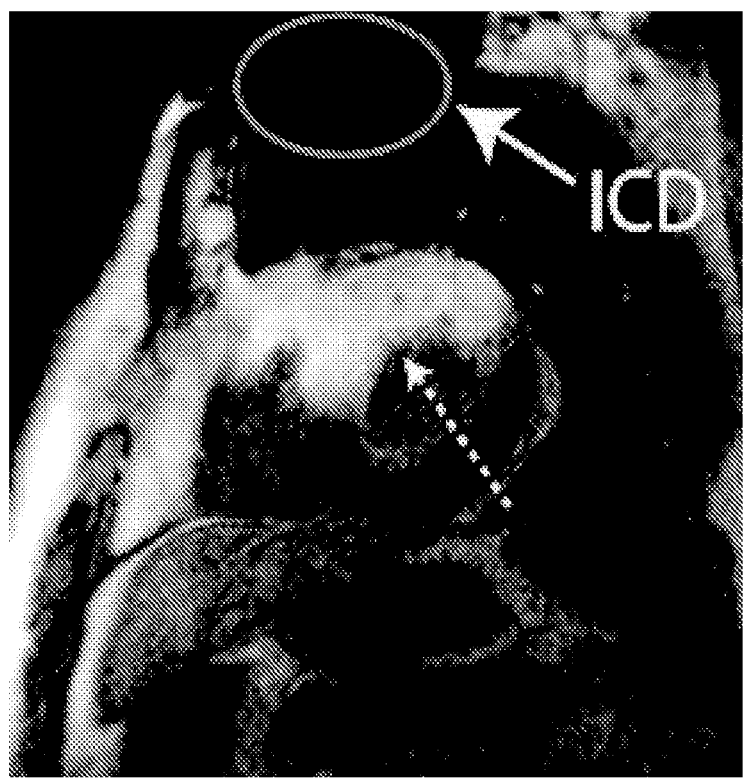
FIGS. 1A and 1B illustrate exemplary images, showing typical LGE images acquired on two patients with ICDs. The ICD generator (solid arrow) causes bright imaging artifacts (dashed arrows) and severely limits assessment of myocardial scar in the affected regions.
Figure 1B:
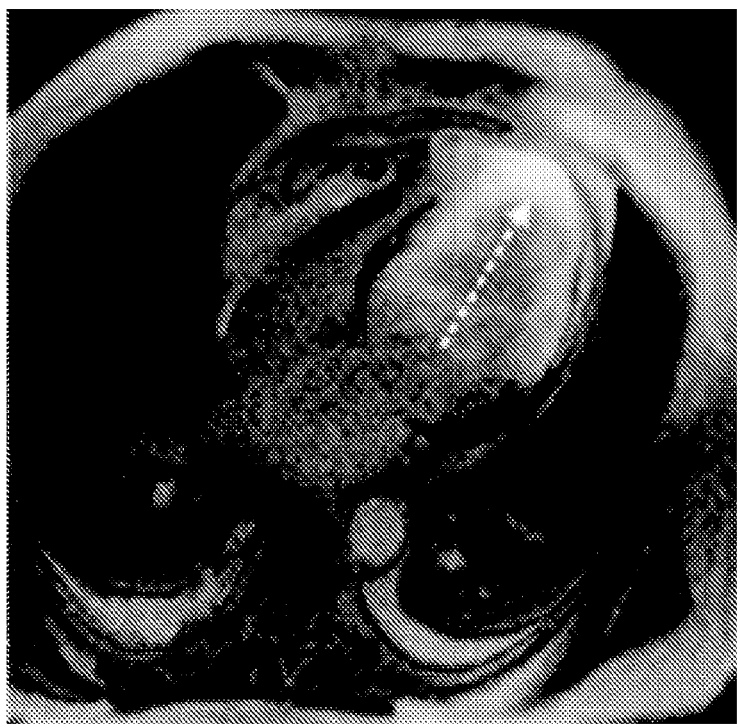
Figure 4:
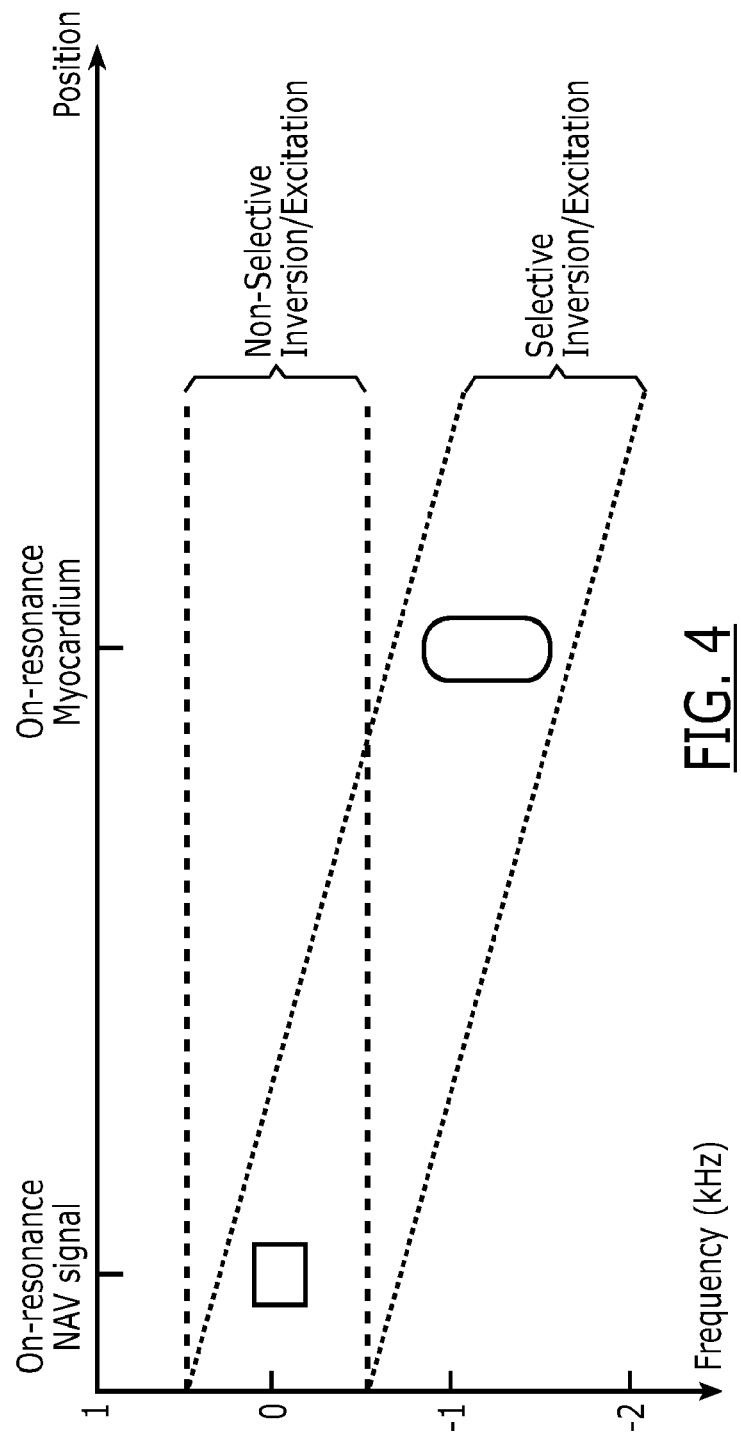
FIG. 4 illustrates potential issues with using navigator (NAV) for the proposed 3D LGE sequence. The selective NAV-restore inversion pulse may inadvertently invert the off-resonance myocardium (shown in red) because it makes the affected myocardium, which would otherwise be outside of the bandwidth of the inversion pulse (shown in blue), fall within the RF bandwidth of the selective NAV restore inversion pulse (red dotted lines) due to presence of a gradient.

In some embodiments, multi-spectral 3D LGE approach necessitates a respiratory motion gating strategy because it may not be feasible within a single breath-hold considering its 3D coverage and multi-spectral nature. Navigators are widely used in 3D cardiac imaging, including coronary artery imaging and LGE imaging, to gate respiratory motion; however, these navigators may not work well on patients with cardiac devices. In a typical free-breathing 3D LGE sequence with navigators, the non-selective IR pulse is immediately followed by a selective IR pulse to restore the magnetization for the navigator. This selective NAV-restore IR pulse is commonly played in the presence of a gradient. Due to the strong off-resonance, the gradient can potentially move the frequency of spins in the off-resonance regions (although far away from the navigator location) into the bandwidth of the NAV-restore IR pulse, causing these regions to be inadvertently inverted back to positive Z direction. This effect is demonstrated in FIG. 4. For reasons as aforementioned, this can be problematic because the potential bright-signal artifact generated by this inadvertent inversion could be mistaken as myocardial scar.

In some embodiments, it will be determined whether navigator is still a viable option for the proposed multi-spectral 3D LGE imaging strategy and, if not, will investigate an alternative respiratory motion gating strategy using respiratory self-gating based on the recent work on respiratory self-gated cardiac cine MRI. In the current approach, the k-space centerline is acquired immediately before each imaging shot and it is used to estimate and gate the respiratory motion. Furthermore and advantageously, multi-channel coil arrays can be used as multiple "sensors" to the motion and can be used jointly to further improve the motion estimation accuracy. Compared to traditional diaphragm navigator, this self-gating approach is not expected to suffer from the aforementioned problems related to the NAV restore IR pulse and it provides a direct estimate of the motion of the heart.

Diaphragm navigators and self-gating strategies will be studied on 15 healthy subjects. In each subject, Gd-DTPA will be injected and images will be acquired 10-15 min after injection with a cardiac device placed on their chest below the surface coil array. Although scarring on healthy volunteers is not expected, the contrast agent is used to create appropriate blood-myocardium contrast. The spatial resolution and spatial coverage of the 3D LGE sequence can be reduced to fit it within a single breath-hold. In some embodiments, the 3D multi-spectral LGE sequence are run twice, with randomized order, one during a breath-hold without navigator and one with the navigator.

In some embodiments, the navigator restore IR pulse causes the aforementioned problem can be determined by comparing these two images and identifying any bright signal enhancement in the heart. In some embodiments, a respiratory self-gated sequence can be developed and run on the same subjects. The resultant images will be compared with the images acquired with breath-hold and navigator. In some embodiments, all three acquisitions (breath-hold, navigator and self-gating) are finished within 60 minutes, within 45 minutes, within 30 minutes, within 25 minutes, within 20 minutes, within 15 minutes, within 10 minutes, within 5 minutes, within 2 minutes. In some embodiments, all three acquisitions are finished within 5 min due to artificially lowered resolution and spatial coverage.

The order in which the acquisitions are performed will be randomized to eliminate any bias in the comparison. The comparison will be performed by two experienced and blinded radiologists, who will assign an image quality score to each of the image sets. The image quality results will be compared using Wilcoxon signed rank test. In some embodiments, a respiratory motion gating strategy is optimized for the multi-spectral 3D LGE sequence.

Applications of Techniques in Patients Implanted Devices

In another aspect, the imaging techniques are applied to a small cohort of patients with ICDs. It will be understood by one of skill in the art that the methods and systems described herein can be applied to any patients with implanted devices that may interfere with or impair medical imaging analysis of these patients, In some embodiments, the optimized 3D multi-spectral LGE sequence are tested on patients with previously installed ICDs who are referred to cardiac MRI. The number of patients tested can be 5 or more, 10 or more, 15 or more, 20 or more, 25 or more, 30 or more, 35 or more, 40 or more, 45 or more, 50 or more, 60 or more, 70 or more, 80 or more, 90 or more, or 100 or more. The imaging will be performed on a 1.5 T MRI system (Avanto, Siemens Medical Solutions, Erlangen, Germany).

In some embodiments, the patient population will include patients who are scheduled to undergo VT catheter ablation and suspected ischemic or non-ischemic cardiomyopathy patients. The model and time of implantation of the ICDs will be verified and evaluated prior to imaging. Appropriate safety guidelines known in the field will be followed, including pre- and post-MRI device interrogation/programming and SAR limits. The patients will first undergo standard pre-contrast cardiac cine MRI with retrospective electrocardiogram (ECG) gating. The cine images will be acquired in short axis and 10-15 slices will be acquired to cover the whole left ventricle. The patients will then undergo the conventional 2D multi-slice breath-hold LGE scan using an inversion recovery spoiled gradient echo sequence and the proposed 3D multi-spectral LGE sequence during free-breathing with optimized respiratory motion gating about 10 minutes after Gd-DTPA injection. Both acquisitions will cover the whole left ventricle. The order in which the sequences are performed will be randomized to eliminate any bias in the comparison. The resultant LGE images will be assessed for presence/absence of imaging artifacts and overall diagnostic image quality on a 1-4 scale by two blinded and experienced radiologists in a consensus reading session. In some embodiments, the multi-spectral LGE images will be presented to the radiologists as separate image sets for each spectral bin and also as a combined image set from all the spectral bins using square root sum-of-squares. In some embodiments, the image quality results will be compared using Wilcoxon signed rank test to determine whether or not each spectral bin images should be combined. The acquired LGE images will also be compared with the cardiac cine images at the same slices to assess presence/absence of any signal pile-up and distortion artifacts in the LGE images. The scar volumes will also be measured on the two LGE images for each patient and the results will be compared using a paired t-test. In some embodiments, the multi-spectral LGE images will be examined to identify any missed scar tissue in regions where bright-signal artifacts exist in the conventional LGE images.

A patient with an implantable cardiac defibrillator was imaged and the myocardial LGE scar images using the current clinical MRI pulse sequence showed significant bright signal artifact in the apical and lateral wall of the left ventricle, which prevented assessment of any scar in this region. The data showed that the bright signal is caused by off-resonance. Subsequently, the center frequency of the current clinical LGE sequence was shifted by 1000 Hz and acquired another image at the same slice orientation and location. As expected, due to the frequency shift, the affected myocardial regions were properly inverted, allowing the radiologist to assess any scar in this region. Thus, in this particular patient, absence of scar in the apical and lateral left ventricular wall was confirmed. See FIGS. 5-8 and Example 3.

Advantageously, the multi-spectral 3D LGE sequence will provide significantly higher image quality and better scar assessment than conventional LGE sequence with minimal signal distortion and pile-up.

REFERENCES

Tian J, Ahmad G, Mesubi O, Jeudy J, Dickfeld T. Three-dimensional delayed-enhanced cardiac MRI reconstructions to guide ventricular tachycardia ablations and assess ablation lesions. Circ Arrhythm Electrophysiol 2012 Apr. 1; 5(2):e31-e35.

Dickfeld T, Tian J, Ahmad G, Jimenez A, Turgeman A, Kuk R, Peters M, Saliaris A, Saba M, Shorofsky S, Jeudy J. MRI-Guided ventricular tachycardia ablation: integration of late gadolinium-enhanced 3D scar in patients with implantable cardioverter-defibrillators. Circ Arrhythm Electrophysiol 2011 April; 4(2):172-184.

Roger V L, Go A S, Lloyd-Jones D M, Benjamin E J, Berry J D, Borden W B, Bravata D M, Dai S, Ford E S, Fox C S, Fullerton H J, Gillespie C, Hailpern S M, Heit J A, Howard V J, Kissela B M, Kittner S J, Lackland D T, Lichtman J H, Lisabeth L D, Makuc D M, Marcus G M, Marelli A, Matchar D B, Moy C S, Mozaffarian D, Mussolino M E, Nichol G, Paynter N P, Soliman E Z, Sorlie P D, Sotoodehnia N, Turan T N, Virani S S, Wong N D, Woo D, Turner M B. Heart disease and stroke statistics—2012 update: a report from the American Heart Association. Circulation 2012 Jan. 3; 125(1):e2-e220.

Nazarian S, Halperin H R. How to perform magnetic resonance imaging on patients with implantable cardiac arrhythmia devices. Heart Rhythm 2009 January; 6(1): 138-143.

Nazarian S, Hansford R, Roguin A, Goldsher D, Zviman M M, Lardo A C, Caffo B S, Frick K D, Kraut M A, Kamel I R, Calkins H, Berger R D, Bluemke D A, Halperin H R. A prospective evaluation of a protocol for magnetic resonance imaging of patients with implanted cardiac devices. Ann Intern Med 2011 Oct. 4; 155(7):415-424.

Sasaki T, Hansford R, Zviman M M, Kolandaivelu A, Bluemke D A, Berger R D, Calkins H, Halperin H R, Nazarian S. Quantitative assessment of artifacts on cardiac magnetic resonance imaging of patients with pacemakers and implantable cardioverter-defibrillators. Circ Cardiovasc Imaging 2011 November; 4(6):662-670.

Naehle C P, Kreuz J, Strach K, Schwab J O, Pingel S, Luechinger R, Fimmers R, Schild H, Thomas D. Safety, feasibility, and diagnostic value of cardiac magnetic resonance imaging in patients with cardiac pacemakers and implantable cardioverters/defibrillators at 1.5 T. Am Heart J 2011 June; 161(6):1096-1105.

Kim R J, Wu E, Rafael A, Chen E L, Parker M A, Simonetti O, Klocke F J, Bonow R O, Judd R M. The use of contrast-enhanced magnetic resonance imaging to identify reversible myocardial dysfunction. N Engl J Med 2000 Nov. 16; 343(20):1445-1453.

Kim R J, Fieno D S, Parrish T B, Harris K, Chen E L, Simonetti O, Bundy J, Finn J P, Klocke F J, Judd R M. Relationship of MRI delayed contrast enhancement to irreversible injury, infarct age, and contractile function. Circulation 1999 Nov. 9; 100(19):1992-2002.

Zipes D P, Wellens H J. Sudden cardiac death. Circulation 1998 Nov. 24; 98(21):2334-2351.

Nazarian S, Roguin A, Zviman M M, Lardo A C, Dickfeld T L, Calkins H, Weiss R G, Berger R D, Bluemke D A, Halperin H R. Clinical utility and safety of a protocol for noncardiac and cardiac magnetic resonance imaging of patients with permanent pacemakers and implantable-cardioverter defibrillators at 1.5 tesla. Circulation 2006 September 19; 114(12):1277-1284.

Sommer T, Naehle C P, Yang A, Zeijlemaker V, Hackenbroch M, Schmiedel A, Meyer C, Strach K, Skowasch D, Vahlhaus C, Litt H, Schild H. Strategy for safe performance of extrathoracic magnetic resonance imaging at 1.5 tesla in the presence of cardiac pacemakers in non-pacemaker-dependent patients: a prospective study with 115 examinations. Circulation 2006 Sep. 19; 114(12): 1285-1292.

Koch K M, Lorbiecki J E, Hinks R S, King K F. A multispectral three-dimensional acquisition technique for imaging near metal implants. Magn Reson Med 2009 February; 61(2):381-390.

Lu W, Pauly K B, Gold G E, Pauly J M, Hargreaves B A. SEMAC: Slice Encoding for Metal Artifact Correction in MRI. Magn Reson Med 2009 July; 62(1):66-76.

Koch K M, Brau A C, Chen W, Gold G E, Hargreaves B A, Koff M, McKinnon G C, Potter H G, King K F. Imaging near metal with a MAVRIC-SEMAC hybrid. Magn Reson Med 2011 January; 65(1):71-82.

Peters D C, Appelbaum E A, Nezafat R, Dokhan B, Han Y, Kissinger K V, Goddu B, Manning W J. Left ventricular infarct size, peri-infarct zone, and papillary scar measurements: A comparison of high-resolution 3D and conventional 2D late gadolinium enhancement cardiac M R. J Magn Reson Imaging 2009 October; 30(4):794-800.

Nguyen T D, Spincemaille P, Weinsaft J W, Ho B Y, Cham M D, Prince M R, Wang Y. A fast navigator-gated 3D sequence for delayed enhancement MRI of the myocardium: comparison with breathhold 2D imaging. J Magn Reson Imaging 2008 April; 27(4):802-808.

Foo T K, Stanley D W, Castillo E, Rochitte C E, Wang Y, Lima J A, Bluemke D A, Wu K C. Myocardial viability: breath-hold 3D M R imaging of delayed hyperenhancement with variable sampling in time. Radiology 2004 March; 230(3):845-851.

Goetti R, Kozerke S, Donati O F, Surder D, Stolzmann P, Kaufmann P A, Luscher T F, Corti R, Manka R. Acute, subacute, and chronic myocardial infarction: quantitative comparison of 2D and 3D late gadolinium enhancement M R imaging. Radiology 2011 June; 259(3):704-711.

Weber O M, Martin A J, Higgins C B. Whole-heart steady-state free precession coronary artery magnetic resonance angiography. Magn Reson Med 2003 December; 50(6):1223-1228.

Nguyen T D, Spincemaille P, Cham M D, Weinsaft J W, Prince M R, Wang Y. Free-breathing 3-dimensional steady-state free precession coronary magnetic resonance angiography: comparison of four navigator gating techniques. Magn Reson Imaging 2009 July; 27(6):807-814.

Hu P, Hong S, Moghari M H, Goddu B, Goepfert L, Kissinger K V, Hauser T H, Manning W J, Nezafat R. Motion correction using coil arrays (MOCCA) for free-breathing cardiac cine MRI. Magn Reson Med 2011 August; 66(2):467-475.

Hargreaves B A, Worters P W, Pauly K B, Pauly J M, Koch K M, Gold G E. Metal-induced artifacts in MRI. AJR Am J Roentgenol 2011 September; 197(3):547-555.

Hu P, Chan J, Ngo L H, Smink J, Goddu B, Kissinger K V, Goepfert L, Hauser T H, Rofsky N M, Manning W J, Nezafat R. Contrast-enhanced whole-heart coronary MRI with bolus infusion of gadobenate dimeglumine at 1.5 T. Magn Reson Med 2011 February; 65(2):392-398.

Rosenfeld D, Zur Y. A new adiabatic inversion pulse. Magn Reson Med 1996 July; 36(1):124-136.

Sung K, Nayak K S. Design and use of tailored hard-pulse trains for uniformed saturation of myocardium at 3 Tesla. Magn Reson Med 2008 October; 60(4):997-1002.

Akcakaya M, Hu P, Chuang M L, Hauser T H, Ngo L H, Manning W J, Tarokh V, Nezafat R. Accelerated noncontrast-enhanced pulmonary vein MRA with distributed compressed sensing. J Magn Reson Imaging 2011 May; 33(5):1248-1255.

Akcakaya M, Nam S, Hu P, Moghari M H, Ngo L H, Tarokh V, Manning W J, Nezafat R. Compressed sensing with wavelet domain dependencies for coronary MRI: a retrospective study. IEEE Trans Med Imaging 2011 May; 30(5):1090-1099.

Lustig M, Donoho D, Pauly J M. Sparse MRI: The application of compressed sensing for rapid M R imaging. Magn Reson Med 2007 December; 58(6):1182-1195.

Gao H, Rapacchi S, Wang D, Moriarty J, Meehan C, Sayre J, Laub G, Finn J P, Hu P. Compressed sensing using prior rank, intensity and sparsity model (PRISM): applications in cardiac cine MRI. Proc Intl Soc Mag Reson Med 20 (2012); Melbourne, Australia 2012. p. 2242.

Worters P W, Sung K, Stevens K J, Koch K M, Hargreaves B A. Compressed sensing multi-spectral imaging of the post-operative spine. Proc Intl Soc Mag Reson Med 20 (2012); Melbourne, Australia 2012. p. 6.

Simonetti O P, Kim R J, Fieno D S, Hillenbrand H B, Wu E, Bundy J M, Finn J P, Judd R M. An improved M R imaging technique for the visualization of myocardial infarction. Radiology 2001 January; 218(1):215-23.

Langman D A, Finn J P, Ennis D B. Abandoned pacemaker leads are a potential risk for patients undergoing MRI. Pacing Clin Electrophysiol 2011 September; 34(9):1051-1053.

Langman D A, Goldberg I B, Finn J P, Ennis D B. Pacemaker lead tip heating in abandoned and pacemaker-attached leads at 1.5 Tesla MRI. J Magn Reson Imaging 2011 February; 33(2):426-431.

Langman D A, Goldberg I B, Judy J, Paul Finn J, Ennis D B. The dependence of radiofrequency induced pacemaker lead tip heating on the electrical conductivity of the medium at the lead tip. Magn Reson Med 2011 Dec. 28.

Roguin A, Zviman M M, Meininger G R, Rodrigues E R, Dickfeld T M, Bluemke D A, Lardo A, Berger R D, Calkins H, Halperin H R. Modern pacemaker and implantable cardioverter/defibrillator systems can be magnetic resonance imaging safe: in vitro and in vivo assessment of safety and function at 1.5 T. Circulation 2004 Aug. 3; 110(5):475-482.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Imaging Patients with ICDs

Images from 6 VT patients with ICDs who underwent cardiac MRI were examined. FIG. 1 shows representative LGE images acquired in two of these patients, where the anterior and apical regions of the left ventricle show bright signal intensity that makes it impossible to assess any myocardial scar in these regions. Although efforts were taken to reduce these artifacts at the time of scanning, the LGE images of the 6 patients were either totally nondiagnostic or the diagnostic value was severely limited by the presence of the bright artifacts. The observations of the artifacts were consistent with that of previous studies.

The conventional LGE sequence uses a non-selective adiabatic IR pulse typically with an inversion time (TI) of 200-300 ms to null the healthy myocardium. In the presence of a metallic object, the regions well beyond the physical boundary of the metallic object will be affected by strong off-resonance, often reaching up to 15-20 kHz at 1.5 T. Given the small size of the cardiac device generator (typically <3-5 cm) and the distance of the generator to the heart (typically approximately 5-7 cm), the off-resonance in the affected myocardial regions (mostly anterior and apical left ventricle) is expected to be within 2-3 kHz. However, the bandwidth of an adiabatic IR pulse is typically less than 1 kHz, which suggests that the bright-signal imaging artifacts are caused by regions of affected myocardium not being properly inverted. This strong off-resonance can also affect the excitation (imaging) pulse, but in a different fashion as the excitation pulse typically has wider bandwidth than the IR pulse. This explains the imaging artifacts shown in FIG. 1. The bright signals in the off-resonance region show that a signal is excited by the excitation pulse but not properly inverted by the IR pulse. Although the off-resonance spins are excited in a 2D LGE sequence, there is a potential for a signal pile-up in the slice-encoding direction, where off-resonance spins outside of the prescribed imaging slice will be excited (due to presence of slice-encoding gradient) and encoded as signal from within the slice. In addition, the off-resonance will also cause a shift and potentially distortion in the frequency-encoding direction. In the context of LGE, these effects translate to potentially mis-encoded scar locations. This effect has been well described in previous publications. The magnitude of the signal pile-up and distortion effects depends on the amount of off-resonance and the image acquisition strategies used (e.g., 2D vs. 3D acquisitions) and are difficult to separate because both result in geometric distortion, signal loss and signal pile-up effects. The typical in vivo LGE images shown in FIG. 1 did not enable us to make a conclusion on the presence/absence of the signal pile-up problem and this issue will be further studied in the project.

Example 2

Development of Strategies for Multi-Spectral Imaging

A phantom study was performed on a 1.5 T MRI system (Avanto, Siemens). A pacemaker (PM) that was previously implanted in a patient was placed approximately 7 cm to the right of a phantom (shown in red circle in FIG. 2). LGE images were acquired using the clinical 2D IR spoiled gradient echo LGE sequence with TI=200 ms.

The same LGE sequence was repeated with the exception that the modulation frequency of the inversion and excitation RF pulses was manually shifted up to ±1 kHz. On-resonance LGE MRI without the IR pulse was also performed. The same experiments were repeated after removing the pacemaker.

Results are shown in FIG. 2. In the on-resonance image with pacemaker placed, the part of the phantom affected by the off-resonance is bright (dashed arrow) and the "myocardium" is suppressed, a similar observation as in the in vivo example shown in FIG. 1. The images with −1000 Hz RF frequency shift shows the affected region as dark and remote region as bright, presumably because the affected region is now inverted while the remote on-resonance region is not inverted because of the RF modulation frequency shift. This data supports that inadequate spectral coverage of the IR pulse in LGE causes the bright imaging artifact. The phantom signal is homogenous in the "without IR" image, demonstrating the artifact is mainly caused by improper inversion. Slight signal distortion is observed in the images with pacemaker placed. An ICD generator is usually larger than a pacemaker, and therefore is expected to generate large off-resonance and more imaging artifacts.

Example 3

Case Study

Figure 5A:
FIGS. 5A and 5B illustrate an exemplary embodiment, demonstrating a comparison of myocardial scar images acquired using A) traditional LGE MRI sequence and B) a frequency-shifted LGE MRI sequence. In the traditional LGE MRI, the apical and anterior left ventricular wall is not properly inverted, preventing accurate myocardial scar assessment in these regions. The frequency shift enables proper inversion of these regions and enabled assessment of scars in the apical and anterior LV wall (arrows). This data provides evidence that the commonly seen bright signal artifacts shown in a) is indeed due to improper inversion of the affected myocardial regions, not due to presence of actual scar.

Methods: Recent literature shows that cardiac MRI, including LGE MRI, can be safely performed for patients with cardiac devices. However, the current LGE MRI sequence suffers from bright signal artifacts as shown in FIG. 5A. These image artifacts prevents assessment of presence or absence of myocardial scar in the affected regions, which are typically apical and anterior left ventricular wall for a device implanted on the left side of the heart. Although these image artifacts were previously reported, there has been no solution proposed for this problem. It was hypothesized that the bright signal artifact is caused by the affected myocardium not being properly inverted by the non-selective inversion pulse that is typically played in a traditional LGE MRI pulse sequence due to the limited spectral bandwidth of the inversion radiofrequency pulse.

To preliminarily test the hypothesis, a patient with an implantable cardiac defibrillator was imaged twice. Firstly, the traditional LGE MRI sequence was used. The center modulation frequency of the LGE MRI sequence was then shifted and the scan was repeated. To properly invert off-resonance myocardium, a wideband adiabatic inversion pulse with 2 kHz of spectral bandwidth was designed, which is subsequently implemented in the LGE MRI sequence to replace the original inversion pulse. The two LGE MRI sequence, one with the traditional inversion pulse and one with the wideband inversion, were used to image an ACR (American College of Radiology) water phantom with an implantable cardiac defibrillator (ICD) placed approximately 10 cm away from the edge of the phantom. A simulated ECG was used to gate the MRI sequence in the absence of an ECG signal. The inversion time (TI) was empirically decided to be the TI that suppresses the signal from the phantom best. In another experiment, a healthy volunteer was recruited who underwent LGE MRI approximately 10 min after Gadolinium contrast injection. An ICD was placed over the chest of the subject to the left of the heart. With the ICD in place, the current standard LGE MRI sequence and the custom made LGE MRI sequence were performed. In the custom made LGE MRI sequence, the non-selective adiabatic inversion pulse with 2 kHz of spectral bandwidth was used in place of the traditional non-selective adiabatic pulse that is typically used in standard LGE MRI sequences. The center modulation frequency of the 2 kHz bandwidth inversion pulse was shifted 800 Hz in this experiment. Subsequently, the ICD was removed and the standard LGE MRI sequence was repeated. It is noted that the spectral bandwidth and center frequency shift of the new inversion pulse can be varied and still work well as long as the combination of spectral bandwidth and frequency shift enable uniform inversion of myocardium over the range of resonance frequencies that is experience by the myocardium in the presence of cardiac devices.

Figure 5B:
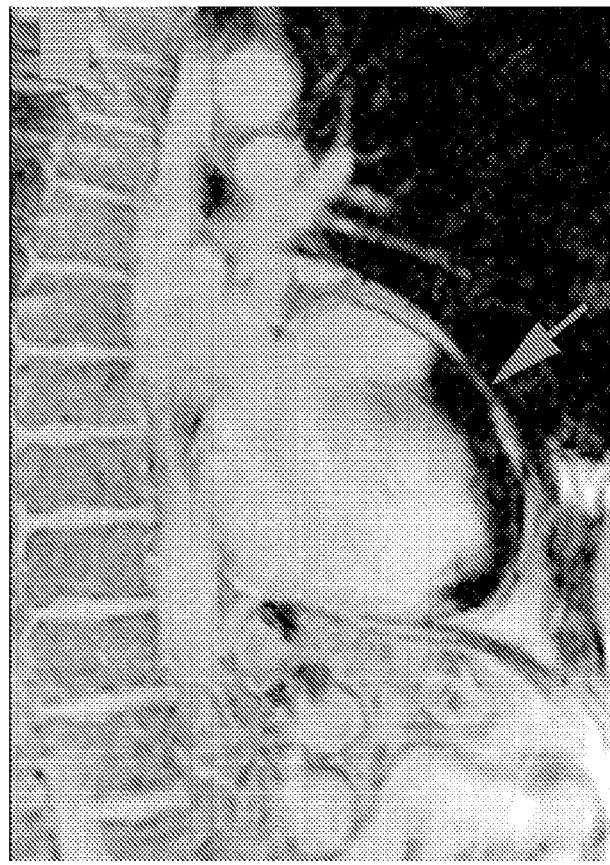
Figure 6:
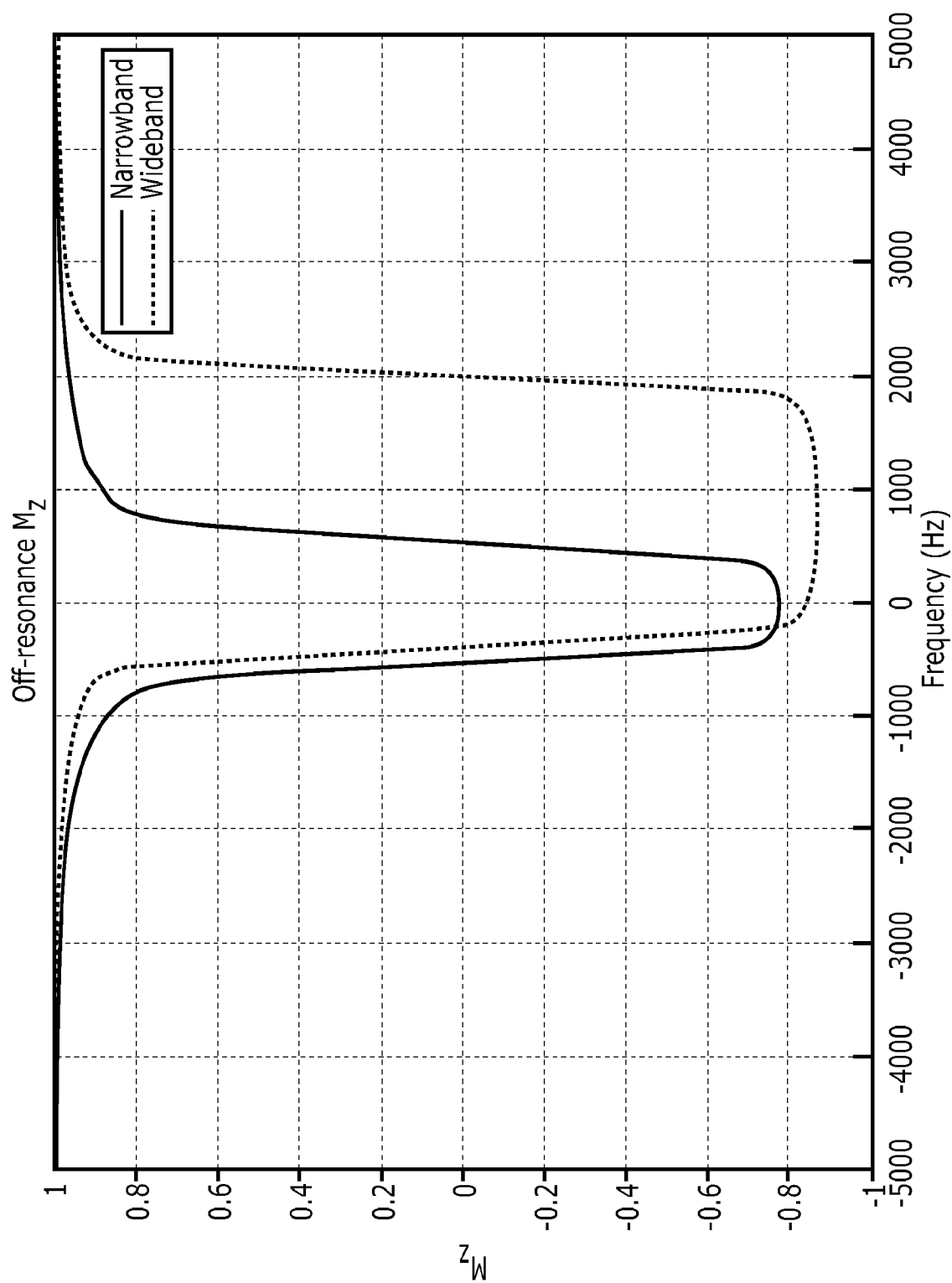
FIG. 6 illustrates an exemplary embodiment. The wideband adiabatic inversion pulse (shown in red) has 2 kHz bandwidth, and is significantly wider in spectral bandwidth than the inversion pulse that is currently used clinically (shown in blue). Other designs of the wideband pulse are possible to obtain a wider bandwidth. To apply a wideband inversion pulse in LGE MRI for patients with cardiac devices, the center frequency of the RF pulse may need to be shifted certain frequency to make sure both myocardial regions affected and non-affected by the device will be properly inverted. As an example, the wideband pulse center frequency is shifted by approximately 800 Hz.

Results: FIGS. 5A and 5B show an example comparison of the traditional LGE MRI and the LGE MRI with a center frequency shift of 1000 Hz. In traditional LGE MRI, the region of the water phantom close to the ICD was bright because its resonance frequency is outside of the spectral bandwidth of the inversion pulse used and is hence not inverted. The region far away from the ICD are properly inverted and shows as dark. In the frequency shifted LGE MRI, the region close to the ICD is inverted and shows as dark, while the region far away from the ICD falls outside of the spectral bandwidth of the frequency-shift inversion pulse and shows as bright. In this particular patient, by shifting the frequency, it was confirmed that the apical and lateral left ventricular wall (shown in red arrows) did not have myocardial scar, a statement that would be impossible to make based on the traditional LGE MRI image. FIG. 6 shows a comparison between the adiabatic inversion pulse that is used in traditional LGE MRI images and the wideband adiabatic inversion pulse. To obtain best results, the center frequency of the wideband may need to be shifted 500-1000 Hz to accommodate the range of myocardial off-resonance of each patient. In FIG. 6, the center frequency of the wideband pulse was shifted 800 Hz. FIG. 7 shows a comparison of LGE MRI images acquired on the phantom using both traditional LGE MRI and the LGE MRI with wideband inversion. Due to the use of wideband, the regions close to the ICD is nearly fully inverted, resulting a uniformly suppressed water phantom due to inversion.

FIG. 8A shows a comparison between the standard and the custom made LGE MRI sequence with the presence of ICD on the healthy volunteer. The bright signal artifacts (red arrows) were eliminated in the custom made sequence due to the wider spectral bandwidth of the inversion pulse.

As shown in FIG. 8A, the ICD caused bright signal artifacts similar to the patient LGE images in FIG. 1. In this patient, the wideband LGE sequence (FIG. 8A) eliminated these bright signal artifacts, likely due to the wider bandwidth of the IR pulse, and was able to provide uniform myocardium suppression similar to standard LGE in the absence of ICD shown in FIG. 8B. In this experiment, the center frequency of the wideband IR pulse was shifted 800 Hz to properly invert both on-resonance and off-resonance myocardium.

Conclusion: The technique eliminated or reduced the LGE MRI imaging artifacts for patients with cardiac devices and can be widely applicable and to lead to immediate benefits for the large population of patients with cardiac devices who need an cardiac MRI.

Example 4

Additional Case Study on Patients with Implanted Cardiac Devices

The LGE MRI technique has been modified for patients with implanted cardiac devices using a wideband inversion pulse. The wideband LGE technique removes the hyper-intensity artifacts that are typically seen with conventional LGE MRI.

Purpose: To propose and test a modified wideband late gadolinium enhancement (LGE) MRI technique to overcome hyper-intensity image artifacts caused by implanted cardiac devices.

Materials and Methods: Written informed consent was obtained from all participants, and the HIPAA-compliant protocol was approved by the Institutional Review Board. Phantom and healthy volunteer studies were performed to test the hypothesis that the hyper-intensity image artifacts that are typically observed on LGE images of patients with implanted cardiac devices are caused by insufficient inversion of the affected myocardial signal. The conventional LGE MRI pulse sequence was modified by replacing the non-selective inversion pulse with a wideband inversion pulse. The modified LGE sequence, along with the conventional LGE, was evaluated on 12 patients with implantable cardioverter defibrillators who were referred for cardiac MRI.

Results: The ICD causes 2-6 kHz in frequency shift at locations 5-10 cm away from the device. This off-resonance falls outside of the typical spectral bandwidth of the non-selective inversion pulse used in conventional LGE, which results in the hyper-intensity image artifact. In 10 out of the 12 patients, the conventional LGE technique produced severe, uninterpretable hyper-intensity image artifacts in the anterior and lateral left ventricular wall, which were eliminated by the wideband LGE sequence, thereby enabling confident evaluation of myocardial viability.

Conclusion: The modified wideband LGE MRI technique eliminates the hyper-intensity image artifacts seen in patients with cardiac devices. The technique can enable LGE MRI in patients with cardiac devices who would otherwise be inaccessible to diagnosis.

Materials and Methods

Written informed consent was obtained from all participants, and the HIPAA-compliant protocol was approved by the Institutional Review Board.

Pulse Sequence Design

The conventional LGE scan consists of an inversion prepared 2D or 3D segmented gradient echo sequence. The subject received gadolinium contrast injection about 15 minutes prior to LGE. An inversion time of 250-300 ms is then used to nullify the signal from the healthy myocardium, which has a Gd-enhanced T1 of 381±58 ms. The RF inversion pulse in the conventional LGE sequence on the 1.5 T scanners (Avanto™, Siemens Medical Systems, Malvern, Pa.) is a hyperbolic secant (HS) adiabatic inversion pulse. Although the inversion pulse is spatially non-selective, it has a spectral bandwidth of 1.1 kHz. For a cardiac device generator that is typically 5-10 cm away from the patient's heart, the expected resonance offset of the myocardium is in the 2-6 kHz range (e.g., FIG. 15A), well outside the bandwidth of the inversion pulse currently used. Consequently, the affected myocardium is not properly inverted (nulled) and is typically hyper-intense, undermining appropriate diagnostic interpretation.

To address this issue, design and implement a wideband adiabatic inversion pulse was designed and implemented to ensure proper inversion of the myocardium affected by the device generator. This inversion pulse was implemented into the existing 2D inversion recovery LGE sequence, replacing the conventional inversion pulse. The design and testing of the wideband inversion pulse using computer simulations and phantom studies are described in the Online Appendix.

In Vivo Study

To demonstrate the benefits of the modified wideband LGE pulse sequence, a healthy volunteer was included in the study. The volunteer received an IV injection of gadolinium contrast ("Magnevist", 0.15 mmol/kg, Bayer-Schering, Germany) approximately 15 minutes prior to LGE MRI. A Look-Locker TI scout sequence was used to identify the appropriate inversion time for suppression of left myocardial signal. Although myocardial scars in the volunteer was not expected, the purpose was to determine whether or not it was possible to mitigate the hyper-intensity artifact which would occur with the conventional LGE sequence. In the healthy volunteer, therefore, uniform suppression of the myocardial signal would indicate successful LGE imaging. Both the conventional and the modified LGE sequence were used to acquire images of the heart in the horizontal long axis (HLA) plane. Images were acquired with the ICD attached to the body coil, close to the infraclavicular prepectoral area of the left shoulder (which is the most common site of ICD implantation in patients). The images were immediately reacquired after removal of the ICD. Sequence parameters include: TR/TE=4.1/1.5 ms, FOV=360 mm, FA=25°, readout bandwidth=500 Hz/pixel, slice thickness=8 mm, resolution=1.4×1.9 mm, TI=250-400 ms.

Subsequent to the healthy volunteer study, 12 patients with previously implanted ICDs whose heart rhythm was not device dependent were included in this study. All patients had been referred for a cardiac MRI examination for the purpose of pre-VT ablation evaluation of left ventricular scar. The ICDs implanted in the patients included the following models: Medtronic Protecta VR, Biotronik Lumax 540 DR-T, St. Jude Medical Fortify DR, Boston Scientific TELIGEN E110 DR & INCEPTA E163. The cardiac MR exam included scans of the heart using the conventional LGE sequence. Images in which hyper-intensity artifacts appeared were immediately reacquired using the modified wideband LGE sequence. Since the wideband LGE immediately follows the conventional LGE, the same TI was used for both sequences for a given imaging slice. The TI was increased about 10 ms for every 1-2 minutes to maintain adequate suppression of the myocardium. A Look-Locker TI scout was used as needed to ensure accurate TI. To determine the optimal frequency offset of the inversion pulse, the wideband LGE of the first 2D slice was acquired three times with zero, positive and negative frequency offsets, respectively. Positive and negative offsets were in the range of 0-2500 Hz. In some embodiments, the offsets are more than 2500 Hz. For example, a positive or negative offset can be 50 Hz or higher, 100 Hz or higher, 150 Hz or higher, 200 Hz or higher, 250 Hz or higher, 300 Hz or higher, 350 Hz or higher, 400 Hz or higher, 450 Hz or higher, 500 Hz or higher, 550 Hz or higher, 600 Hz or higher, 650 Hz or higher, 700 Hz or higher, 750 Hz or higher, 800 Hz or higher, 850 Hz or higher, 900 Hz or higher, 950 Hz or higher, 1000 Hz or higher, 1050 Hz or higher, 1100 Hz or higher, 1150 Hz or higher, 1200 Hz or higher, 1250 Hz or higher, 1300 Hz or higher, 1350 Hz or higher, 1400 Hz or higher, 1450 Hz or higher, and 1500 Hz or higher, 1550 Hz or higher, 1600 Hz or higher, 1650 Hz or higher, 1700 Hz or higher, 1750 Hz or higher, 1800 Hz or higher, 1850 Hz or higher, 1900 Hz or higher, 1950 Hz or higher, 2000 Hz or higher, 2050 Hz or higher, 2100 Hz or higher, 2150 Hz or higher, 2200 Hz or higher, 2250 Hz or higher, 2300 Hz or higher, 2350 Hz or higher, 2400 Hz or higher, 2450 Hz or higher, and 2500 Hz or higher. The frequency offset that resulted in artifact free image was chosen and used in any subsequent slices. Therefore, a total of 3 breath-hold wideband LGE acquisitions were required to determine the frequency offset in each patient. All patients were monitored by ECG telemetry and peripheral pulse oximetry. The ICDs were interrogated and reprogrammed as appropriate pre- and post-MRI, according to the guidelines by the European Society of Cardiology and the literature. An electrophysiologist, a radiologist, an advanced cardiac life support (CLS)-certified personnel, and a cardiac device programmer were present during the scans. The specific absorption rate (SAR) of the LGE sequences was limited to below 2 W/kg of tissue to ensure scan safety. All clinical images were reviewed by a board certified radiologist (J.P.F.) with more than 20 years of experience in cardiac MRI.

Results

Computer simulation and phantom test results are described in the Online Appendix. Phantom studies demonstrated that the wideband inversion pulse can successfully invert a wider range of off-resonance spins than the conventional inversion pulse.

Figure 9A:
FIGS. 9A, 9B, and 9C illustrate an exemplary embodiment, showing LGE images from a healthy volunteer, acquired 15 minutes post Gd injection. Approximate location of the ICD is indicated with the dotted ellipse. A: HLA image without ICD using the conventional LGE sequence. B: HLA image with ICD attached near shoulder, using the conventional LGE sequence. Hyper-intensity artifacts were formed at the apex (indicated by the arrow). C: HLA image with ICD attached near shoulder using the proposed wideband LGE sequence. Hyper-intensity artifact was no longer present.
Figure 9B:
Figure 9C:

FIG. 9 shows images from the healthy volunteer. Hyper-intensity artifacts were formed at the apical region of the LV in the presence of the ICD using the conventional LGE (FIG. 9B) and the artifacts were completely removed in the wideband LGE (FIG. 9C). The wideband LGE did not introduce additional image artifacts when compared with conventional LGE in the absence of ICD as shown in FIG. 9A.

All patients were at sinus rhythm during MRI, except 3 patients who had sporadic premature ventricular contractions. When arrhythmia occurred during acquisition, the image was re-acquired. Of the 12 patients in this study, 10 showed various degrees of hyper-intensity artifact and 2 patients did not show any artifact using the conventional LGE sequence because the ICD was at a greater distance away from the heart. One of these two patients had an ICD implanted on the right side. All the artifacts were completely resolved using the modified wideband LGE sequence. The optimal frequency offset of the wideband inversion pulse was successfully determined in all of the 10 patients.

Figure 10B:
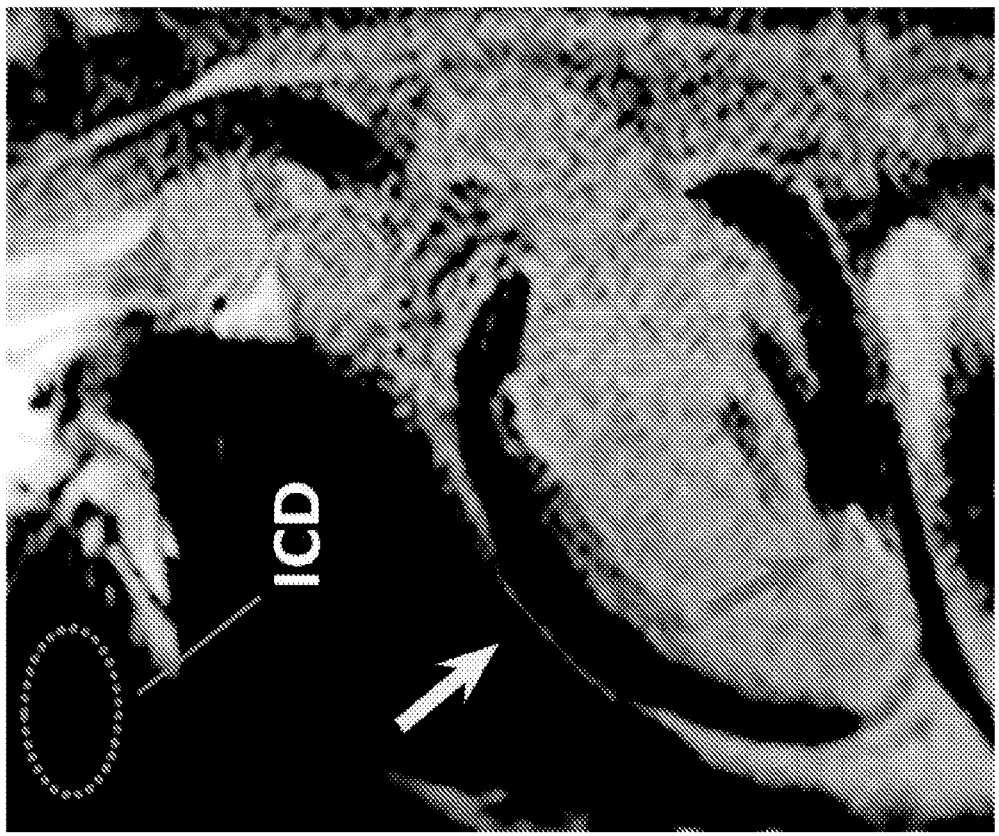
FIGS. 10A and 10B illustrate an exemplary embodiment, showing LGE images from Patient 1 in the 2-chamber, VLA plane. Approximate location of the ICD is indicated with the dotted ellipse. A: LGE image using the conventional LGE sequence. Hyper-intensity artifact was produced in the ventricular wall (top arrow). B: LGE image using the modified wideband LGE sequence. Hyper-intensity artifact has been completely resolved (top arrow). In this patient, scarring and ventricular wall thinning was present near the posterior LV wall (bottom arrows), which is remote from the ICD.
Figure 10A:
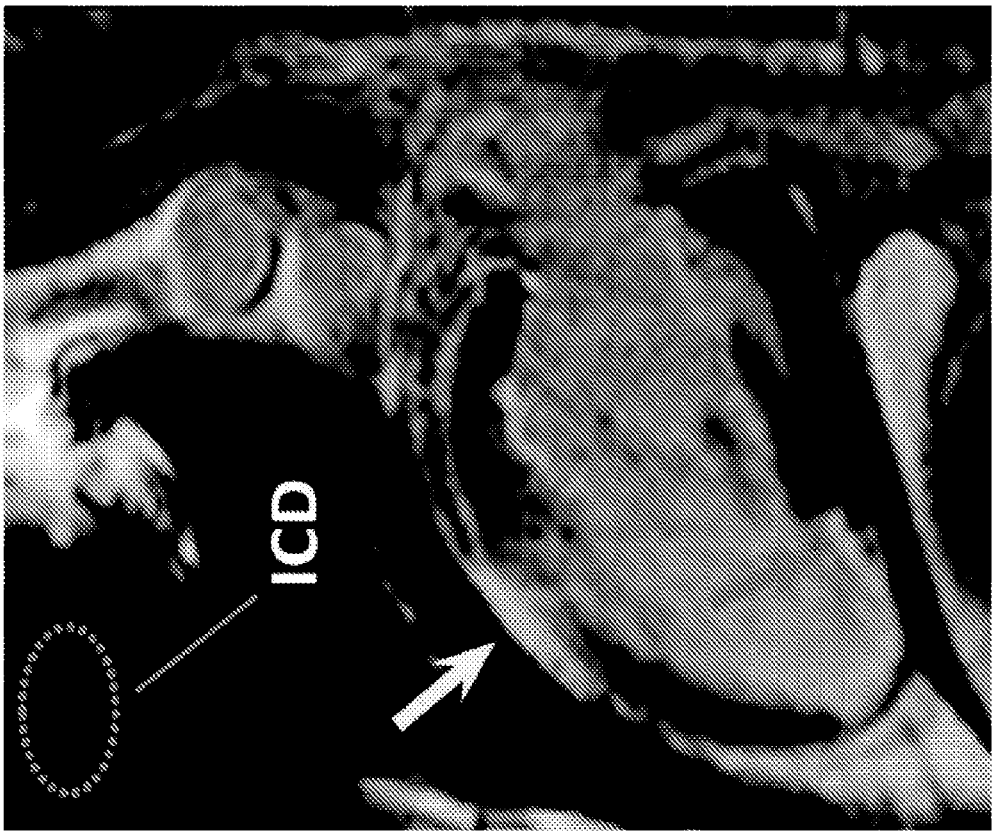

In Patient 1, upon using the conventional LGE sequence, hyper-intensity artifacts were formed in the anterior LV wall, which was in close proximity to the ICD (FIG. 10, top arrows). The artifact could be confused with scar tissue, making an accurate diagnosis difficult. With the wideband LGE sequence, the hyper-intensity artifact was completely removed. Scarring and ventricular wall thinning were identified near the apex.

Figure 11B:
FIGS. 11A and 11B illustrate an exemplary embodiment, showing LGE images from Patient 2 in the 4-chamber HLA plane. A: LGE image using the conventional LGE sequence. Severe hyper-intensity artifact was produced over a large portion of the ventricular wall (top arrow). B: LGE image using the modified wideband LGE sequence. The hyper-intensity artifact was completely eliminated (top arrow). Scar tissue near the apex was clear in the wideband image (B, bottom arrow), but completely obscured by the artifact in the conventional LGE image (A, bottom arrow).
Figure 11A:

In Patient 2, hyper-intensity artifacts were formed over a large portion of the ventricle near the apex using the conventional LGE sequence (FIG. 11A, top arrow). Using the wideband LGE sequence, the artifacts were eliminated and myocardium near the apex was clearly visible. Based on the wideband LGE images, scarring was identified near the apex, which was obscured in the conventional LGE images. In the volunteer and patients 1 & 2, parallel imaging (GRAPPA rate 2) was used in the wideband LGE but not in the conventional LGE, resulting in an apparent increased noise in the wideband images shown in FIGS. 9-11. The scan parameters were subsequently matched between the two LGE sequences in the later stage of the study and hence examples in FIGS. 12 & 13 do not show increased noise for wideband LGE.

Figure 12B:
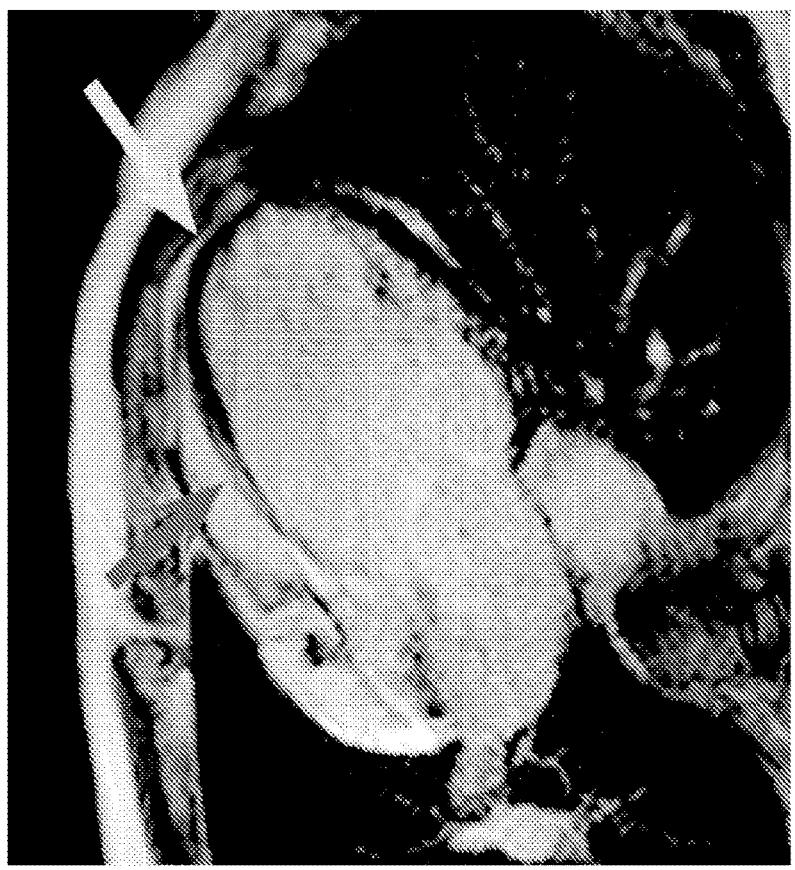
FIGS. 12A and 12B illustrate an exemplary embodiment, showing LGE images from Patient 3 in the 4-chamber HLA plane. A: LGE image using the conventional LGE sequence. Severe hyper-intensity artifact was formed throughout the left ventricular wall (right arrow). B: LGE image using the wideband LGE sequence. The hyper-intensity artifact was completely eliminated (right arrow). Scar tissue at the septum (B, left arrow) was clear in the wideband image, but was completely obscured by the hyper-intensity artifact in the conventional LGE image (A, left arrow).
Figure 12A:
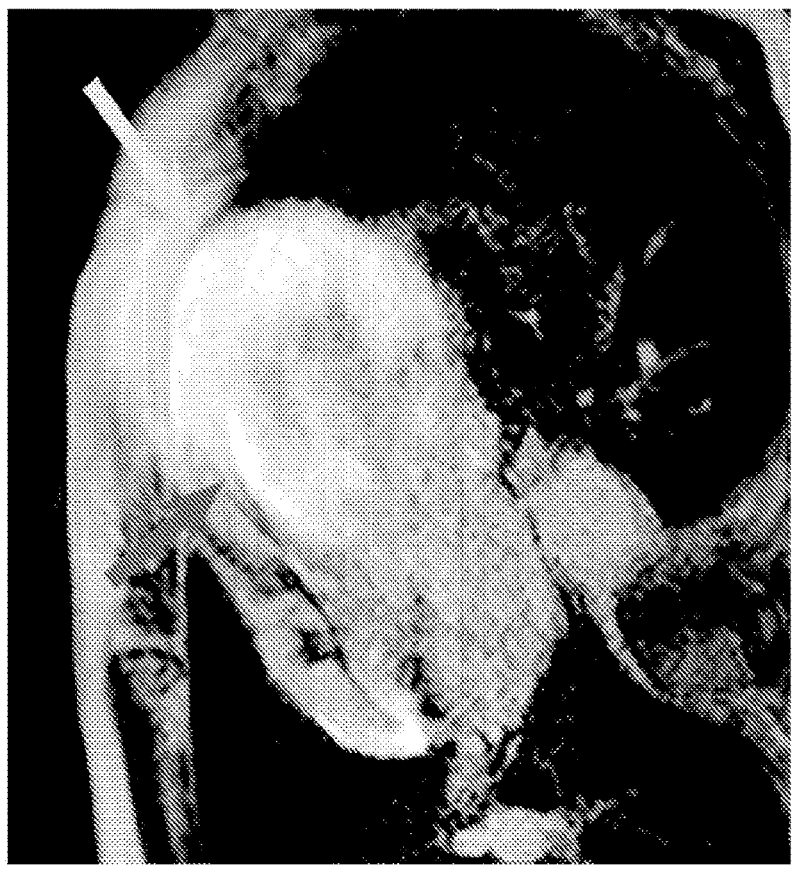

Hyper-intensity artifacts were produced throughout the LV in Patient 3 (FIG. 12A) and apical regions of the LV in Patient 4 (FIG. 13A) using the conventional LGE sequence. The artifacts were completely resolved using the wideband LGE sequence (FIGS. 12B & 13B). Patient 3 had scarring at the septum, which was completely obscured in the conventional LGE image (FIG. 12A, left arrow), but visible in the wideband LGE image (FIG. 12B, left arrow). Patient 4 had an apical aneurysm, which was obscured in the conventional LGE image (FIG. 13A, right arrow), but much clearer in the wideband LGE image (FIG. 13B, right arrow).

ICD leads were noted in the RV, adjacent to the septum, in LGE images of a few patients. An example is indicated in FIG. 13. No artifacts were seen in the myocardium that could be directly caused by leads.

Summary of Key Results

The results of the study indicate that diagnostic quality LGE MRI of patients with ICDs is feasible using the wideband technique. Data collected from 10 ICD patients demonstrate that the commonly seen hyper-intensity artifacts can be removed using the wideband LGE technique.

The off-resonance induced by the generator of an ICD was measured. This off-resonance was shown to be in the 2-6 kHz range at distances of 5-10 cm, which is often the typical distance of an ICD from the myocardium in patients (see Phantom Studies). The results show that the off-resonance induced by an ICD decreases with distance, and that the standard LGE sequence produces hyper-intensity artifacts if an ICD is implanted less than about 16 cm from the heart.

Pros and Cons of Using Wideband Inversion Pulses

The main advantage of using a wideband inversion pulse is that it allows the elimination of the hyper-intensity artifacts that appear in LGE images of ICD patients without requiring additional hardware, time, or reconstruction requirement. One disadvantage of the proposed sequence is that a wider bandwidth adiabatic RF pulse requires a higher B1 amplitude. This results in an increased SAR. In the in-vivo scans, SAR for the conventional LGE sequence varied from 0.05 to 0.08 W/kg, while SAR for the proposed wideband LGE sequence varied from 0.07 to 0.1 W/kg. The increase in SAR from the conventional sequence to the proposed sequence varied from 19% to 56%. Though the SAR limit of 2 W/kg was not approached in this study, the B1 requirement has to be accounted for when designing RF pulses of higher bandwidth, to ensure that the scanner's B1 limit is not exceeded.

Geometric Distortions

The wideband LGE sequence does not correct any geometric distortions caused by the off-resonance. An off-resonance in the kHz range could potentially translate to prominent image distortion in both the frequency encode direction (in-plane) and the slice select direction (through-plane). Image distortions due to the presence of metallic implants have been addressed by numerous techniques. The most widely used are MAVRIC and SEMAC. These methods can potentially be applied to the wideband LGE imaging to reduce image distortions. A disadvantage of these sequences is that multiple acquisitions are required, which together with cardiac gating, could make the scan duration unfeasible for cardiac imaging.

Conclusion

The LGE MRI technique for patients with implanted cardiac devices has been modified using a wideband inversion pulse. The wideband LGE technique removes the hyper-intensity artifacts that are typically seen with conventional LGE MRI. The feasibility study suggests that the technique can enable the successful use of LGE MRI in patients with cardiac devices who would otherwise be inaccessible to diagnosis. Results from clinical studies are presented as separate examples.

Example 5

Additional Experimental Setup and Configurations

Wideband LGE Pulse Sequence Design and Simulation

To address the inversion pulse spectral BW issue of the current LGE sequence, a wideband adiabatic inversion pulse was designed and implemented to ensure proper inversion of the myocardium affected by the device generator.

Adiabatic RF inversion pulses are preferred for inversion recovery sequences such as LGE because adiabatic pulses are insensitive to $B_1$ inhomogeneity and produce excitation uniformly. The most commonly used adiabatic inversion pulse is the HS pulse, which consists of amplitude and phase modulation functions:

$$A(t) = A_0 \operatorname{sech} \beta t \qquad [1]$$

$$\phi(t) = \mu \ln(\operatorname{sech}\beta t) \pm \mu \ln A_0 \qquad [2]$$

$A_0$ is the peak $B_1$ field, $\beta$ is a frequency modulation parameter (in units of rad/s) and $\mu$ is a phase parameter (dimensionless). For the adiabatic passage condition to be fulfilled, the peak $B_1$ amplitude, $A_0$, must exceed the threshold given by the following expression:

$$A_0 \gg \frac{\sqrt{\mu}\,\beta}{\gamma} \qquad [3]$$

The center of the modulation frequency can be offset by adding a time-frequency-offset product, $tf_{offset}$ to the phase modulation function.

The spectral bandwidth of a hyperbolic secant pulse is given by the product of the frequency modulation parameter and the phase modulation parameter: $\mu\beta$. Thus, by altering either or both of these parameters, the bandwidth can be modified.

The conventional LGE sequence on the 1.5 T MR scanners uses a HS inversion pulse with $\beta=672$ rad/s and $\mu=5$, which yields a bandwidth of 1.1 kHz. From the literature and the prior experience, it has been observed that this bandwidth is insufficient for LGE imaging in the presence of an implanted cardiac device. The metal casing of the ICD induces off-resonance in the myocardium greater than 1 kHz. As a result, the off-resonant myocardium spins are not fully inverted when the inversion pulse is applied, and these spins give rise to the hyper-intensity artifacts typically seen.

To overcome this artifact, new HS inversion pulses with wider bandwidths were designed. During the initial phase of the study, a pulse with $\beta=750$ rad/s and $\mu=10$ was implemented, which yielded a bandwidth of 2.4 kHz. Subsequently, the BW was increased even further to 3.8 kHz using $\beta=750$ rad/s and $\mu=16$. The potential issue with wideband adiabatic inversion pulses is that they require higher $B_1$ field to satisfy the adiabatic passage condition in Eq. [3]. Only a small increase to $\beta$ and a larger increase to $\mu$ were made, in comparison to the conventional inversion pulse, because the minimum $B_1$ amplitude for adiabatic inversion scales linearly with $\beta$ but only as the square root of $\mu$ (Eq. [3]). The minimum $B_1$ amplitude required to fulfill the adiabatic condition is 8.9 µT for the 2.4 kHz pulse, and 11.2 µT for the 3.8 kHz pulse. The new inversion pulses were implemented into the existing 2D inversion recovery LGE sequence, replacing the standard 1.1 kHz inversion pulse. The new inversion pulses were tested on a Bloch equation simulator in Matlab (The Mathworks, Natick, Mass.). Inversion performance and bandwidth were tested by generating plots of the longitudinal magnetization against a range of off-resonance frequencies.

All MR imaging was carried out on 1.5 T MR scanners, which were equipped with 40 mT/m gradients with maximum slew rates of 200 T/m/s. Phantom experiments were carried out using an 8 channel spine coil and volunteer and patient imaging was carried out using a 6 channel body coil. In phantom and healthy volunteer experiments, an ICD (ATLAS II, Model # V-268, St. Jude's Medical, Sylmar, Calif.), was used to simulate the off-resonance effects of these devices on patients.

Phantom Experiments

The modified wideband LGE sequences were tested on the American College of Radiology (ACR) standard phantom. The optimal inversion time for the solution in the ACR phantom was determined using a Look-Locker sequence in the absence of the ICD. The ICD was positioned at a distance of 6 cm from the phantom. LGE images were acquired using the standard LGE sequence (using the 1.1 kHz inversion pulse) and the modified LGE sequences (using both 2.4 kHz and 3.8 kHz bandwidth inversion pulses).

To study the relationship between ICD-caused off-resonance and the distance from ICD, the ICD was placed 5 cm away from the edge of the phantom. The $B_0$ field map was measured using two single-echo gradient echo sequences with 2.5 ms and 3.5 ms echo times. The field map was calculated as the phase difference between the two images divided by the difference in echo time. Phase was unwrapped in the phase difference image by applying the Matlab function "unwrap" along columns on the phantom pixels; phase at the top of the phantom in the phase difference image was unaffected by the ICD since the ICD was at the bottom edge of the phantom (see FIG. 15A).

Wideband LGE Pulse Sequence Design and Simulations

The properties of the inversion pulses, including amplitude, frequency and phase modulation functions, and the longitudinal magnetization profile produced, are shown in FIG. 14. The standard HS inversion pulse used in the conventional LGE sequence is shown in FIG. 14A. This pulse used $\beta=672$ rad/s and $\mu=5$. This yielded a bandwidth of 1.1 kHz and required a minimum $B_1$ amplitude of 5.6 µT. This bandwidth is adequate for routine imaging in the absence of cardiac devices, but is not adequate for large off-resonance as those introduced by the presence of a cardiac device. FIG. 14B shows the modulation functions of the 3.8 kHz inversion pulse with a center frequency shift of 1.5 kHz. In all of the in vivo studies, this center frequency was shifted by 0 to ±1500 Hz to ensure both the on-resonance and off-resonance tissue stay within the spectral bandwidth of the new wideband inversion pulse.

A pulse sequence diagram for the LGE sequence, with the new 3.8 kHz BW inversion pulse implemented, is shown in FIG. 14C. The phase modulation function shown in the sequence diagram is wrapped about ±2π and shows rapid changes. LGE sequences used clinically are segmented GRE sequences, with 15-25 lines per k-space segment.

Field Map and Phantom Results

Figures 2, 15A:
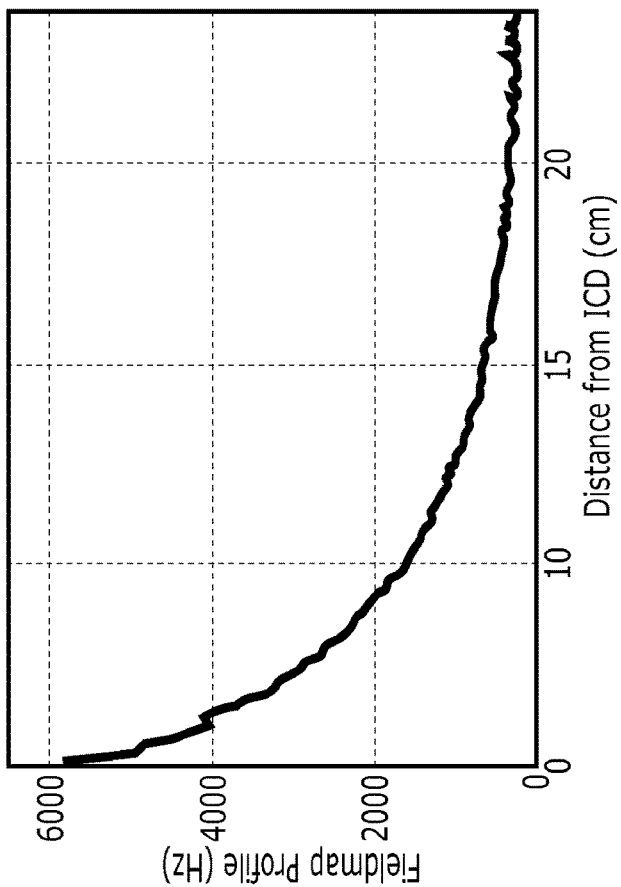
Figures 1, 15A:
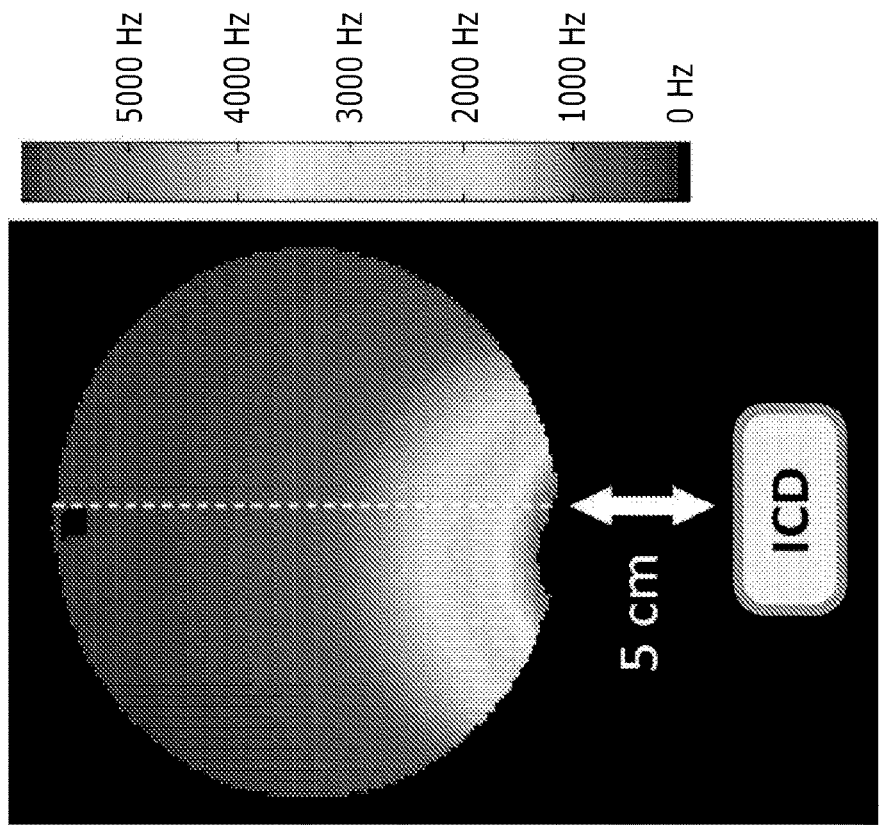

FIG. 15A shows the results of the field map measurements. The left image shows the field map generated across an ACR phantom when an ICD is placed 5 cm from the phantom. The graph on the right shows the field profile (along the dotted line on the field map). The off-resonance due to the ICD is about 6 kHz at a distance of 5 cm, which drops to about 2 kHz at 10 cm. Typically, an ICD is implanted at a distance approximately 5-10 cm from the heart. Thus, the field map data suggests that the off-resonance values experienced at the myocardium due to an ICD lies roughly in the 2-6 kHz range.

The conventional LGE sequence uses an inversion pulse with a 1.1 kHz BW. This is sufficient to invert spins which are off-resonance up to ±535 Hz. According to the graph in FIG. 15A, this suggests that if the distance of an ICD from the myocardium is less than approximately 16 cm, hyper-intensity artifacts will be produced when utilizing the conventional LGE sequence. Thus, if a patient has an ICD implanted at the right shoulder, the conventional LGE sequence would be adequate.

Figure 15B:
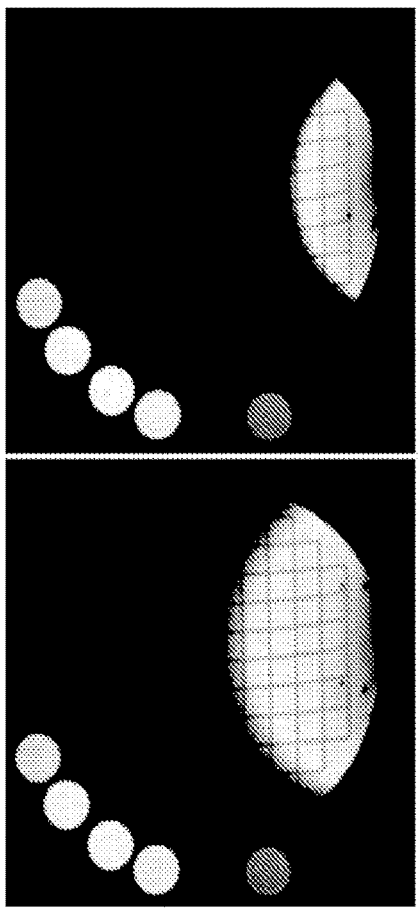
Figure 15B:
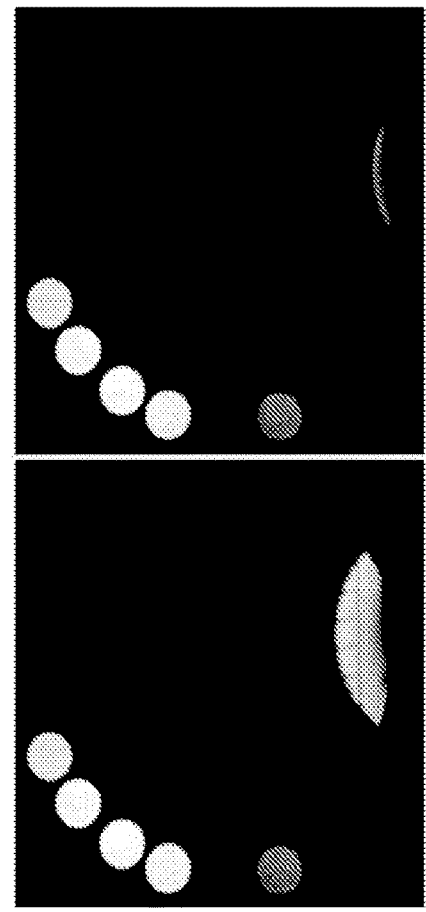
Figure 15B:
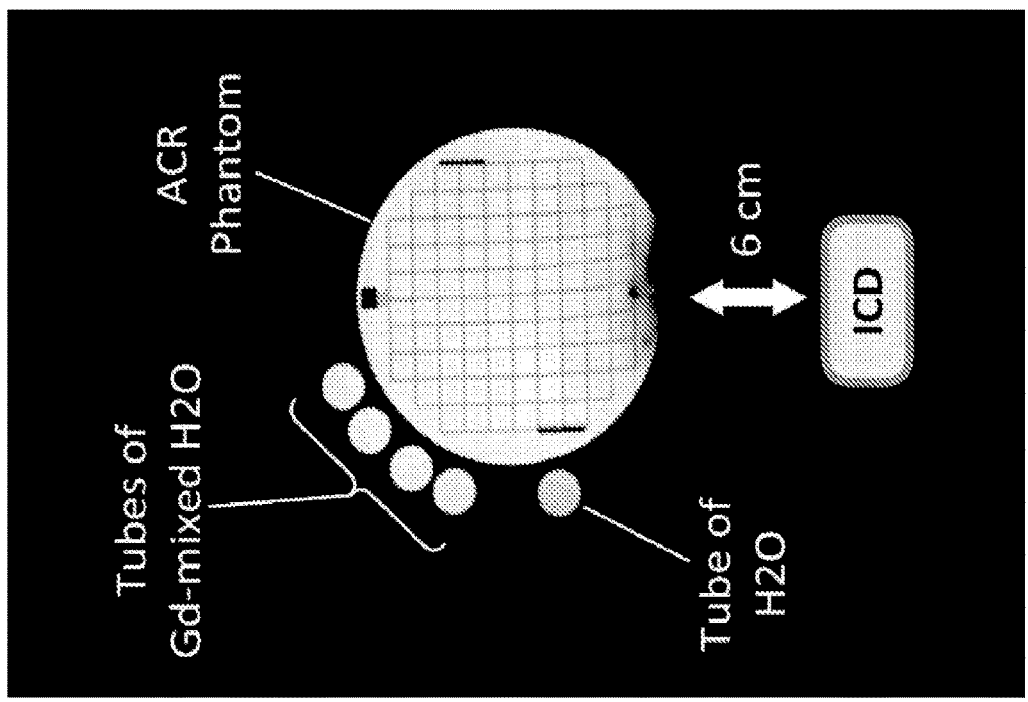

FIGS. 15B & 15C illustrate the effect of the conventional and new inversion pulses on an ACR phantom, with an ICD placed 6 cm away. FIG. 15B shows a GRE image (no inversion pulse) of the phantom setup. In FIG. 15C top left, the phantom was imaged with the conventional LGE sequence using the 1.1 kHz inversion pulse applied at a TI of 110 ms. In the absence of an ICD, this inversion pulse is sufficient to nullify the entire phantom image. However, off-resonance due to the ICD prevents inversion of the spins near the ICD, resulting in a hyper-intensity artifact that spans over one-third of the phantom. FIG. 15C top right and bottom left shows the LGE images of the phantom with inversion pulses of BW 2.4 kHz and 3.8 kHz, which are sufficient to invert off-resonance up to 1.2 kHz and 1.7 kHz, respectively. The increasing spectral coverage of the inversion pulse causes the hyper-intensity artifact to become progressively smaller. FIG. 15C bottom right shows an image with 3.8 kHz BW inversion pulse in which the center of the modulation frequency was shifted by 1500 Hz. This frequency offset increases the spectral coverage up to 3.2 kHz off-resonance, which is why the hyper-intensity artifact is even smaller than in the bottom left image.

Geometric distortions of the ACR phantom grid, due to ICD off-resonance, can be seen in FIGS. 15B & 15C. Grid squares close to the ICD were distorted left-to-right, which is the frequency encode direction for these images. Dimensions of the grid squares were 1.5×1.5 cm, and the grid is 2 cm from the circumference. Thus, the distortions become noticeable at a distance of about 12-13 cm away from the ICD. In these five images, the receiver bandwidth was 500 Hz/pixel, which is the value used in conventional LGE.

Example 6

Assessment of Wideband LGE MRI and Correlation with Electroanatomical Mapping

Late Gadolinium Enhancement (LGE) MRI of ventricular scar has been shown to be accurate for detection and characterization of arrhythmia substrates. However, the majority of patients referred for ventricular tachycardia (VT) ablation have an implantable cardioverter defibrillator (ICD), which obscures image integrity and the clinical utility of MRI. Device generator artifact is caused by the multi-kHz frequency shift of tissues 5-10 cm away from the device generator. The resulting images have bright artifacts, which are problematic since LGE also renders tissue bright indicating scar. The aims of this study were 1) to assess the ability of the wideband LGE technique to remove ICD artifacts compared to standard inversion pulse protocol in patients referred for scar-mediated VT and 2) to correlate the scar identified on wideband LGE MRI with invasive electroanatomic mapping.

In this example, a wideband LGE MRI technique for device artifact removal was developed and validated. Its correlation with electroanatomical mapping was also explored.

A novel wideband LGE MRI technique was developed to allow improved scar evaluation on patients with ICDs. The wideband technique and the standard LGE MRI were tested on 18 patients with ICDs. VT ablation was performed in 13 of 18 patients with either endocardial and/or epicardial approach and the correlation between the scar identified on MRI and electroanatomical mapping was analyzed.

Hyper-intensity artifact was present in 16/18 of patients using standard MRI, which was eliminated using the wideband LGE and allowed for MRI interpretation in 15/16 patients. All patients had ICD lead characteristics confirmed as unchanged post-MRI and had no adverse events. LGE scar was seen in 11/18 patients. Among the 15 patients where wideband LGE allowed visualization of myocardium, 10 had LGE scar and 5 had normal myocardium in the regions with image artifacts when using the standard LGE. The left ventricular scar size measurements using wideband MRI and electroanatomical maps (EAM) were correlated with $R^2=0.83$, $P=0.00003$.

The wideband LGE-MRI improves the ability to visualize myocardium for clinical interpretation, which correlated well with EAM findings during VT ablation.

Methods

Eighteen patients who had received ICD therapy for VT were referred for cardiac MRI including LGE to determine if there was relevant ventricular scar in perioperative planning for potential VT ablation. Both the standard LGE MRI protocol and the wideband LGE MRI protocol were performed. Of the 18 patients with VT who had LGE-MRI, 13 underwent VT ablation with high density electroanatomical maps (EAM) and the findings were compared. Written informed consent was obtained from all participants, and the HIPAA-compliant protocol was approved by the Institutional Review Board.

Wideband LGE MRI Sequence

In the standard LGE MRI, there is typically a non-selective adiabatic inversion pulse with a spectral bandwidth of approximately 1 kHz. This inversion pulse creates a strong T1-weighed image with good contrast between scar and viable myocardium. However, in the presence of an ICD, regions of the heart that are as far as 5-10 cm from the device generator undergo a strong frequency shift of 2-4 kHz, which is well outside of the 1-kHz spectral bandwidth of the inversion pulse used in the standard LGE. As a consequence, the affected regions are not properly inverted (or nulled) and are hence hyper-intense, undermining diagnostic interpretation. In the wideband LGE MRI sequence, the 1-kHz inversion pulse is replaced with a wideband hyperbolic secant inversion pulse with a spectral bandwidth of 3.8 kHz. This ensures that the myocardium is property inverted by the pulse and hence the hyper-intensity artifact is eliminated. In this implementation, the wideband inversion pulse has the same time duration as the standard inversion pulse and as such, the imaging time is the same as the standard LGE. The wideband inversion pulse requires a higher specific absorption rate (SAR). Based on the SAR simulator provided by the MRI system, the estimated SAR is 0.05 W/kg using the standard LGE MRI and 0.07 W/kg using the wideband LGE due to the higher B1 value required. Although this represents approximately 30% increase in SAR, the overall SAR of both sequences are well below the FDA regulation of 2 W/kg. The wideband inversion pulse requires higher minimum B1 value of 12 uT to satisfy the adiabatic condition, which should be feasible on most commercial MRI systems.

MRI Acquisition

All LGE-MRI studies were acquired using a 1.5 Tesla MRI system (Avanto, Siemens Healthcare, Erlangen, Germany). Safety procedures for MRI of patients with implantable devices has been previously described and are adopted. Patients that were pacemaker dependent, or had implantation within 6 months, or abandoned leads were excluded. A physician or nurse practitioner with specialized training in implantable cardiac devices, as well as a representative from the device company, interrogated ICD parameters prior to MRI. All therapies and detections were disabled, and the lead thresholds, impedance, and battery voltage were checked. Continuous hemodynamic and ECG monitoring was performed during the MRI. Immediately after the completion of the MRI protocol, any clinical events were recorded and the device was interrogated again to check for any changes in ICD parameters. All tachycardia detection and therapies were enabled at the conclusion of the study.

The MRI protocol included standard cardiac cine MRI, contrast-enhanced MR angiography and LGE MRI. For each patient, Gd-DTPA was used at 0.2 mmol/kg body weight. Both standard LGE MRI and the wideband LGE were acquired. For each 2D imaging slice, the standard LGE was immediately followed by the wideband LGE at the same slice. Typically 8-12 short-axis slices (1.6 mm inter-slice gap) and 3-5 long-axis images were acquired to obtain sufficient anatomical coverage of the LV. All the image slice orientations were prescribed based on scout images and a three-point slice definition tool on the scanner. The long axis images typically included both horizontal and vertical long axis orientations. The inversion time (TI) was continuously increased by 10 ms every 2 minutes to maintain good suppression of normal myocardium as the gadolinium contrast agent is washed out. The LGE MRI pulse sequence parameters were: TR/TE=4.1/1.5 ms, FOV=360 mm, FA=25°, readout bandwidth=500 Hz/pixel, slice thickness=8 mm, resolution=1.4×1.9 mm, TI=250-400 ms. The duration of the complete MRI protocol was approximately 60-80 minutes. The duration of the wideband LGE that was added to the standard cardiac MRI protocol was approximately 10-15 minutes due to the need for multiple breath-hold and rests in between breath-holds.

Electrophysiological Study and Catheter Ablation

Of the 18 consecutive patients with ICD who underwent MRI, 13 were referred for ablation. Electroanatomical mapping was performed using high density electroanatomical maps using CARTO (Biosense Webster, Diamond Bar, Calif.) or NavX (St. Jude Medical, Minneapolis, Minn.) with greater density sampling of regions with low voltage (0.5-1.5 mV). Dense scar was defined as <0.5 mV and border zone was defined as 0.5-1.5 mV. Only dense scar (<0.5 mV) was used to measure epicardial scar area.

Epicardial access was left to the discretion of the operator and performed using standard techniques described by Sosa et al. Epicardial access and mapping, when performed, was done prior to endocardial access to minimize exposure to systemic heparin during endocardial access. Endocardial ventricular access was obtained with either single or double transseptal access with standard BRK-1 access guided by Intracardiac Echocardiography, and either Mullens 8F sheath or Agilis deflectable sheaths (St. Jude Medical). Both endocardial and epicardial mapping was performed with either Thermocool 3.5 mm (Biosense Webster, Diamond Bar, Calif.), or Chilli 2 (Boston Scientific, Natick, Mass.). High density mapping was performed with a duodecapolar multipolar catheter (Livewire 2-2-2 mm duodecapolar catheter, St. Jude Medical) as previously described 10. Bipolar signals were filtered at 5-500 Hz and displayed at 100 mm/s.

Artifact and Scar Size Measurements

The area of LV myocardial tissue that had hyper-intensity image artifacts due to ICD when using the standard LGE MRI was measured for each short-axis slice. The measurements were subsequently summed over all the short-axis slices for each patient and were multiplied by the slice thickness (and any inter-slice gap), which yields the total size of artifact in the myocardium. For each patient who had a chest X-ray either before or after MRI, the distance between the ICD and LV was measured based on the anterior-posterior X-ray image. The artifact size measurements and the ICD-to-LV distance were subsequently correlated using a linear regression. Patients with no chest X-ray (patients 6, 8, and 12), the patient with right sided ICD (patient 5) and the patient with ICD overlying LV (patient 17) were excluded from the correlation.

The sizes of both endocardial and epicardial scars were measured based on the wideband LGE MRI. For each patient, the short-axis wideband LGE images with scars were identified. On each of the identified image, a curve was drawn along the endocardial surface of any endocardial scar and along the epicardial surface for any epicardial scar (or both for transmural scar). The total length of the endocardial and epicardial curves was multiplied by the sum of the slice thickness and any inter-slice gap, which gives the endocardial and epicardial surface area for the slice. These measurements were added among all the short-axis slices with scars, which yields the total endocardial and epicardial scar surface area for the each patient.

On EAM, retrospective electrogram analysis of low voltage regions was performed by two physicians. Scar was measured ($cm^2$) using the incorporated software of the mapping system. Low voltage regions were excluded if there was poor catheter contact or suspected epicardial fat based on the appearance of the local electrograms.

Results

The mean age was 52+/−13.4 years old, and 94% were male. Mean ejection fraction was 36.7% (+/−15.6), 16% had ischemic cardiomyopathy and 66% had non-ischemic etiologies. Patient clinical characteristics are outlined in Table 1 below.

TABLE 1

Clinical summary of the 18 VT patients with ICDs who underwent cardiac MRI for assessment of myocardial scar.

| Patient Index | Clinical | Wideband LGE Scar Location | CXR Distance (Can to LV Border) (mm) |
|---|---|---|---|
| 1. | Chagas Disease, EF 48% | Basal lateral and apex | 15.2 |
| 2. | Ischemic, EF 33%. | Inferior | 25.9 |
| 3. | Non-ischemic EF 35% | Basal lateral | 18.9 |
| 4. | Non-ischemic EF 40% | Anterior | 48.8 |
| 5. | Ischemic EF 36%, mechanical aortic and mitral valves. | Inferior | Right sided ICD |
| 6. | ARVD, EF 60% | Possible RV free wall. | — |
| 7. | Brugada, EF 60% | No Scar | 33.2 |
| 8. | Apical Hypertrophic Cardiomyopathy EF 60% | Apical Aneurysm | — |
| 9. | Ischemic EF 55% | Inferior lateral Endocardial. | 10.2 |
| 10. | Hypertrophic Cardiomyopathy EF 24% | Transmural Apical and entire LV Mid cavity to apex | 44.4 |
| 11. | PVC/Tachycardia related cardiomyopathy EF 30% | No scar | 71.6 |
| 12. | Non-ischemic CM EF 45% | Apex | — |
| 13. | Non-ischemic EF 23% | No scar | 43.4 |
| 14. | Non-ischemic EF 15% | No scar | 44.1 |
| 15. | Non-ischemic EF 15% | Septum, basal to mid cavity. | 43.8 |
| 16. | Non-ischemic EF 33%, sarcoidosis. | No scar | 25.7 |
| 17. | Non-ischemic EF 10% with Mitral Clip. | No scar, anterior wall not seen due to MRI signal void. | Overlying left ventricle by 31 mm. |
| 18. | Non-ischemic EF 36.2% | Small linear scar inferior septum | 56.7 |

Figure 16:
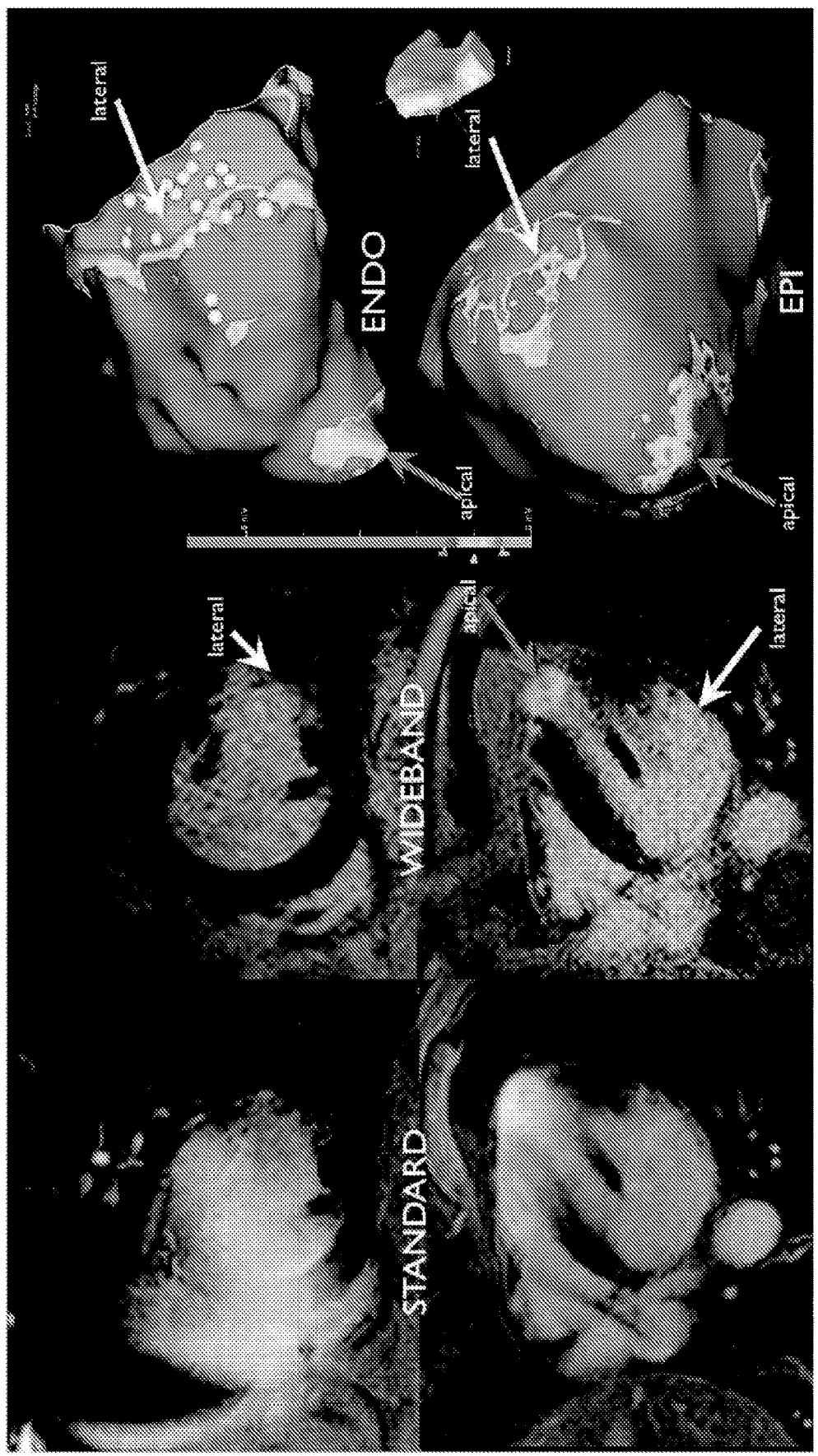
FIG. 16 illustrates an exemplary embodiment, showing standard pulse sequence MRI with significant hyper-intensity artifact from the Implantable Cardioverter Defibrillator (Left) compared to wideband Late Gadolinium Enhancement MRI (right) in a patient with Chagas disease and apical and basal lateral scar. Combined epicardial-endocardial mapping identified scar that correlated with imaging.
Figure 17A:
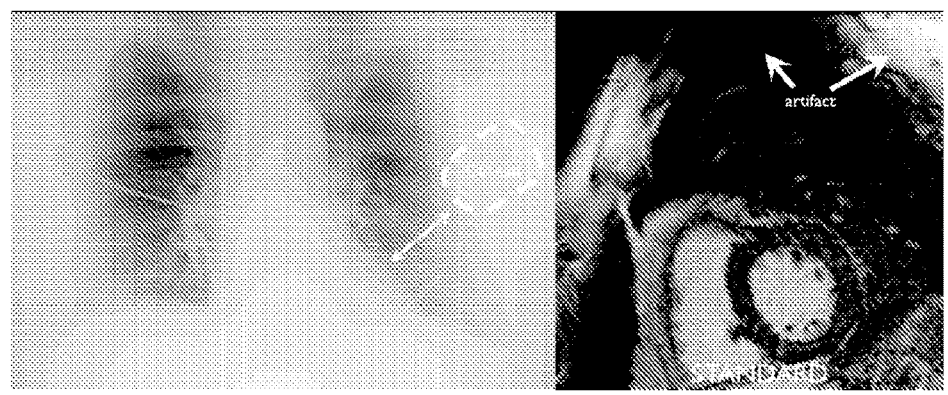
FIGS. 17A, 17B and 17C illustrate an exemplary embodiment, showing Relationship between can distance from heart on chest x-ray and MRI artifact using standard LGE: A): patient with longest distance between ICD and left heart border with no artifact (upper right) on standard MRI; B): Chest X-ray of patient with closest ICD to the left heart border within the patient cohort of this study showing extensive signal void artifact that cannot be corrected by the wideband LGE due to intra-voxel MRI signal dephasing; and C): The ICD-to-LV distance and the artifact size is negatively correlated.
Figure 17B:
Figure 17C:
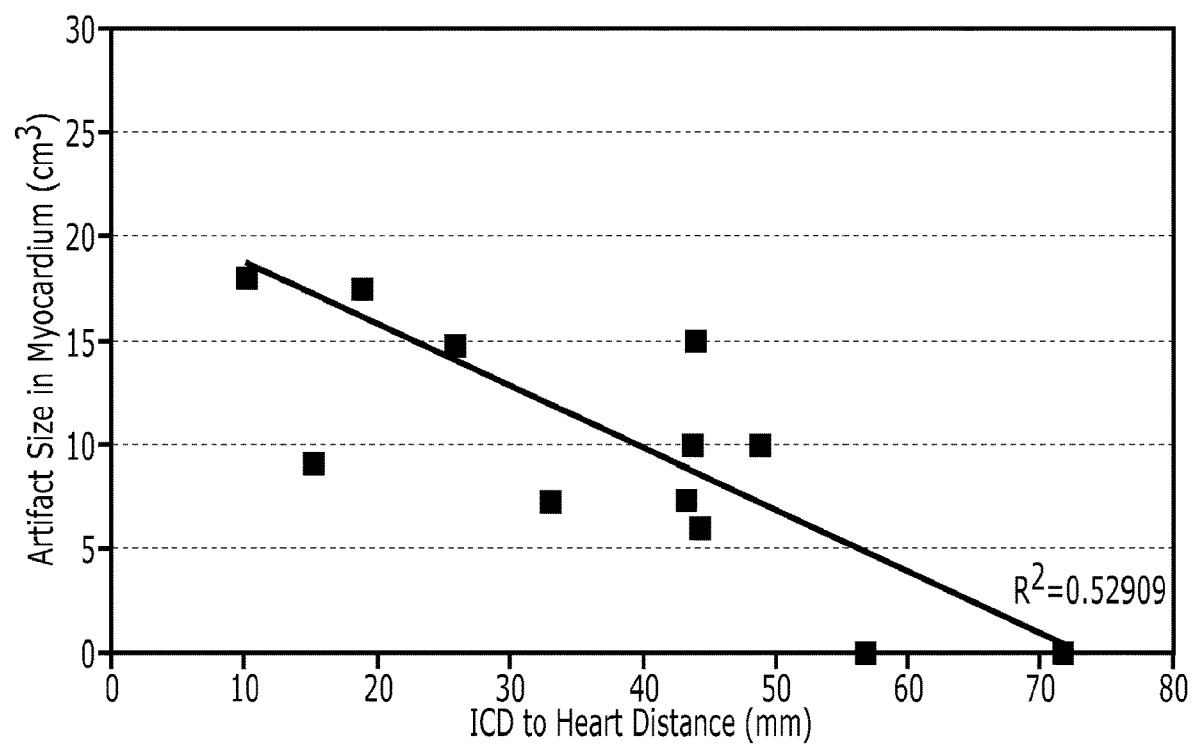

ICD artifact was present in 89% (16/18) of patients, obscuring interpretation of multiple LV myocardial segments. Of the two patients without artifact at baseline, one had a right side ICD (patient 5) and the other had a large body habitus with lateral position of ICD (patient 11). This patient had longest distance measured among the left sided devices within the patient cohort between the ICD can and the LV border on chest X-ray (71.6 mm). The most common artifact location was on the anterior wall of the left ventricle (LV), and nearby areas such as the LV septum and apex. Using the wideband technique, artifact was successfully removed allowing for interpretation of the previously obscured myocardium in 93% (15/16). FIG. 16 shows a comparison between standard LGE, wideband LGE and EAM map. Apical and basal lateral scars, which are obscured using the standard LGE, are clearly shown in the wideband LGE, which correlates well with the EAM scars in the same segments. The only case (patient 17) where interpretation of myocardial segments could not be done had the ICD can in close proximity to the LV border, overlying it by 31 mm on chest X-ray. In this patient, as shown in the example of FIG. 17b, the ICD is sufficiently close to the myocardium to cause an MRI signal void, which was not overcome using the wideband LGE. The two example images shown in FIG. 17 demonstrate that the amount of artifacts strongly depends on the distance of the ICD. FIG. 17 also shows the negative correlation between hyper-intensity artifact size and the ICD-to-LV distance with $R^2=0.53$.

Figure 18:
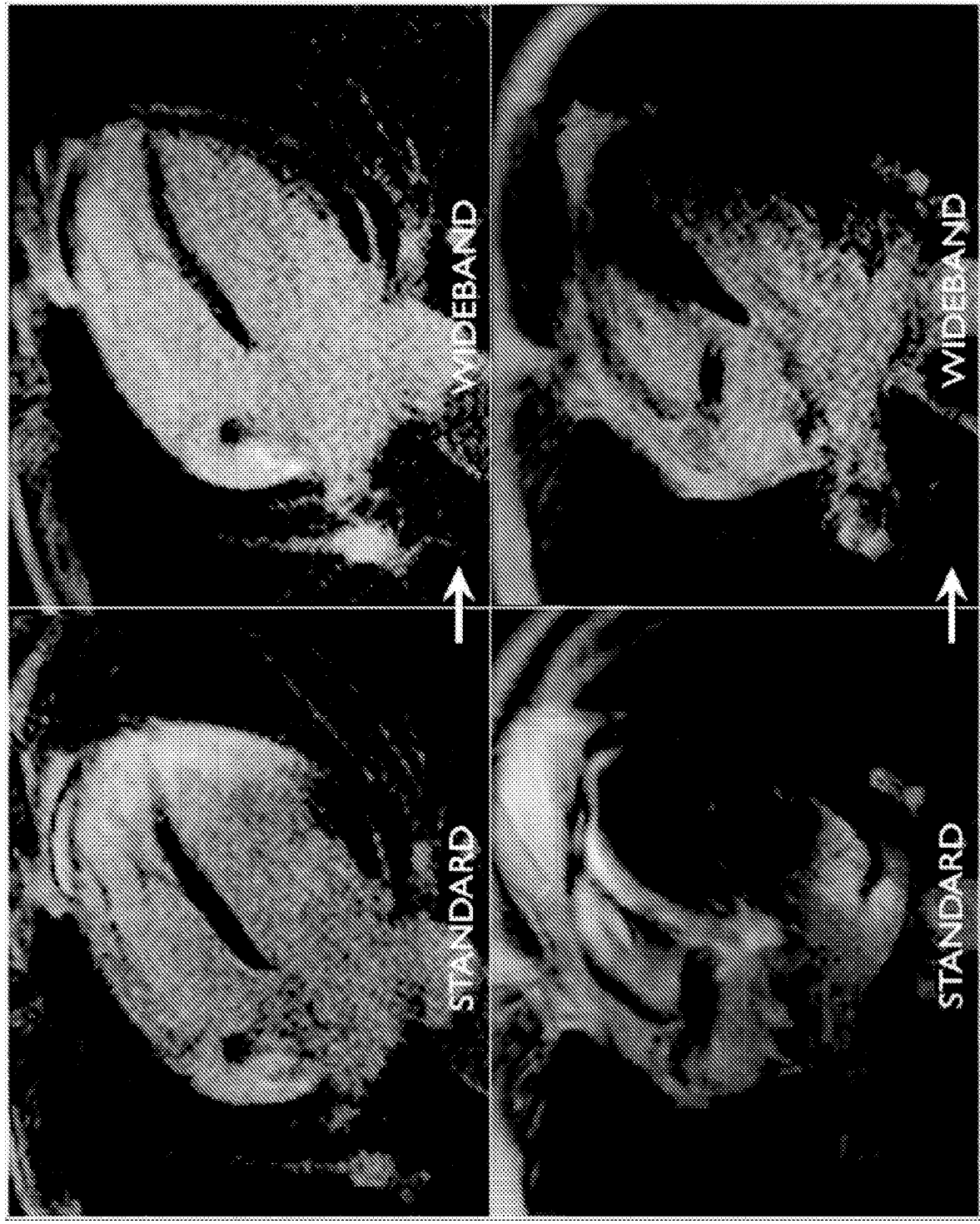
FIG. 18 illustrates an exemplary embodiment, showing elimination of can artifact with wideband technique in two patients reveals normal myocardium in regions previously obscured from clinical interpretation.

All patients had lead thresholds, impedance and sensing checked before and after MRI and no significant changes were observed. No adverse clinical events were observed during the MRI scanning Overall 61% (11/18) patients had LGE scar seen on MRI. Among the 15 patients where wideband allowed improved visualization of myocardium, 10 (66%) had scar in the artifact region when using standard LGE. The other 5 (33%) had normal myocardium in the artifact region, an example of which is shown in FIG. 18.

Figure 19:
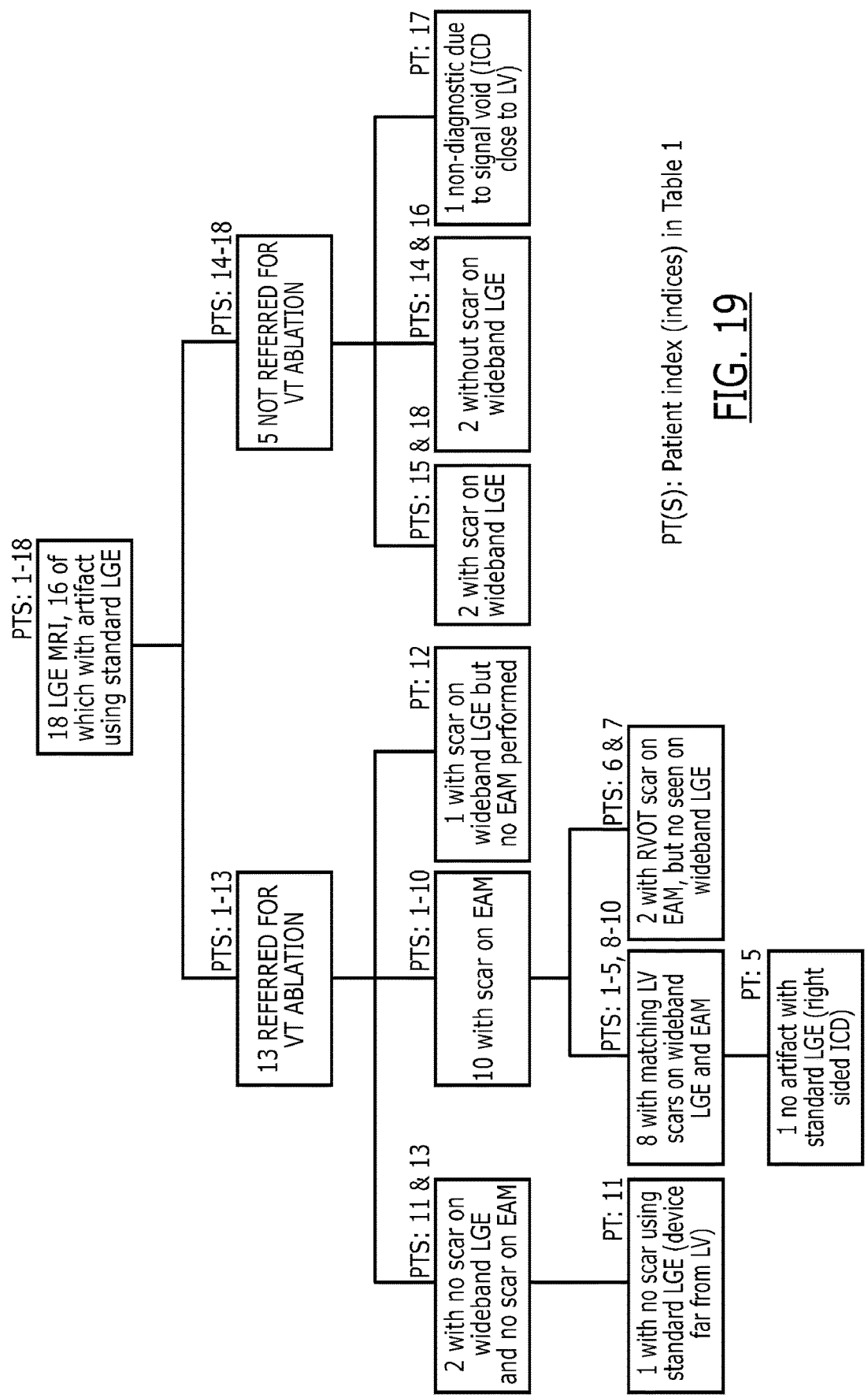
FIG. 19 illustrates an exemplary embodiment, showing flow chart showing breakdown of patients who underwent MRI referred for Ventricular Tachycardia ablation and patients had scar present on MRI and/or on Electroanatomical Map (EAM).

FIG. 19 outlines the breakdown of the patients, and MRI and EAM findings. Among the 18 patients referred for MRI, 13 underwent mapping and ablation of VT. Of the 13 patients, 9 had scar seen on wideband LGE, and the other 4 patients underwent VT ablation at the discretion of the physician and patient even in the absence of LGE scar. Of the 9 patients, one patient (patient 12) underwent activation mapping of a premature ventricular contraction (PVC) with incomplete substrate voltage mapping, although no significant scar was detected in the region of the PVC. Electroanatomical maps were created using the CARTO (n=9) and NavX (n=4) systems. The average map density was 653+/−685 points. Dense myocardial scar was defined as <0.5 mV bipolar, and border zone 0.5 mV-1.5 mV. Only dense scar (<0.5 mV) was used to measure epicardial scar size.

EAM scar was detected in 83% (10 of 12) patients for whom EAM data was available. The 2 of 12 patients with no EAM scar also had no scar in MRI. Overall, among the 10 patients with EAM correlation, 8 had the same regions of scar identified on both wideband LGE MRI and EAM. However, for both patients with RVOT epicardial scar on EAM (one ARVD, one Brugada, patients 6 & 7), LGE-MRI did not reveal scar. Of note, this region was not obscured by significant ICD can artifact for either patient. There were 8 patients who underwent epicardial EAM mapping, 7 of whom had epicardial scar on EAM. There were 5 of 7 epicardial scars (5 of 5 scars for the LV) seen in EAM correlating to regional scars on the wideband LGE MRI. There were 12 patients who underwent endocardial mapping, one of whom (patient 2) was incomplete due to incessant VT. Of the remaining 11 patients with complete endocardial mapping data, 7 patients had scar on EAM and all of the 7 scars were seen on correlating segments on wideband LGE MRI.

Figure 20:
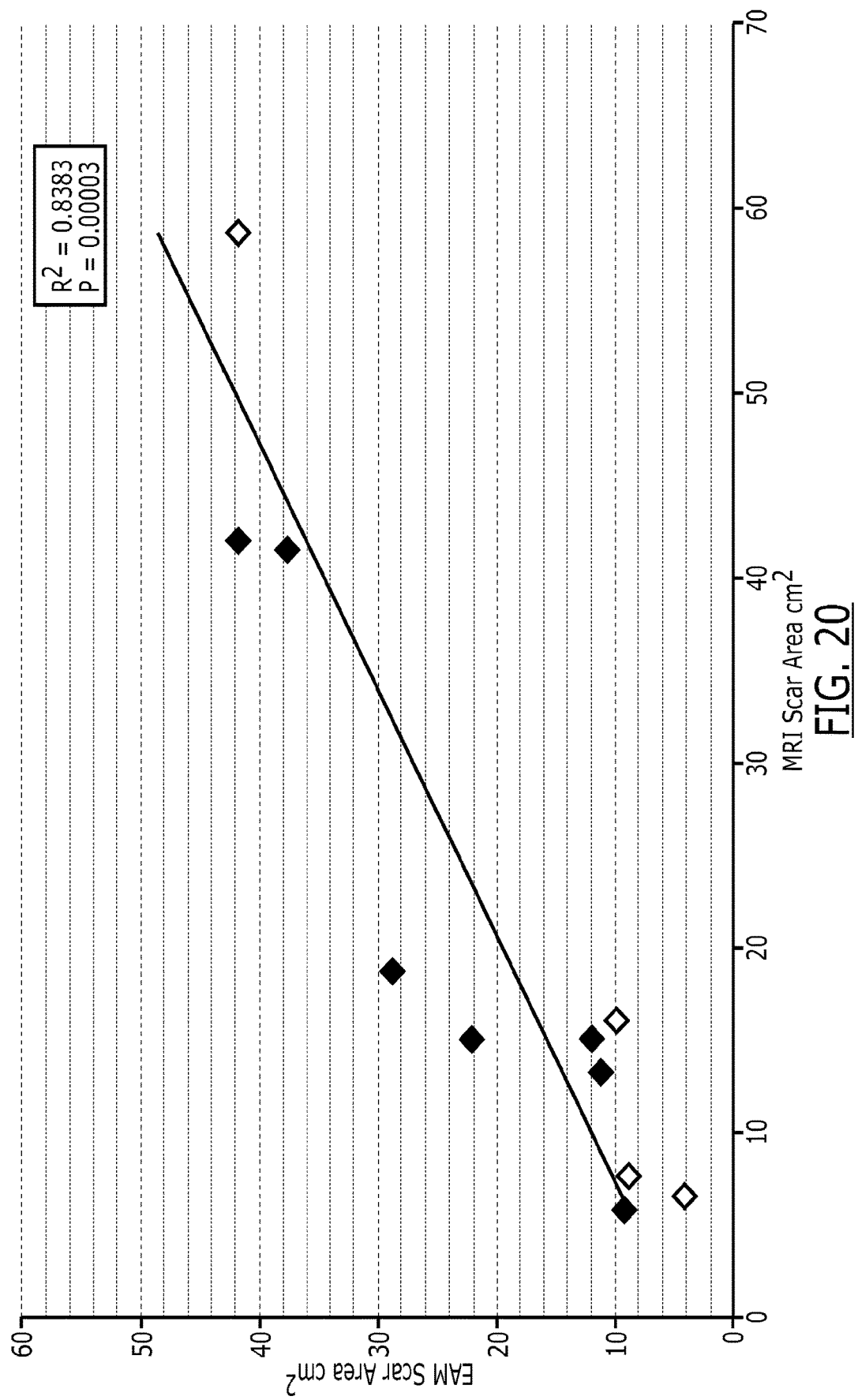
FIG. 20 illustrates an exemplary embodiment, showing correlation of left ventricular (LV) scar size between wideband LGE and EAM based on 11 scar measurements on 8 patients (patients 1-5 and 8-10). Patients with no scars on either wideband LGE or EAM were excluded (patients 11 and 13). Patients with right ventricular (RV) scar seen on EAM were excluded (patients 6 and 7). The epicardial scars are labeled with red points, and endocardial scars are labeled in blue.

The endocardial and epicardial LV scar area correlation between wideband LGE MRI and EAM is shown in FIG. 20, with a Pearson correlation coefficient of 0.91, $R^2=0.83$ (P=0.00003). One epicardial LV scar on an apical aneurysm (patient 8) was excluded due to image artifact and low confidence in scar area measurement as a result, although the endocardial scar of the same patient was still included. The two RVOT scars not seen on MRI were also excluded due to difficulty in measuring RV scar using MRI. The overall mean scar size detected was $18.9\pm16.4$ cm$^2$ on LGE and $20.3\pm13.9$ cm$^2$ on EAM. The mean epicardial scar area was $18.6\pm13.8$ cm$^2$ on MRI and $18.6\pm14.9$ cm$^2$ on EAM. The mean endocardial scar areas on $19.5\pm22.3$ cm$^2$ on MRI and $24.6\pm12.7$ cm$^2$ on EAM. Individual scar areas for each patient are reported in Table 2. The complete removal of the ICD can artifacts allowed integration of the LGE MRI scar maps into the CARTO EAM system to guide the catheter ablation of one patient, shown in FIG. 21 (patient 10).

TABLE 2

Standard LGE MRI compared with wideband LGE MRI and correlated with scar found on electroanatomical maps (EAM).

| Patient Index | Cardiomyopathy | Standard LGE-MRI Artifact Location | Wideband Protocol LGE Scar location. | Electroanatomical Voltage map. | Electrogram RF Target | Scar Area cm$^2$ (wideband MRI and EAM) |
|---|---|---|---|---|---|---|
| 1. | Chagas | Anterior septum. Unable to assess apex and lateral wall. | Basal lateral wall transmural. Apex transmural with aneurysm. | Basalateral wall endo and epi scar (larger endo). Apical scar endo and epi (larger epi). | Basalateral wall endo with VT termination. Apex epi substrate modification. | MRI Endo: 15 Epi: 6.5 EAM Endo: 12.1 Epi: 4.2 |
| 2. | Ischemic | Anterior wall. Cannot see Inferior wall not well seen. | Transmural wall of inferior wall from septum to lateral wall and apical. | Inferior wall epi. Endo scar size difficult to quantify due to incessant VT | Substrate modification with pace maps of inferior wall. Over 6 unstable VT observed. | MRI Transmural: 58.7 EAM Endo: Unable to quantify. Epi: 41.7 |
| 3. | Non-ischemic | Entire image distortion, no interpretation done. | Basal lateral endocardial predominant scar. | Basal lateral scar endo only. | Lateral wall pace map induction and RF termination. | MRI Endo: 18.7 Epi: 11 EAM Endo: 29 |
| 4. | Non-ischemic | Anterior wall | Mid myocardial scar anterior wall. | Anterior wall epi and endo scar. Small posterior lateral wall scar (2.5 cm) not seen on MRI. | Late potentials, pacemap and VT induction and termination anterior wall, epi and endo. | MRI Endo: 15 Epi: 7.6 EAM Endo: 22.3 Epi: 9.0 |
| 5. | Ischemic, mechanical aortic and mitral valve. | No artifact (*Right sided device) | Inferior wall transmural scar. | Low voltage inferior wall endo only. | Late potentials of inferior wall. Mid diastolic potentials with VT termination. | MRI Transmural: 42.0 EAM Endo: 41.9 |
| 6. | ARVD | Apical RV and LV. | No definitive scar seen. Possible RV free wall scar. | RVOT and small free wall scar epi only. | RVOT late potentials and VT termination with mid-diastolic potential. | MRI No scar EAM Endo: No scar Epi: 25.0 |
| 7. | Brugada | Significant LV artifact No interpretable segments. | No scar seen, normal MRI. | RVOT epi scar. | Late potentials in Epicardial RVOT. | MRI No scar EAM Endo: No scar Epi: 9.8 |
| 8. | Apical Hypertrophic Cardiomyopathy | Significant LV artifact No interpretable segments. | Apical aneurysm with transmural scar. | Epi and endo Apical Scar | Split potential epi and late potentials endo. | MRI Endo: 5.8 Epi: Unable to assess. EAM Endo: 9.4 Epi: 33.2 |

TABLE 2-continued

Standard LGE MRI compared with wideband LGE MRI and
correlated with scar found on electroanatomical maps (EAM).

| Patient Index | Cardiomyopathy | Standard LGE-MRI Artifact Location | Wideband Protocol LGE Scar location. | Electroanatomical Voltage map. | Electrogram RF Target | Scar Area cm$^2$ (wideband MRI and EAM) |
|---|---|---|---|---|---|---|
| 9. | Ischemic | Significant Apex and lateral wall | Inferior lateral subendocardial scar | Inferior lateral endo scar | Split potentials and border zone substrate modification | MRI Endo: 13.2 EAM Endo: 11.3 |
| 10. | Hypertrophic Cardiomyopathy | Entire LV | Transmural scar extending from LV midcavity to apex. | Large Mid septal scar endo and anterior wall and small apical scar epi. | Border zone substrate modification. | MRI Endo: 41.5 Epi: 16 EAM Endo: 37.7 Epi: 9.8 |
| 11. | Tachycardia cardiomyopathy | No artifact. (Large ICD distance from LV border) | No scar | No scar | NSVT originating from LVOT, right coronary cusp. | MRI Endo: No scar Epi: No scar EAM Endo RV and LVOT: No scar |
| 12. | Non-ischemic | Anterior and apex. | Apical aneurysm | PVC map only. No voltage data. | Earliest activation in Anterior wall. | MRI Transmural: 10.5 EAM Not performed |
| 13. | Non-ischemic | Artifactapical. | No scar | No scar | Four VT morphologies induced, targeted VT in RVOT, −40 ms pre QRS. | MRI Endo: No scar Epi: No scar EAM Endo: No scar Epi: No scar |

*Epi = Epicardial;
Endo = Endocardial

DISCUSSION

The majority of patients referred for VT ablation do not undergo MRI imaging due to the relative contraindications of safety, coupled with the high likelihood of device-related artifact that diminishes the imaging yield and clinical utility. Several studies have confirmed the safety of 1.5 Tesla MRI in patients with implantable devices although the minority underwent cardiac MRI in the presence of an ICD. The present data were the first to demonstrate the clinical utility and EAM correlation of a novel wideband LGE sequence that effectively eliminates artifact and enables accurate interpretation of LGE images in patients with ICDs.

The ICD can introduces two distinct types of artifact due to the outer components of the generator, which causes 2-4 kHz frequency shift at a distance of 5-10 cm from the can. If the frequency shift is sufficiently strong to introduce an intra-voxel dephasing in the MRI signal, as is often the case for myocardium that is <5 cm away from the ICD, the affected regions will show as a dark signal void in both cardiac cine MRI and the LGE MRI. The second type of artifact is hyper-intensity artifact where the myocardium affected by the frequency shift is not strong enough to cause a signal void but is sufficiently strong to cause an improper inversion of the signal when applying the standard inversion pulse. The improper inversion is a result of the large frequency shift in the range of 2-4 kHz that is well outside the spectral bandwidth of the standard inversion pulse in LGE. Therefore, the hyper-intensity artifact is an issue only for pulse sequences that use an inversion pulse, such as LGE MRI.

The wideband LGE technique overcomes this hyper-intensity artifact by significantly increasing the spectral bandwidth of the inversion pulse. It is noted that the wideband technique does not add significant procedural risk to the patient as the increase in the specific absorption rate is largely negligible based on simulation studies. Hence, the wideband LGE can be easily integrated in any cardiac MRI scan protocol without any change in MRI pulse sequence timing or logistics.

The wideband pulse sequence has limitations under conditions of close proximity between the ICD can and heart and cannot overcome signal void causing black artifact. The data demonstrates the importance of ICD can proximity in artifact, in patient 17, the device was the closest to the heart of the series, overlying the heart on the anterior-posterior chest X-ray. This patient was the only patient where accurate wideband LGE-MRI interpretation was not possible due to extensive signal void artifact. On the contrary, patient 11 had the furthest ICD can from the LV border on chest X-ray (71.6 mm) and no artifact was seen with or without wideband LGE. The inverse relationship between the distance of the can from the heart and the extent of artifact seen has been previously reported by Sasaki et al. and has been confirmed in the study. The current findings suggest that the most important factor in determining amount of ICD artifact is the distance of ICD can from the heart (FIG. 17). Due to limitation of the chest X-ray as a projection imaging modality, the distance in the anterior-posterior direction could not be measured, which is a confounding factor in the correlation shown in FIG. 17.

Figure 21:
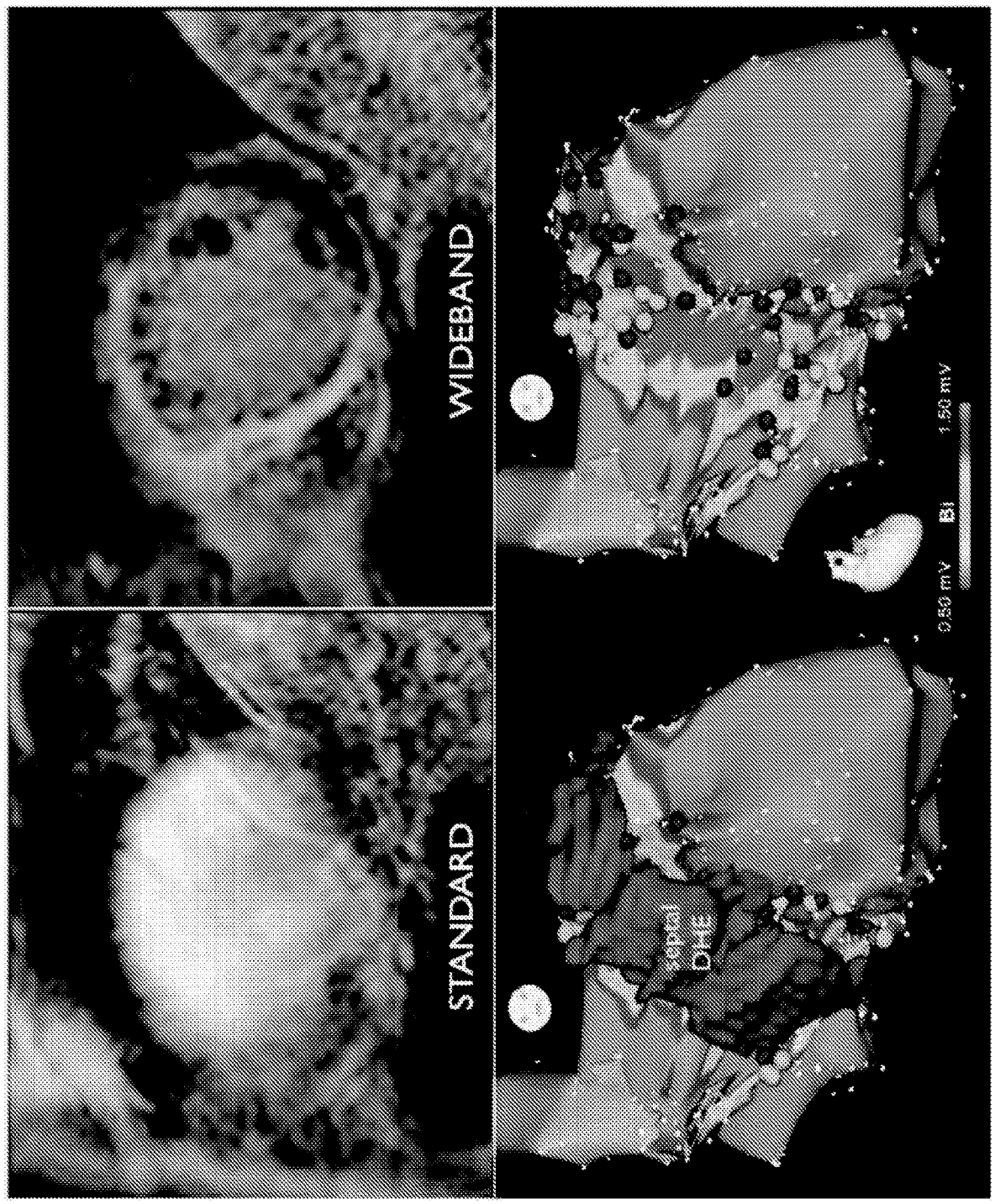
FIG. 21 illustrates an exemplary embodiment, showing standard MRI in upper left compared to wideband on upper right in a patient with hypertrophic cardiomyopathy, revealing significant septal and anterior wall scar, integrated with electroanatomical map on the bottom to guide substrate modification in real time.
Figure 22B:
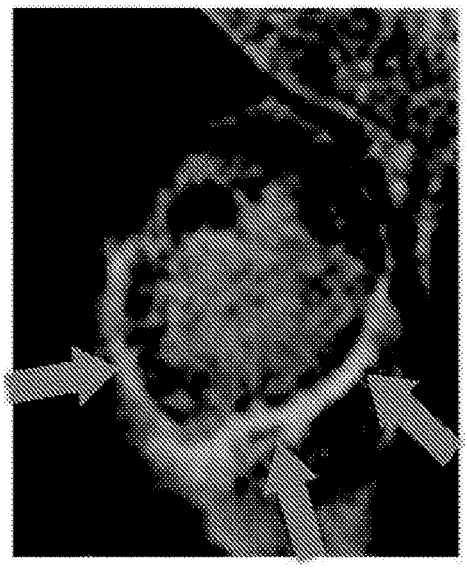
FIGS. 22A, 22B, 22C, and 22D illustrate an exemplary embodiment, showing conventional LGE (A & C) and new LGE (B & D) images from two patients. In both patients, severe bright signal artifacts (blue arrows) are produced in the conventional sequence, which prevents assessment of scar. The artifacts are completely eliminated by the new LGE technique. Scar tissue (red arrows) was identified in the anterior and septal walls of the left ventricle in Patient 1, and in the lateral wall of the left ventricle in Patient 2.
Figure 22D:
Figure 22A:
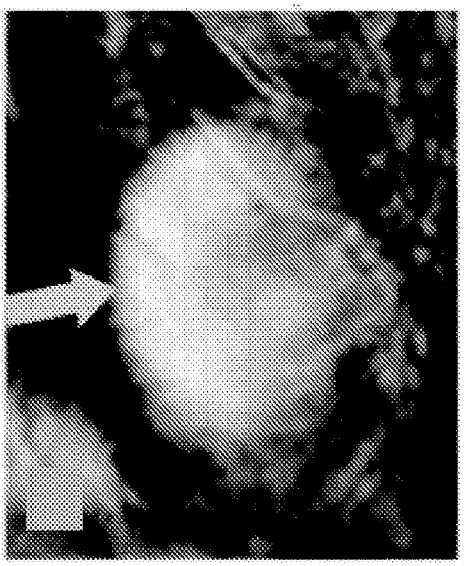
Figure 22C:
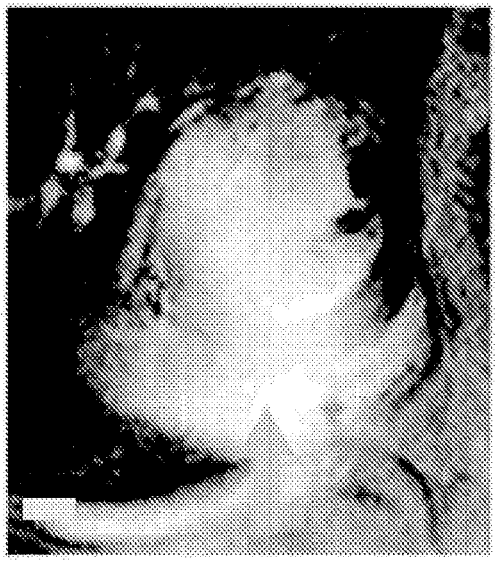

LGE-MRI has been shown to be a useful periprocedural adjunct for mapping and ablation of VT. The routine use of wideband LGE MRI for detection of LGE can enhance clinical decision making and periprocedural planning by allowing accurate visualization of LGE throughout all segments of the LV. Clinical decision making can be improved with LGE-MRI in the periprocedural setting for VT ablation. For example, in patient 1 preoperative understanding of the location of scar (transmural basal lateral and apex) allowed the upfront decision for epicardial access and high density electroanatomical maps in those regions. Without wideband LGE, the basal lateral scar could not be accurately seen in this patient (FIG. 16). Likewise, in patient 18, who was being evaluated for VT ablation and a history of non-ischemic cardiomyopathy, the MRI showed only very small areas of scar from the inferior wall, but the VT morphology suggested an anterior wall exit, and was too rapid to be safely mapped. Therefore, substrate modification would unlikely yield benefit, and instead the patient was referred for stellate ganglionectomy. This approach for preoperative planning for VT ablation allows us to use MRI assessment of scar in patients with hemodynamically significant VT to decide a priori if substrate modification will be feasible, avoiding risks of the invasive procedure among patients least likely to benefit. Another potential use for this technology is real-time integration of the MRI findings with the EAM map to allow real-time image guided catheter ablation, as was done in patient 10 as shown in FIG. 21.

In summary, the wideband LGE MRI is ready for widespread clinical use at specialized centers that have resources available to follow the appropriate MRI safety protocols of scanning patients with cardiac devices and have an indication to obtain myocardial scar images. Based on the experience, the improved wideband technique is expected to replace the standard LGE MRI with no increase in scan time, no change in imaging setup, minimal change in MRI safety profile and greatly improved image quality, which can be incorporated into clinical decision making Although the current study focuses on preoperative LGE MRI for VT ablation, it is straightforward to apply the technique on other patient populations with cardiac devices who can benefit from a cardiac MRI scan.

Limitations

The wideband protocol is specific for LGE-MRI, and does not overcome other types of image artifacts in cardiac cine images, which can be important for clinical interpretation of the images. The wideband protocol was done on one platform (Siemens, Malvern, Pa.), and the ability to incorporate this technique across a broad range of commercial systems is currently being tested. The electroanatomical maps were used to correlate MRI findings, and EAM is limited by tissue contact, the number of mapping points taken, and is operator dependent. Furthermore, epicardial fat is difficult to distinguish from scar, possibly overestimating scar size on the epicardium. Only dense scars were measured (<0.5 mV) to calculate epicardial scar area, and the epicardial EAM scars were smaller than those measured on MRI, although only 4 scars were compared in FIG. 20. Similar findings in a porcine model suggested that MRI correlates better with dense scar than border zone plus dense scar. There remains no other gold standard for scar imaging to compare the MRI results to. Lastly, the study is a small clinical study with only 18 patients. A larger multi-center study is clearly warranted to confirm the findings and to appropriately identify specific patient groups that are most likely to benefit from this technique.

With regard to device safety, ICD interrogations were performed before and after MRI without systematic recording of device parameters into the electronic medical record. Although no significant changes in lead characteristics and device measurements were observed in all patients, specific quantification of lead thresholds and impedances could not be reported in this cohort.

When comparing the correlation between scar size on MRI and EAM, important differences in spatial resolution should be acknowledged. The spatial resolution of MRI at 8 mm slices (1.4×1.9 mm) is smaller than a mapping electrode, where a bipole of 2 mm with 2 mm inter-electrode spacing contains the electrical signal of up to 6 mm edge-to-edge. In addition, the standard interpolation setting of electroanatomical mapping is 15 mm, which is larger than a representative slice on MRI. These discrepancies may result in an overestimation of scar on EAM compared to MRI. Although higher mapping density is performed at border zones to improve the scar contour definition, the variability due to operator and ease of catheter access exists between cases.

Conclusion

The majority of patients referred for VT ablation have ICDs, which obscures the image quality of LGE-MRI. A novel wideband LGE MRI artifact correction protocol to image ventricular scar is clinically safe and feasible. Reduction and/or removal of ICD artifacts can improve the ability to visualize myocardium for clinical interpretation, which correlated well with EAM findings during VT ablation.

Example 7

Artifact Reduction in Clinical Studies

The presence of an ICD causes bright artifacts to appear in LGE images (FIG. 22) and can prevent assessment of myocardial scar. Here, clinical results are presented that have implemented a new LGE MRI technique that removes these artifacts and produces diagnostically useful LGE images in ICD patients.

Methods

The bright artifacts in LGE images of ICD patients are caused by severe off-resonance produced by the ICD. Spins in the affected myocardium are not inverted by the IR pulse and give rise to the bright artifacts. In the new sequence, the bandwidth of the non-selective IR pulse was increased to excite the off-resonant spins, thereby eliminating the bright artifacts. The new technique was implemented at the medical centers of the University of California, Los Angeles (UCLA), and the University of Pennsylvania (UPenn). A total of 23 ICD patients (UCLA: 17, UPenn: 6), who were referred for a cardiac MRI exam prior to VT-ablation, were imaged using the conventional and the new LGE technique. The LGE images were read by two radiologists. The left ventricle was divided into 13 segments (basal, mid-ventricular, and apical, each having posterior, lateral, anterior and septal segments, and an individual apex segment), and artifact-containing segments in each patient were identified.

Results

Figure 23:
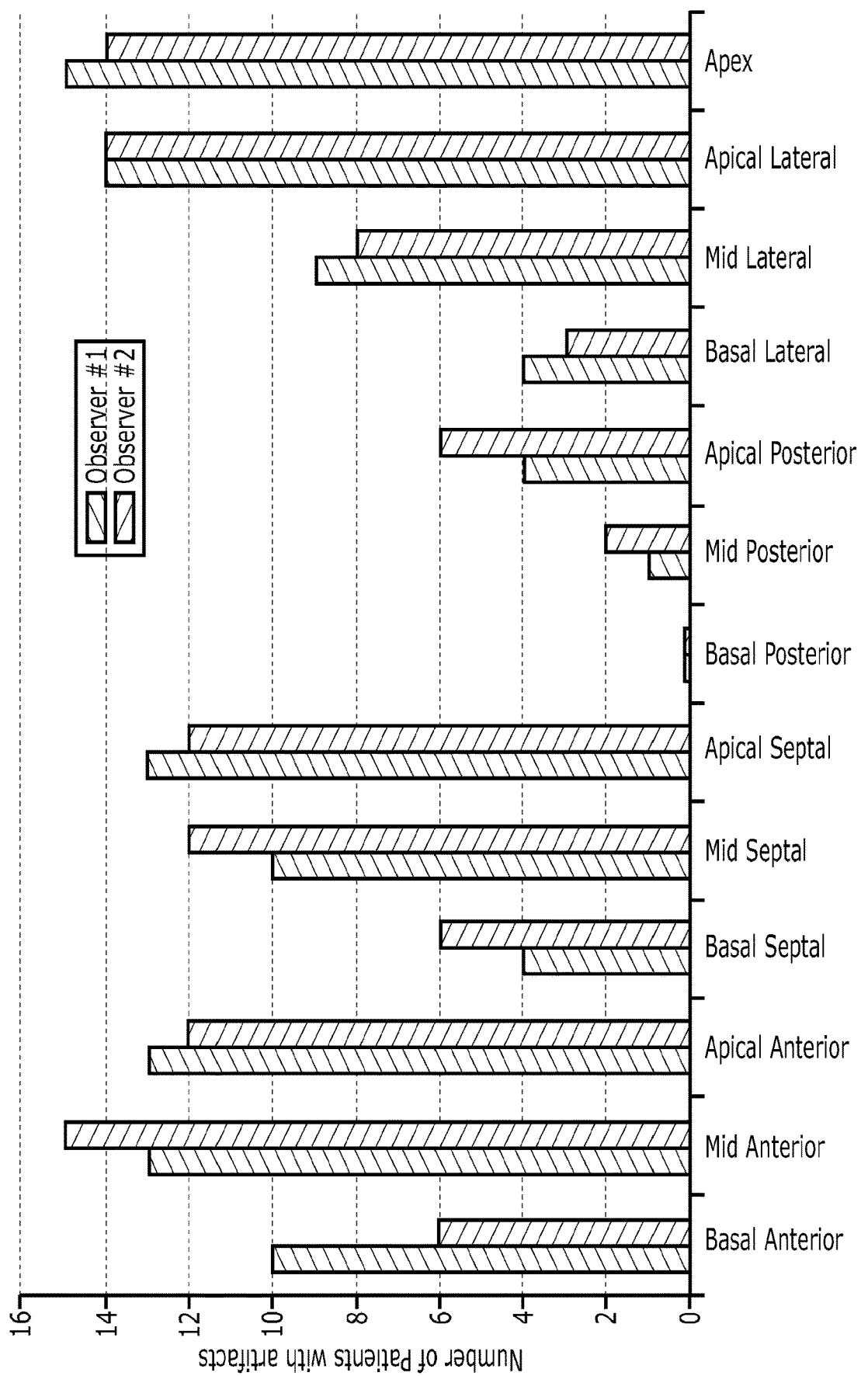
FIG. 23 illustrates an exemplary embodiment, showing the number of patients who presented artifacts in each of the 13 segments of the left ventricle. The 3 segments that had the highest occurrence of artifacts are the apex, the apical lateral segment and the mid-ventricular anterior segment.

No artifacts were produced in the conventional LGE image in 3 patients, owing to large distance of the ICD from the heart. In the remaining patients, bright artifacts were produced in 5.6±2.4 segments per patient in the conventional LGE images. All artifacts were completely eliminated in each patient using the new LGE technique. FIG. 22 shows examples of LGE images from the conventional and new LGE technique. FIG. 23 shows the number of patients that had artifacts in each of the 13 segments. The three segments with the largest number of artifacts are the apex, the apical lateral and the mid-ventricular anterior segment.

Conclusion

A new technique was developed to eliminate the bright artifacts seen in LGE MRI of patients with ICDs. This technique was implemented at two centers and successfully evaluated on 23 patients, leading to prominent reduction of the bright artifacts. It is expected that the technique to lead to increased application of MR scar imaging for the large population of patients with cardiac devices prior to catheter ablation of scar-mediated VT.

The various methods and techniques described above provide a number of exemplary ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

I claim:

1. A method for acquiring an image of a subject using a magnetic resonance imaging (MRI) system, the method comprising:
    selecting an inversion time (TI) to null signal from a desired tissue type during the performance of a pulse sequence designed to acquire late-gadolinium enhanced (LGE) T1-weighted images from a region of interest in the subject;
    selecting a wideband inversion recovery (IR) pulse having a spectral bandwidth between 1 kHz to 5 kHz and that is designed to invert the desired tissue type and tissue that are experiencing off-resonance effects;
    selecting an excitation radio frequency (RF) pulse having an RF spectral bandwidth;
    performing the pulse sequence using the selected excitation RF pulse, TI, and IR pulse to acquire MRI data from the subject; and
    reconstructing the MRI data to create an image of the subject having artifacts induced by the off-resonance effects reduced, wherein the artifacts in the image of the subject are hyper-intensity image artifacts; and
    displaying the image on a display.

2. The method of claim 1, wherein the spectral bandwidth of the wideband IR pulse is between 1.5 kHz to 5 kHz.

3. The method of claim 1, wherein the wideband IR pulse has a specific absorption rate (SAR) of 0.07 W/kg or lower.

4. The method of claim 1, wherein the wideband IR pulse is an adiabatic pulse.

5. The method of claim 1 wherein the wideband pulse is formed from a series of inversion pulses.

6. The method of claim 5 wherein the series of inversion pulses is formed by a plurality of inversion pulses played out in a back-to-back arrangement, wherein each of the plurality of the inversion pulses has a different center modulation frequency.

7. The method of claim 5 wherein the series of inversion pulses includes interleaved on-resonance and off-resonance inversion pulses.

8. The method of claim 5 wherein the series of inversion pulses include adiabatic pulses.

9. The method of claim 5 wherein the series of inversion pulses includes non-adiabatic pulses.

10. The method of claim 1 wherein the IR and excitation pulses of the pulse sequence are non-selective to control against signal distortion or pile-up artifacts in the image of the subject.

11. The method of claim 1 wherein the pulse sequence includes performing only one IR pulse prior to an imaging shot to allow full longitudinal signal relaxation for each spectral bin.

12. The method of claim 1 wherein the IR pulse has a boxcar spectral profile.

13. The method of claim 1 wherein the pulse sequence includes one of an IR turbo spin echo (TSE) or an IR spoiled gradient echo pulse sequence.

14. The method of claim 1 further comprising performing a self-gating technique to achieve respiratory gating when reconstructing the image of the subject.

15. The method of claim 1 wherein the desired tissue type includes myocardium.

16. The method of claim 1 wherein the spectral bandwidth of the wideband IR pulse is 1.5 kHz, 2 kHz, 2.5 kHz, 3 kHz, 3.5 kHz, or 3.8 kHz.

17. The method of claim 1 further comprising performing a shifting of a center modulation frequency of the pulse sequence by an amount selected from the group consisting of 50 Hz, 100 Hz, 150 Hz, 200 Hz, 250 Hz, 300 Hz, 350 Hz, 400 Hz, 450 Hz, 500 Hz, 550 Hz, 600 Hz, 650 Hz, 700 Hz, 750 Hz, 800 Hz, 850 Hz, 900 Hz, 950 Hz, 1000 Hz, 1050 Hz, 1100 Hz, 1150 Hz, 1200 Hz, 1250 Hz, 1300 Hz, 1350 Hz, 1400 Hz, 1450 Hz, 1500 Hz, 1550 Hz, 1600 Hz, 1650 Hz, 1700 Hz, 1750 Hz, 1800 Hz, 1850 Hz, 1900 Hz, 1950 Hz, 2000 Hz, 2050 Hz, 2100 Hz, 2150 Hz, 2200 Hz, 2250 Hz, 2300 Hz, 2350 Hz, 2400 Hz, 2450 Hz, and 2500 Hz.

18. The method of claim 1 wherein the region of interest includes an implantable cardioverter defibrillators (ICD), cardiac pacemakers (PM), an implantable cardiac defibrillator (ICD), a catheter, or a balloon.

\* \* \* \* \*